US011622569B2

(12) United States Patent
Davis et al.

(10) Patent No.: US 11,622,569 B2
(45) Date of Patent: *Apr. 11, 2023

(54) BACILLUS MICROBIAL TERROIR FOR PATHOGEN CONTROL IN SWINE

(71) Applicant: CHURCH & DWIGHT CO., INC., Princeton, NJ (US)

(72) Inventors: Mari Ellen Davis, Waukesha, WI (US); Justin Sawall, Waukesha, WI (US); Kim Friesen, Carthage, IN (US)

(73) Assignee: Church & Dwight Co., Inc., Princeton, NJ (US)

(*) Notice: Subject to any disclaimer, the term of this patent is extended or adjusted under 35 U.S.C. 154(b) by 150 days.

This patent is subject to a terminal disclaimer.

(21) Appl. No.: 16/043,610

(22) Filed: Jul. 24, 2018

(65) Prior Publication Data
US 2019/0021341 A1 Jan. 24, 2019

Related U.S. Application Data

(60) Provisional application No. 62/536,312, filed on Jul. 24, 2017.

(51) Int. Cl.
*A23K 10/18* (2016.01)
*A61K 9/19* (2006.01)
(Continued)

(52) U.S. Cl.
CPC .............. *A23K 10/18* (2016.05); *A01N 63/22* (2020.01); *A23K 10/12* (2016.05); *A23K 10/16* (2016.05);
(Continued)

(58) Field of Classification Search
CPC ........ A23K 10/16; A23K 10/18; A23K 50/00; A01N 63/10; A01N 63/00; A01N 63/22; A23L 33/135
See application file for complete search history.

(56) References Cited

U.S. PATENT DOCUMENTS 6,051,219 A 4/2000 Kubota
6,140,106 A 10/2000 Lawler et al.
(Continued)

FOREIGN PATENT DOCUMENTS

CN 102223809 A 10/2011
CN 104487566 A 4/2015
(Continued)

OTHER PUBLICATIONS

Antheunisse, "Viability of lyophilized microorganism after storage", Antonie van Leeuwenhoek, 1973, 39, pp. 243-248. (Year: 1973).*

(Continued)

*Primary Examiner* — Changqing Li
(74) *Attorney, Agent, or Firm* — Church & Dwight Co., Inc.

(57) ABSTRACT

Disclosed are methods of administering one or more *Bacillus subtilis* strains to swine. The *Bacillus subtilis* strains that are administered include 747 (NRRL B-67257), 1104 (NRRL B-67258), 1541 (NRRL B-67260), 1781 (NRRL B-67259), 2018 (NRRL B-67261), and BS1999 (NRRL B-67318). The *Bacillus* strains improve bacterial homeostasis in the gastrointestinal tract by inhibiting bacterial pathogens such as *E. coli*, *Clostridium*, *Salmonella*, and *Streptococcus*. Administering the *Bacillus* strains also improves performance such as weight gain and feed conversion. Useful combinations of *Bacillus* strains and methods of using one or more *Bacillus* strains are also provided.

16 Claims, 9 Drawing Sheets
Specification includes a Sequence Listing.

(51) Int. Cl.
  *A23K 10/16* (2016.01)
  *A23L 33/135* (2016.01)
  *A61K 35/742* (2015.01)
  *A61K 9/00* (2006.01)
  *A01N 63/22* (2020.01)
  *A23K 10/12* (2016.01)
  *A23K 50/30* (2016.01)
  *A23K 50/60* (2016.01)
  *A61K 35/00* (2006.01)

(52) U.S. Cl.
  CPC .............. *A23K 50/30* (2016.05); *A23K 50/60* (2016.05); *A23L 33/135* (2016.08); *A61K 9/00* (2013.01); *A61K 9/19* (2013.01); *A61K 35/742* (2013.01); *A61K 2035/115* (2013.01)

(56) References Cited

U.S. PATENT DOCUMENTS

| | | | |
|---|---|---|---|
| 6,162,634 | A | 12/2000 | Lawler et al. |
| 6,162,635 | A | 12/2000 | Lawler et al. |
| 6,422,174 | B1 | 7/2002 | Horikawa et al. |
| 6,660,294 | B2 | 12/2003 | Maruta et al. |
| 6,812,022 | B1 | 11/2004 | Aonuma |
| 6,989,370 | B2 | 1/2006 | Fahrlander et al. |
| 7,247,299 | B2 | 7/2007 | Lin et al. |
| 7,618,640 | B2 | 11/2009 | Rehberger et al. |
| 7,754,469 | B2 | 7/2010 | Baltzley et al. |
| 8,021,654 | B2 | 9/2011 | Rehberger et al. |
| 8,420,138 | B2 | 4/2013 | Knap et al. |
| 8,455,238 | B2 | 6/2013 | Baltzley et al. |
| 8,506,951 | B2 | 8/2013 | Rehberger et al. |
| 8,540,981 | B1 | 9/2013 | Wehnes et al. |
| 8,642,317 | B2 | 2/2014 | Zhou et al. |
| 8,722,058 | B2 | 5/2014 | Rehberger et al. |
| 8,741,280 | B2 | 6/2014 | Cantor et al. |
| 8,802,079 | B2 | 8/2014 | Knapp et al. |
| 9,005,601 | B2 | 4/2015 | Hargis et al. |
| 9,011,836 | B2 | 4/2015 | Rehberger et al. |
| 9,089,151 | B2 | 7/2015 | Davis et al. |
| 9,144,588 | B2 * | 9/2015 | Rubio ................ A61P 31/00 |
| 9,179,693 | B2 | 11/2015 | Romero |
| 9,247,757 | B2 | 2/2016 | Schmidt et al. |
| 10,201,574 | B1 * | 2/2019 | Rehberger ........... A61K 35/742 |
| 10,834,942 | B2 * | 11/2020 | Davis ................ A61K 35/742 |
| 10,835,561 | B2 * | 11/2020 | Rehberger ............ C12N 1/205 |
| 11,298,383 | B2 * | 4/2022 | Rehberger ............ A23K 50/75 |
| 2007/0202088 | A1 | 8/2007 | Baltzley et al. |
| 2009/0280090 | A1 | 11/2009 | Rehberger |
| 2010/0092428 | A1 | 4/2010 | Schmidt et al. |
| 2013/0330308 | A1 | 12/2013 | Millan |
| 2014/0037582 | A1 | 2/2014 | Romero et al. |
| 2015/0079058 | A1 | 3/2015 | Nielsen et al. |
| 2015/0118203 | A1 | 4/2015 | Boyette et al. |
| 2015/0216915 | A1 | 8/2015 | Frouel et al. |
| 2015/0230498 | A1 | 8/2015 | Davis et al. |
| 2015/0250831 | A1 | 9/2015 | Rehberger et al. |
| 2015/0257400 | A1 | 9/2015 | Reuter et al. |
| 2015/0290254 | A1 | 10/2015 | Remus et al. |
| 2015/0306154 | A1 | 10/2015 | Davis et al. |
| 2016/0007614 | A1 | 1/2016 | Rubio et al. |
| 2016/0120919 | A1 | 5/2016 | Ashida et al. |
| 2017/0014516 | A1 | 1/2017 | Petersen |
| 2019/0231828 | A1 * | 8/2019 | Rehberger ........... A61K 35/742 |
| 2021/0077545 | A1 * | 3/2021 | Rehberger ............. A61K 9/19 |

FOREIGN PATENT DOCUMENTS

| | | | |
|---|---|---|---|
| WO | WO 2010/065625 A1 | 6/2010 | |
| WO | WO 2012/110776 A2 | 8/2012 | |
| WO | WO-2012110777 A2 * | 8/2012 | ............... A61P 1/00 |
| WO | WO 2015/160960 A1 | 10/2015 | |
| WO | WO 2015/175667 A1 | 11/2015 | |
| WO | WO 2016/022779 A1 | 2/2016 | |
| WO | WO 2016/030441 A1 | 3/2016 | |
| WO | WO 2016/060934 A1 | 4/2016 | |
| WO | WO 2016/060935 A2 | 4/2016 | |
| WO | WO 2016/118840 A1 | 7/2016 | |
| WO | WO 2016/118850 A1 | 7/2016 | |
| WO | WO 2016/118864 A1 | 7/2016 | |
| WO | WO 2017/205645 A1 | 11/2017 | |

OTHER PUBLICATIONS

Aperce, C., et al., "Interaction of *Bacillus* species and *Salmonella enterica* serovar Typhimurium in immune or inflammatory signaling from swine intestinal epithelial cells," *J. Anim. Sci.*, 2010, vol. 88, pp. 1649-1656.

Baker, A., et al., "Prevalence and diversity of toxigenic *Clostridium perfringens* and *Clostridium difficile* among swine herds in the Midwest," *Midwest. Appl. Env. Microbiol.*, 2010, vol. 76, pp. 2961-2967.

Baker, A., et al., "The effect of a *Bacillus*-based direct-fed microbial supplemented to sows on the gastrointestinal microbiota of their neonatal piglets," *J. Anim. Sci.*, 2013, vol. 91, pp. 3390-3399.

Chen, Y., et al., "Effects of dietary *Bacillus*-based probiotic on growth performance, nutrients digestibility, blood characteristics and fecal noxious gas content in finishing pigs," *Asian-Aust. J. Anim. Sci.*, 2006, vol. 4, pp. 587-592.

Cheng, G., et al., "Antibiotic alternatives: the substitution of antibiotics in animal husbandry," *Frontiers Microbiol.*, 2014, vol. 5, pp. 1-15.

Davis, M., et al., "Effect of a *Bacillus*-based direct-fed microbial feed supplement on growth performance and pen cleaning characteristics of growing-finishing pigs," *J. Anim. Sci.*, 2008, vol. 86, pp. 1459-1467.

Gottschalk, J., et al., "*Streptococcus suis*: a new emerging or an old neglected zoonotic pathogen?," *Future Microbiol.*, 2010, vol. 5, pp. 371-391 (abstract).

Gu, S., et al., "Potential probiotic attributes of a new strain of *Bacillus coagulans* CGMCC 9951 isolated from health piglet feces," *World J. Microbiol. Biotechnol.*, 2015, vol. 31, pp. 851-863 (abstract).

Haesebrouck, F., et al., "Efficacy of vaccines against bacterial diseases in swine: what can we expect?," *Vet. Microbiol.*, 2004, vol. 100, pp. 255-268.

Hentges, D. J., "Chapter Five—Gut flora in disease resistance," In *Probiotics: the scientific basis*, 1992, R. Fuller (Ed.), Chapman and Hall, London, UK.

Holtkamp, D. J., "Economic cost of major health challenges in large US swine production Systems—Part 1," The Pig Site, 2007, pp. 1-3.

Holtkamp, D., et al., "Assessment of the economic impact of porcine reproductive and respiratory syndrome virus on United States pork producers," *J Swine Health and Production*, 2013, pp. 72-84.

Hong, H., et al., "The use of bacterial spore formers as probiotics." *FEMS Microbial. Rev.*, 2005, vol. 29, pp. 813-835.

Hu, Y., et al., "Effects of *Bacillus subtilis* KN-42 on growth performance, diarrhea and faecal bacterial flora of weaned piglets," *Asian-Aust. J. Anim. Sci.*, 2014, vol. 27, pp. 1131-1140.

Kalemba, D., et anon, "Antibacterial and antifungal properties of essential oils," *Current Medicinal Chemistry*, 2003, vol. 10, pp. 813-829 (abstract).

Klose, V., et al., "In vitro antagonistic activities of animal intestinal strains against swine-associated pathogens," *Vet. Microbiol*, 2010, vol. 144, pp. 515-521 (abstract).

Kluge, H., et al., "Effect of benzoic acid on growth performance, nutrient digestibility, nitrogen balance, gastrointestinal microflora and parameters of microbial metabolism in piglets," *J. Anim. Physiol Anim. Nutr.*, 2006, vol. 90, pp. 316-324 (abstract).

Knap, I., et al., "*Bacillus subtillis* (DSM 17299) significantly reduces *Salmonella* in broilers," *Poultry Science*, 2011, vol. 90, pp. 1690-1694.

Kritas, S., et al., "Reproductive performance of sows was improved by administration of a sporing bacillary probiotic (*Bacillus subtilis* C-3102)," *J. Anim. Sci.*, 2015, vol. 93, pp. 405-413.

(56) References Cited

OTHER PUBLICATIONS

Marquardt, R., et al., "Passive protective effect of egg-yolk antibodies against enterotoxigenic *Escherichia coli* K88+ infection in neonatal and early-weaned piglets," *FEMS Immunol. Med. Microbiol.*, 1999, vol. 23, pp. 283-288.
Nietfeld, J., et al., "Preventing *Salmonella* infection in pigs with offsite weaning," *Swine Health Prod.*, 1998, vol. 6, pp. 27-32.
Prieto, M., et al., "Evaluation of the Efficacy and Safety of a Marine-Derived *Bacillus* Strain for Use as an In-Feed Probiotic for Newly Weaned Pigs," *PLOS One*, 2014, vol. 9(2), e88599 (pp. 1-12).
Shariat, N., et al., "CRISPR-MVLST subtyping of *Salmonella enterica* subsp. *enterica* serovars Typhimurium and Heidelberg and application in identifying outbreak isolates," *BMC Microbiol.*, 2013, vol. 13, p. 254.
Songer, J., et al., "Infection of neonatal swine with *Clostridium difficle*," *Swine Health Prod.*, 2000, vol. 8, pp. 185-189.
Thanawongnuwech, R., et al., "Pathogenesis of porcine reproductive and respiratory syndrome virus-induced increase in susceptibility to *Streptococcus suis* infection," *Vet. Pathol.*, 2000, vol. 37, pp. 143-152.
Tsukahara, T., et al., "The preventive effect of *Bacillus subtilus* strain DB9011 against experimental infection with enteroteoxcemic *Escherichia colo* in weaning piglets," *Anim. Sci. J.*, 2013, vol. 84, pp. 316-321 (abstract).
Upadhaya, S., et al., "Preliminary assessment on potentials of probiotic *B. subtilis* RX7 and *B. methylotrophicus* C14 strains as an immune modulator in *Salmonella*-challenged weaned pigs," *Anim. Health Prod.*, 2017, vol. 49, pp. 1065-1070 (abstract).
Vallet, J., et al., "A simple novel measure of passive transfer of maternal immunoglobulin is predictive of preweaning mortality in piglets," *The Veterinary Journal*, 2013, vol. 195, pp. 91-97.
Vondruskova, H., et al., "Alternatives to antibiotic growth promotors in prevention of diarrhea in weaned piglets: a review," *Veterinarni Medicina*, 2010, vol. 55, pp. 199-224.
Walsh, M., et al., "Controlling *Salmonella* infection in weanling pigs through water delivery of direct-fed microbials or organic acids. Part I: Effects on growth performance, microbial populations and immune status," *J. Anim. Sci.*, 2012, vol. 90, pp. 261-271.
Walsh, M., et al., "Controlling *Salmonella* infection in weanling pigs through water delivery of direct-fed microbials or organic acids. Part II: Effects on intestinal histology and active nutrient transport," *J. Anim. Sci.*, 2012, vol. 90, pp. 2599-2608.
Yang, G., et al., "Influence of orally fed a select mixture of *Bacillus* probiotics on intestinal T-cell migration in weaned MUC4 resistant pigs follow *Escherichia coli* challenge," *Vet. Res.*, 2016, vol. 47, p. 71.
Achanta, M., et al. (2012). Tissue expression and development regulation of chicken cathelicidin antimicrobial peptides. J. Anim. Sci. Biotechnol. 3, 15.
Agunos, A., et al. (2013). Antimicrobial therapy of selected diseases in turkeys, laying hens, and minor poultry Species in Canada. Can. Vet. J. 54, 1041-1052.
Aliakbarpour, H.R., et al. (2012). The Bacillus subtilis and Lactic Acid Bacteria Probiotics Influences Intestinal Mucin Gene Expression, Histomorphology and Growth Performance in Broilers. Asian-Australas. J. Anim. Sci. 25, 1285-1293.
Allen, H.K., and Stanton, T.B. (2014). Altered Egos: Antibiotic Effects on Food Animal Microbiomes. Annu. Rev. Microbiol. 68, 297-315.
Al-Sheikhly, F., and Truscott, R.B. (1977a). The interaction of Clostridium perfringens and its toxins in the production of necrotic enteritis of chickens. Avian Dis. 21, 256-263.
Al-Sheikly, F., and Truscott, R.B. (1977b). The pathology of necrotic enteritis of chickens following infusions of broth cultures of Clostridium perfringens into the duodenum. Avian Dis. 21, 230-240.
Bai, K., et al. (2016). Supplemental effects of probiotic Bacillus subtilis fmbJ on growth performance, antioxidant capacity, and meat quality of broiler chickens. Poult. Sci. pew246.
Barbosa, T.M., et al. (2005). Screening of Bacillus Isolates in the Broiler Gastrointestinal Tract. Appl. Environ. Microbiol. 71, 968-978.
Barker, M., et al., "Effects of Bioplus 2B and Levucell SB on Weanling Pig Growth Performance and Fecal Shedding in Response to Oral Challenge With *Salmonella* Serovar Typhimuruim," *Proceedings of the Kansas State University Swine Day*, 2003, pp. 136-140.
Barnes, HJ, Nolan L, and Vaillancourt J-P (2008). Colibacillosis. In Diseases of Poultry, Saif YM, Fadly AA, Glisson JR, McDougald LR, Nolan L, and Swayne DE, eds. (Ames, IA: ISA Press), pp. 691-732.
Bass, B., et al, "Impact of a whole yeast product on sow, litter, and nursery performance," *Arkansas Anim Sci Dep Rep 2012*, 2013, pp. 104-115.
Billington, S.J., et al., (1998). Clostridium perfringens type E animal enteritis isolates with highly conserved, silent enterotoxin gene sequences. Infect. Immun. 66, 4531-4536.
Blom, J., et al. (2016). Edgar 2.0: an enhanced software platform for comparative gene content analyses. Nucleic Acids Res. 44, W22-W28.
Buntyn, J., et al., "The Role of Direct-Fed Microbials in Conventional Livestock Production," *Anu. Rev. Anim. Biosci.*, 2016, vol. 4(1), pp. 335-355.
Cartman, S.T., (2008). Bacillus subtilis Spores Germinate in the Chicken Gastrointestinal Tract. Appl. Environ. Microbial. 74, 5254-5258.
Chen, X.H., et al. (2007). Comparative analysis of the complete genome sequence of the plant growth-promoting bacterium Bacillus amyloliquefaciens FZB42. Nat. Biotechnol. 25, 1007-1014.
Choi, J., et. Al, "Evaluation of multi-microbe probiotics prepared by submerged liquid or solid substrate fermentation and antibiotics in weaning pigs," *Livestock Science*, 2011, vol. 138(1), pp. 144-151.
Chowdhury, S.P., et al. (2015). Biocontrol mechanism by root-associated Bacillus amyloliquefaciens FZB42—a review. Front. Microbial. 6.
Cooper, K.K., and Songer, J.G. (2009). Necrotic enteritis in chickens: a paradigm of enteric infection by Clostridium perfringens type A. Anaerobe 15, 55-60.
Cooper, K.K., Songer, J.G., and Uzal, F.A. (2013). Diagnosing clostridial enteric disease in poultry. J. Vet. Diagn. Invest. 25, 314-327.
Cui, C., et. al., "Effects of dietary Bacillus subtilis on proportion of Bacteroidetes and Firmicutes in swine intestine and lipid metabolism," *Genetics and Molecular Research*, 2013, vol. 12, pp. 1766-1776.
Cui, K., et al., "Effects of dietary supplementation with *Bacillus subtilis* and yeast culture on growth performance, nutrient digestibility, serum indices and faeces microbiota of weaned piglets," *Journal of Animal and Feed Sciences*, 2019, vol. 28, pp. 328-336.
Darling, A.E., Mau, B., and Perna, N.T. (2010). progressiveMauve: Multiple Genome Alignment with Gene Gain, Loss and Rearrangement. PLOS One 5, e11147.
Davis, E., et al., "Administration of a *Bacillus* probotic to sows improves growth response and health of their progeny after weaning," *J. Anim. Sci.*, 2020, vol. 98: Suppl. 2 (Abstract #268_/.
Fahmy, M., et al., "Interrelations between some reproductive traits in swine," *Can. I Anim. Sci.*, 1971, vol. 52, pp. 39-45.
Fan, B., et al. (2015). dRNA-Seq Reveals Genomewide TSSs and Noncoding RNAs of Plant Beneficial Rhizobacterium Bacillus amyloliquefaciens FZB42. PLoS One 10.
Fascella, S., et al., "Experiences of Biological Control of *Pseudomonas viridiflava* on Cut Flowers of *Ranunculus asiaticus,*" *Acta Horticulturae*, 2015, No. 1099, pp. 291-295.
Fass (2010). Federation of Animal Science Societies- Guide for the Care and Use of Agricultural Animals in Research and Teaching, Third Edition, Jan. 2010.
Fleischmann, R., et al. (1995). Whole-genome random sequencing and assembly of Haemophilus influenzae Rd. Science 269, 496.
Fritts, C.A., Kersey, J.H., Motl, M.A., Kroger, E.G., Yan, F., Si, J., Jiang, Q., Campos, M.M., Waldroup, A.L., and Waldroup, P.W.

(56) References Cited

OTHER PUBLICATIONS (2000). Bacillus subtilis C-3102 (Calsporin) Improves Live Performance and Microbiological Status of Broiler Chickens. J. Appl. Poult. Res. 9, 149-155.

Geeraerts, S., et al. (2016). Vegetative Bacillus amyloliquefaciens cells do not confer protection against necrotic enteritis in broilers despite high antibacterial activity of its supernatant against Clostridium perfringens in vitro. Br. Poult. Sci. 57, 324-329.

Giang, H., et al., "Effects of supplementation of probiotics on the performance, nutrient digestibility and faecal microflora in growing-finishing pigs," *Asian Aust. J. Aim. Sci.*, 2011, vol. 24, pp. 655-661.

Glisson, J.R., et al. (2004). Comparative efficacy of enrofloxacin, oxytetracycline, and sulfadimethoxine for the control of morbidity and mortality caused by *Escherichia coli* in broiler chickens. Avian Dis. 48, 658-662.

Gomez, S., et al., "Combination of an enzymatically hydrolyzed yeast culture with a direct-fed microbial in the feeds of broiler chickens," *Asian-Aust J. Anim. Sci.*, 2012, vol. 25, pp. 665-673.

Grave, K., et al. (2004). What has happened in norway after the ban of avoparcin? Consumption of antimicrobials by poultry. Prev. Vet. Med. 62, 59-72.

Guabiraba, R., and Schouler, C. (2015). Avian colibacillosis: still many black holes. FEMS Microbiol. Lett. 362, fnv118.

Hatheway, C.L. (1990). Toxigenic clostridia. Clin. Microbiol. Rev. 3, 66-98.

Heier, B.T., et al. (2001). A field study of naturally occurring specific antibodies against Clostridium perfringens alpha toxin in Norwegian broiler flocks. Avian Dis. 45, 724-732.

Hibberd, M.C., et al. (2011). Multilocus Sequence Typing Subtypes of Poultry Clostridium perfringens Isolates Demonstrate Disease Niche Partitioning. J. Clin. Microbiol. 49, 1556-1567.

Hofacre, C.L., et al. (1998). Use of Aviguard and other intestinal bioproducts in experimental Clostridium perfringens-associated necrotizing enteritis in broiler chickens. Avian Dis. 42, 579-584.

Hofacre, C.L., et al. (2002). Effect of a commercial competitive exclusion culture on reduction of colonization of an antibiotic-resistant pathogenic *Escherichia coli* in day-old broiler chickens. Avian Dis. 46, 198-202.

Immerseel, F.V., et al. (2004). Clostridium perfringens in poultry: an emerging threat for animal and public health. Avian Pathol. 33, 537-549.

Immerseel, F.V., et al. (2009). Rethinking our understanding of the pathogenesis of necrotic enteritis in chickens. Trends Microbiol. 17, 32-36.

International Search Report and Written Opinion for PCT/US2017/034512, 2017, 16 pages.

Jang, Y., et al., "Effects of live yeast supplementation to gestation and lactation diets on reproductive performance, immunological parameters and milk composition in sows," *Livestock sci.*, 2013, vol. 152, pp. 167-173.

Jayaraman, S., et al., "Bacillus subtilis PB6 improves intestinal health of broiler chickens challenged with *Clostridium perfringens*-induced necrotic enteritis," *Poultry Science Association*, 2013, vol. 92(2), pp. 370-374.

Jeong, J. S., and Kim, I.H. (2014). Effect of Bacillus subtilis C-3102 spores as a probiotic feed supplement on growth performance, noxious gas emission, and intestinal microflora in broilers. Poult. Sci. 93, 3097-3103.

Jeong, H., Park, S.-H., and Choi, S.-K. (2015). Genome Sequence of Antibiotic-Producing Bacillus amyloliquefaciens Strain KCTC 13012. Genome Announc. 3.

Jiang, Z., et al. (2010). Net effect of an acute phase response-Partial alleviation with probiotic supplementation. Poult. Sci. 89, 28-33.

Johnson, T.J., et al. (2008). Identification of Minimal Predictors of Avian Pathogenic *Escherichia coli* Virulence for Use as a Rapid Diagnostic Tool. J. Clin. Microbiol. 46, 3987-3996.

Jost, B.H., et al. (2005). Atypical cpb2 Genes, Encoding Beta2-Toxin in Clostridium perfringens Isolates of Nonporcine Origin. Infect. Immun. 73, 652-656.

Jurgens, M., et al., "The effect of dietary active dry yeast supplement on performance of sows during gestation-lactation and their pigs," *J. Anim. Sci.*, 1997, vol. 75, pp. 53-597.

Kaldhusdal, M., Benestad, S.L., and Lovland, A. (2016). "Epidemiologic aspects of necrotic enteritis in broiler chickens—disease occurrence and production performance," Avian Pathol. 45, 271-274.

Kearse, M., et al. (2012). Geneious Basic: an integrated and extendable desktop software platform for the organization and analysis of sequence data. Bioinformatics 28, 1647-1649.

Kennedy, C.L., et al. (2005). The a-toxin of Clostridium septicum is essential for virulence: a-toxin of Clostridium septicum. Mol. Microbiol. 57, 1357-1366.

Keyburn, A.L., et al. (2008). NetB, a New Toxin That Is Associated with Avian Necrotic Enteritis Caused by Clostridium perfringens. PLoS Pathog. 4, e26.

Keyburn, A.L., et al. (2010a). NetB, a pore-forming toxin from necrotic enteritis strains of Clostridium perfringens. Toxins 2, 1913-1927.

Keyburn, A.L., et al. (2010b). Association between avian necrotic enteritis and Clostridium perfringens strains expressing NetB toxin. Vet. Res. 41, 21.

Kim, S., et al., "Effect of supplementing *Saccharomyces cerevisae* fermentation product in sow diets on reproductive performance in a commercial environment," *Canadian journal of animal sciences*, 2010, vol. 9, pp. 2290-232.

Koumoutsi, A., et al. (2004). Structural and Functional Characterization of Gene Clusters Directing Nonribosomal Synthesis of Bioactive Cyclic Lipopeptides in Bacillus amyloliquefaciens Strain FZB42. J. Bacteriol. 186, 1084-1096.

La Ragione, R.M., and Woodward, M.J. (2003). Competitive exclusion by Bacillus subtilis spores of *Salmonella enterica* serotype Enteritidis and Clostridium perfringens in young chickens. Vet. Microbiol. 94, 245-256.

La Ragione, R.M., et al. (2001). Bacillus subtilis spores competitively exclude *Escherichia coli* O78:K80 in poultry. Vet. Microbiol. 79, 133-142.

Lazarus, B., et al. (2015). Do Human Extraintestinal Escherichia coli Infections Resistant to Expanded-Spectrum Cephalosporins Originate From Food-Producing Animals? a Systematic Review. Clin. Infect. Dis. 60, 439-452.

Lee, K.W., et al. (2010). Effects of direct-fed microbials on growth performance, gut morphometry, and immune characteristics in broiler chickens. Poult. Sci. 89, 203-216.

Lee, K.W., et al. (2011a). Avian necrotic enteritis: Experimental models, host immunity, pathogenesis, risk factors, and vaccine development. Poult. Sci. 90, 1381-1390.

Lee, K.W., et al. (2011b). Bacillus subtilis-based direct-fed microbials augment macrophage function in broiler chickens. Res. Vet. Sci. 91, e87-e91.

Lee, K.W., et al. (2013). Effect of Bacillus subtilis-based Direct-fed Microbials on Immune Status in Broiler Chickens Raised on Fresh or Used Litter. Asian-Australas. J. Anim. Sci. 26, 1592-1597.

Lee, K.W., et al. (2014). Effects of salinomycin and Bacillus subtilis on growth performance and immune responses in broiler chickens. Res. Vet. Sci. 97, 304-308.

Li, B., et al. (2014). Responses of beneficial Bacillus amyloliquefaciens SQR9 to different soilborne fungal pathogens through the alteration of antifungal compounds production. Front. Microbial. 5.

Li, Y., et al. (2016). Effect of Bacillus subtilis CGMCC 1.1086 on the growth performance and intestinal microbiota of broilers. J. Appl. Microbial. 120, 195-204.

Lindemann, et al., "Benefits of Cel-Can® an enzymatically hydrolyzed yeast product, for sows and weanling pigs," *American Association of Swine Veterinarians Annual Meeting: Implementing Knowledge*, 2010, p. 183-186.

Lovland, A., et al. (2003). Diagnosing Clostridium perfringens-associated necrotic enteritis in broiler flocks by an immunoglobulin G anti-alpha-toxin enzyme-linked immunosorbent assay. Avian Pathol. 32, 527-534.

Lovland, A., et al. (2004).. Avian Pathol. 33, 81- 90.

(56) References Cited

OTHER PUBLICATIONS

Lu, J., et al. (2003). Diversity and Succession of the Intestinal Bacterial Community of the Maturing Broiler Chicken. Appl. Environ. Microbial. 69, 6816-6824.
Luo, C., et at (2015a). Nonribosomal Peptide Synthase Gene Clusters for Lipopeptide Biosynthesis in Bacillus subtilis 916 and Their Phenotypic Functions. Appl. Environ. Microbial. 81, 422-431.
Luo, C., et al. (2015b). Unusual Biosynthesis and Structure of Locillomycins from Bacillus subtilis 916. Appl. Environ. Microbiol. 81, 6601-6609.
Marsh, T.L., et al. (2000). Terminal Restriction Fragment Length Polymorphism Analysis Program, a Web-Based Research Tool for Microbial Community Analysis. Appl. Environ. Microbiol. 66, 3616-3620.
Maruta, K., et al., "Effects of Bacillus subtilis C-3102 intake on fecal flora of sows and on diarrhea and mortality rate of their piglets," *Anim. Sci., Technol.*, 1996, vol. 67, pp. 403-409.
Maurer, J.J., et al. (2002). Virulence factors associated with *Escherichia coli* present in a commercially produced competitive exclusion product. Avian Dis. 46, 704-707.
Min, B., et al., "The effect of Bacillus and active yeast complex supplementation on the performance, fecal Bacillus counts and ammonia nitrogen concentrations in weaned pigs," *J. Anim. Sci.*, 2003, vol. 82(Suppl. 1), p. 26, abstract.
Moran, E.T. (2014). Intestinal events and nutritional dynamics predispose Clostridium perfringens virulence in broilers. Poult. Sci. 93, 3028-3036.
Muller, P.Y., et at (2002). Processing of gene expression data generated by quantitative real-time RT-PCR. BioTechniques 32, 1372-1374, 1376, 1378-1379.
Neumann, A.P., and Rehberger, T.G. (2009). MLST analysis reveals a highly conserved core genome among poultry isolates of Clostridium septicum. Anaerobe 15, 99-106.
Neumann, A.P., et at (2010). Quantitative real-time PCR assay for Clostridium septicum in poultry gangrenous dermatitis associated samples. Mol. Cell. Probes 24, 211-218.
Nguyen, A. t. v., et al. (2015). Isolation and characterization of Bacillus subtilis CH16 strain from chicken gastrointestinal tracts for use as a feed supplement to promote weight gain in broilers. Lett. Appl. Microbiol. 60, 580-588.
Niilo, L. (1980). Clostridium perfringens in Animal Disease: a Review of Current Knowledge Can. Vet. J. 21, 141-148.
Nurk, S., et al. (2013). Assembling Genomes and Mini-metagenomes from Highly Chimeric Reads. In Research in Computational Molecular Biology, M. Deng, R. Jiang, F. Sun, and X. Zhang, eds. (Springer Berlin Heidelberg), pp. 158-170.
Park, J.H., and Kim, I.H. (2014). Supplemental effect of probiotic Bacillus subtilis B2A on productivity, organ weight, intestinal *Salmonella* microflora, and breast meat quality of growing broiler chicks. Poult. Sci. 93, 2054-2059.
Park, J.H., and Kim, I.H. (2015). The effects of the supplementation of Bacillus subtilis RX7 and B2A strains on the performance, blood profiles, intestinal *Salmonella* concentration, noxious gas emission, organ weight and breast meat quality of broiler challenged with *Salmonella typhimurium*. J. Anim. Physiol. Anim. Nutr. 99, 326-334.
Patterson, J.A., and Burkholder, K.M. (2003). Application of prebiotics and probiotics in poultry production. Poult. Sci. 82, 627-631.
Plante, P., et al., "Effect of supplementing the diet of lactating sows with NuPro® on sow lactation performance and piglet growth," *Canadian Journal of Animal Science*, 2011, vol. 91, pp. 295-300.
Power, E.G. (1996). RAPD typing in microbiology—a technical review. J. Hosp. Infect. 34, 247-265.
Pranoto, et al "Enhancing antimicrobial activity of chitosan films by incorporating garlic oil, potassium sorbate and nisin," *LWT—Food Science and Technology*, Academic Press, United Kingdom, 2005, vol. 38(8), pp. 859-865.
Primm, N.D., et al. (1997). Application of normal avian gut flora by prolonged aerosolization onto turkey hatching eggs naturally exposed to *Salmonella*. Avian Dis. 41, 455-460.
Rahimi, S., et al. (2011). Effect of direct-fed microbials on performance and Clostridium perfringens colonization of turkey poults. Poult. Sci. 90, 2656-2662.
Riley, M.A., et al. (2012). Resistance is futile: the bacteriocin model for addressing the antibiotic resistance challenge. Biochem. Soc. Trans. 40, 1438-1442.
Rimoldi, G., et al. (2015). Necrotic Enteritis in Chickens Associated with Clostridium sordellii. Avian Dis. 59, 447-451.
Rood, J.I., et al. (2016). NetB and necrotic enteritis: the hole movable story. Avian Pathol. J. WVPA 45, 295-301.
Seemann, T. (2014). Prokka: rapid prokaryotic genome annotation. Bioinformatics 30, 2068-2069.
Sen, S., et al. (2012). Effect of supplementation of Bacillus subtilis LS 1-2 to broiler diets on growth performance, nutrient retention, caecal microbiology and small intestinal morphology. Res. Vet. Sci. 93, 264-268.
Shojadoost, B., et al. (2012). The successful experimental induction of necrotic enteritis in chickens by Clostridium perfringens: a critical review. Vet. Res. 43, 74.
Smirnov, A., Perez, R., Amit-Ramach, E., Sklan, D., and Uni, Z. (2005). Mucin Dynamics and Microbial Populations in Chicken Small Intestine Are Changed by Dietary Probiotic and Antibiotic Growth Promoter Supplementation. J. Nutr. 135, 187-192.
Snoeyenbos, G.H., et al. (1978). Protecting chicks and poults from *Salmonellae* by oral administration of "normal" gut microflora. Avian Dis. 22, 273-287.
Soccol, C., et al., "The potential of probiotics: a review," *Food Technol. Biotechnol.*, 2010, vol. 48, pp. 413-434.
Songer, J.G. (1996). Clostridial enteric diseases of domestic animals Clin. Microbial. Rev. 9, 216-234.
Tagg, J.R., Dajani, et al. (1976). Bacteriocins of gram-positive bacteria. Bacterial. Rev. 40, 722-756.
Tam, N.K.M., et al. (2006). The Intestinal Life Cycle of Bacillus subtilis and Close Relatives. J. Bacterial. 188, 2692- 2700.
Tellez, G., et at (2012). Probiotics/direct fed microbials for *Salmonella* control in poultry. Food Res. Int. 45, 628-633.
Teo, A.Y.-L., and Tan, H.-M. (2005). Inhibition of Clostridium perfringens by a Novel Strain of Bacillus subtilis Isolated from the Gastrointestinal Tracts of Healthy Chickens. Appl. Environ. Microbial. 71, 4185-4190.
Timbermont, L., Haesebrouck, F., Ducatelle, R., and Immerseel, F.V. (2011). Necrotic enteritis in broilers: an updated review on the pathogenesis. Avian Pathol. 40, 341-347.
Uzal, F.A., McClane, B.A., Cheung, J.K., Theoret, J., Garcia, J.P., Moore, R.J., and Rood, J.I. (2015) Animal models to study the pathogenesis of human and animal Clostridium perfringens infections. Vet. Microbial. 179, 23-33.
Veum, T., et al., "Effect of supplemental yeast culture in sow gestation and lactation diets on apparent nutrient digestibles and reproductive performance through one reproductive cycle," *J. Anim. Sci.*, 1995, vol. 73, pp. 1741-1745.
Veerapandian, et al., "Analytical and biological characterization of quinazoline semicarbazone derivatives," *Med. Chem. Res.*, 2009, vol. 19(3), pp. 283-298.
Wattam, A., Gabbard, J., Shukla, M., and Sobral, B. (2014). Comparative Genomic Analysis at the PATRIC, A 42 Bioinformatic Resource Center. In Host-Bacteria Interactions, A.C. Vergunst, and D. O'Callaghan, eds. (Springer New York), pp. 287-308.
Wattiau, P., Renard, M.E., Ledent, P., Debois, V., Blackman, G., and Agathos, S.N. (2001). A PCR test to identify 43 bacillus subtilis and closely related species and its application to the monitoring of wastewater biotreatment. Appl. Microbial. Biotechnol. 56, 816-819.
Weinack, O.M., Snoeyenbos, G.H., Smyser, C.F., and Soerjadi, A.S. (1981). Competitive exclusion of intestinal colonization of *Escherichia coli* in chicks. Avian Dis. 25, 696-705.
WHO Global Strategy Recommendations http://www.who.int/drugresistance/ WHO_ Global_Strategy _Recommendations/en/index3.html.
Williams, J.G.K., Kubelik, A.R., Livak, K.J., Rafalski, J.A., and Tingey, S.V. (1990). DNA polymorphisms amplified by arbitrary primers are useful as genetic markers. Nucleic Acids Res. 18, 6531-6535.

(56) References Cited

OTHER PUBLICATIONS

Willoughby, D.H., Bickford, A.A., Cooper, G.L., and Charlton, B.R. (1996). Periodic Recurrence of Gangrenous Dermatitis Associated with Clostridium Septicum in a Broiler Chicken Operation. J. Vet. Diagn. Invest. 8, 259-261.

Wu, L., Wu, H.-J., Qiao, J., Gao, X., and Borriss, R. (2015). Novel Routes for Improving Biocontrol Activity of Bacillus Based Bioinoculants. Front. Microbiol. 6.

Yildirim, E., et al., "The Investigation of Endophytic Microorganisms As a Source for Silage Microbiocenosis Formation Using NGS-Sequencing," *Agricultural Biology*, 2015, vol. 50(6), pp. 832-838.

Yogaratnam, V. (1995). Analysis of the causes of high rates of carcase rejection at a poultry processing plant. Vet. Rec. 137, 215-217.

Yoo, H., et al., "Molecular typing and epidemiological survey of prevalence of Clostridium perfringens types by multiplex Pcr," *J. Clin. Microbial.*, (1997) vol. 35(1), pp. 228-232.

Zanello, G., et al., "Effects of dietary yeast strains on immunoglobulin in colostrum and milk of sows," *Vet. Immunology and Immunopathology*, 2012, vol. 152, pp. 20-27.

Zeriouh, H., de Vicente, A., Perez-Garcia, A., and Romero, D. (2014). Surfactin triggers biofilm formation of Bacillus subtilis in melon phylloplane and contributes to the biocontrol activity. Environ. Microbial. 16, 2196-2211.

Zhang, Z.F., and Kim, I.H. (2014). Effects of multistrain probiotics on growth performance, apparent ilea! nutrient digestibility, blood characteristics, cecal microbial shedding, and excreta odor contents in broilers. Poult. Sci. 93, 364-370.

Zhang, J., Kobert, k, Flouri, T., and Stamat2akis, A. (2014). PEAR: a fast and accurate illumina Paired-End reAd mergeR. Bioinformatics 30, 614-620.

Zhu, X.Y., Zhong, T., Pandya, Y., and Joerger, R.D. (2002). 16S rRNA-Based Analysis of Microbiota from the Cecum of Broiler Chickens. Appl. Environ. Microbial. 68, 124-137.

Zoetendal, E.G., Colter, C.T., Koike, S., Mackie, R.I., and Gaskins, H.R. (2004), Molecular Ecological Analysis of the Gastrointestinal Microbiota; a Review, *J. Nutr.*, 134, 465-472.

\* cited by examiner

Figure 3. Diversity of *Streptococcus* isolated from commercial swine farms based on sequencing of the 16S rRNA gene.

Figure 4. RAPD PCR genotype diversity of *E. coli* populations: baseline, post-CTC, post-DFM. ]

Figure 5. RAPD PCR genotype diversity of *Clostridia* populations: baseline, post-CTC, post-DFM.

BACILLUS MICROBIAL TERROIR FOR PATHOGEN CONTROL IN SWINE

CROSS-REFERENCE TO RELATED APPLICATIONS

The present application claims priority to U.S. Provisional Pat. App. No. 62/536,312, filed Jul. 24, 2017, the disclosure of which is incorporated herein by reference.

BIBLIOGRAPHY

Complete bibliographic citations of those references that are referred to herein by the first author's last name and year of publication in parentheses can be found in the Bibliography section, which precedes the claims.

FIELD OF THE INVENTION

This invention relates to compositions of novel microorganisms for improving gastrointestinal homeostasis by reducing bacterial pathogens thus reducing swine diseases and enhancing performance in swine.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 99344US_SeqList.txt, a creation date of Jul. 24, 2018, and a size of 7.06 KB. The sequence listing filed via EFS-Web is part of the specification and is hereby incorporated in its entirety by reference herein.

BACKGROUND

Historically, in-feed antibiotics have been used extensively in the U.S. swine industry for both therapeutic applications to control and treat disease and for growth promotion and improved production efficiency. The Veterinary Feed Directive went into effect Jan. 1, 2017, and its implementation has eliminated antibiotic use to promote growth and efficiency of livestock and has severely regulated their use for therapeutic purposes. Swine herds face multiple bacterial challenges, including *Escherichia coli*, *Salmonella*, *Clostridia*, and *Streptococcus suis*, and would benefit from alternative technologies to antibiotics that could offer preventative effects against these potentially pathogenic bacteria prior to disease manifestation resulting in the need for therapeutic treatment with antibiotics.

*Escherichia coli* are gram negative bacteria and are one of the most prevalent causes of diarrhea in the young pig. Colibacillosis from *E. coli* often occurs during three life stages of the pig: 1) neonatal diarrhea occurring the first few days after birth; 2) young piglet diarrhea occurring one week after birth to weaning; and 3) post-weaning diarrhea occurring the first few weeks after weaning (Bertschinger and Fairbrother, 1999). Mortality may reach as high as 70% for severe *E. coli* cases in the very young pig, with mortality much lower (10%) in older pigs but with economically significant reductions in weight gain and production efficiency (Taylor, 2013).

*Clostridia* are gram positive, soil-borne bacteria that form spores, so they can survive for long periods of time in a dormant state between disease outbreaks. These bacteria are associated with enteritis in pigs from toxin production by *Clostridium perfringens* Types A and C. *Clostridium perfringens* Type C is well controlled in swine herds through vaccination programs, but *C. perfringens* Type A has proven difficult to control. *Clostridium difficile* can also result in enteric disease in neonatal piglets, and is often associated with a decrease in intestinal microbial diversity associated with antibiotic use (Songer et al., 2000). *Clostridia* are prevalent in the intestinal tract of swine and are considered members of the normal enteric microbial population (Baker et al., 2010), making determination of the pathogenic strains difficult to determine. Likely, clostridial disease results from a bloom in the intestinal population of potentially pathogenic isolates that emerges from the interaction of environmental and herd management factors. The acute disease can be associated with rapid death in pigs, but the impact of the clostridial load in the intestinal tract on reduced production efficiency is likely a bigger economic loss than mortality.

*Salmonella* are gram negative bacteria causing disease in swine and in some cases, a food safety risk. Many serotypes of can be harbored by the pig, but those most likely to cause disease include *Salmonella choleraesuis*, *S. typhimurium*, and *S. derby*. If present in the swine herd, *Salmonella* disease often manifests during times of stress as diarrhea and general unthriftiness associated with poor health. In acute disease events, mortality associated with *Salmonella* can be very high, and further economic loss to the industry occurs due to body weight loss and poor growth of infected pigs (Nietfeld et al., 1998).

*Streptococcus suis* infection in swine is associated with septicemia and meningitis resulting in arthritis and neurological symptoms. *Streptococcus suis* predominately colonize the upper respiratory tract in swine, but are also present in the reproductive and gastrointestinal tracts (Haesebrouck et al., 2004). Most pigs harbor potentially virulent strains of *S. suis*, and it appears that virulence is dependent upon environmental stressors and compromised immunocompetence associated with viral infection (Dee et al., 1993; Thanawongnuwech et al., 2000). Pigs of all ages and production stages are susceptible to *S. suis* infection, although most disease cases occur in young growing pigs between three and 12 weeks of age; therefore economic losses can result from increased mortality rates, permanent health impairments translating to poor growth and general unthriftiness, as well as reproductive inefficiencies in the sow herd (Gottschalk et al., 2010).

Generally, antibiotic therapies administered orally or injected are most commonly used to treat pathogenic bacterial infections in swine; however, with the implementation of the Veterinary Feed Directive, other non-antibiotic remedies have grown in prevalence including the use of high levels of zinc oxide in the feed, vaccination programs, essential oil products, organic acids, and pre- and probiotics (Cheng et al., 2014; Kalemba and Kunicka, 2003; Kluge et al., 2006; Vondruskova et al., 2010; Zimmerman et al., 2012). Of the probiotics, *Bacillus* organisms are most often administered to livestock due to their stability in feed and their antimicrobial benefits in disease prevention (Hong et al., 2005).

*Bacillus* probiotics have growth promoting properties when administered to pigs (Chen et al., 2006; Davis et al., 2008), and these growth performance benefits have been attributed to the production of antimicrobial compounds that inhibit enteric pathogens (Hentges, 1992). Such effects are similar to the benefits derived from antibiotic administration, and *Bacillus* probiotics have been reported to enhance pig growth performance similar to antibiotic supplementation in feed (Hu et al. 2014). An in vitro screening assay testing for inhibition of target pathogens, a metabolite produced by B. subtilis was found to have anti-clostridial effects (Klose et al., 2010), and a B. coagulans isolate was reported to have antibacterial effects against E. coli, Salmonella, and S. suis (Gu et al., 2015). In challenge studies in which nursery pigs were orally inoculated with a pathogenic E. coli isolate, administration of Bacillus probiotics ameliorated enteritis and diarrhea by suppressing the growth of toxigenic E. coli and upregulating protective immunological responses in the pig gastrointestinal tract (Tsukahara et al., 2013; Yang et al., 2016). The administration of certain B. subtilis probiotics to sows has been shown to reduce naturally occurring Clostridia counts in the feces of their piglets (Baker et al., 2013; Kritas et al., 2015). Some studies have reported no benefit from Bacillus supplementation when young pigs were administered a Salmonella Typhimurium challenge (Walsh et al., 2012a; 2012b). In another Salmonella challenge study in pigs, Bacillus probiotics reduced fecal Salmonella counts, and it is thought that the protection from Salmonella infection by Bacillus is through immunomodulatory effects on the host (Aperce et al., 2010; Upadhaya et al., 2017).

The economic impacts due to herd health issues resulting from a bacterial infection causing enteric disease are estimated to be approximately $100 million per year, with an estimated impact as high as $655 million from complex viral infections that have associated secondary bacterial infection, such as with porcine respiratory and reproductive syndrome (Holtkamp, 2007; Holtkamp et al., 2013). Although several technologies mentioned in this review have touted antimicrobial effects against some swine pathogens and mentioned as antibiotic alternatives, but none provide the broad spectrum preventative control of growth promoting levels of antibiotics. Swine producers need effective tools in lieu of antibiotics for managing herd health and optimizing productivity in their operations. Bacillus subtilis strains carefully selected and combined to provide broad spectrum control of E. coli, Salmonella, Clostridia, and S. suis provide one such alternative to the multiple antibiotics available to treat these diseases and can be customized to meet the unique health challenges of specific swine herds.

SUMMARY OF THE INVENTION

The present invention, is intended to solve one or more of the problems noted above.

In accordance with an embodiment of the present invention, the disclosure relates to a composition comprising a biologically pure culture of one or more Bacillus strains selected from the group consisting of: Bacillus subtilis 747, Bacillus subtilis 1104, Bacillus subtilis 1541 Bacillus subtilis 1781, Bacillus subtilis 2018, and Bacillus subtilis 1999 (Accession Numbers: 747 (NRRL B-67257), 1104 (NRRL B-67258), 1541 (NRRL B-67260), 1781 (NRRL B-67259), 2018 (NRRL B-67261), and BS1999 (NRRL B-67318). As used herein, the Bacillus probiotic product may comprise a single Bacillus strain or any combination of two or more of the Bacillus strains in any proportion.

In one embodiment, the disclosure relates to a direct fed microbial composition comprising an isolated Bacillus strain wherein the composition inhibits at least one pathogen selected from Escherichia coli, Salmonella, Clostridia, and Streptococcus suis in a gastrointestinal tract of a swine having ingested an effective amount of said direct fed microbial composition.

In one embodiment, the disclosure relates to a composition having a biologically pure culture of one or more Bacillus strains selected from the group consisting of: Bacillus subtilis 747, Bacillus subtilis 1104, Bacillus subtilis 1541 Bacillus subtilis 1781, Bacillus subtilis 2018, and Bacillus subtilis 1999.

In one embodiment, the composition may comprise at least in part a direct fed microbial or probiotic.

1. In one embodiment, the composition may comprise at least two isolated Bacillus strain is chosen from at least of strains Bacillus subtilis 747, Bacillus subtilis 1104, Bacillus subtilis 1541 Bacillus subtilis 1781, Bacillus subtilis 2018, and Bacillus subtilis 1999.

In one embodiment, the composition may also include a carrier.

In one embodiment, the composition may also include a preservative.

In one embodiment, the composition may further comprise a cryoprotectant disposed about the isolated Bacillus strain, and wherein said isolated Bacillus strain is a powdered lyophilized isolated Bacillus strain.

In one embodiment the powdered lyophilized isolated Bacillus strain comprises Bacillus spores.

In one embodiment, the composition may also include an animal feed.

In one embodiment, the composition may also include a volume of feedstuff.

In one embodiment, the composition has a concentration of the biologically pure culture of one or more Bacillus strains in the composition of about $3.75 \times 10^5$ CFU/g of feed.

In the embodiment, the composition has a concentration of the isolated Bacillus strain in the composition of between about $1 \times 10^5$ CFU/g of feed and about $1 \times 10^6$ CFU/g of feed.

In one embodiment, the effective amount of the direct fed microbial composition ingested by the swine per day comprises a concentration of the isolated Bacillus strain of between about $1 \times 10^6$ CFU/swine and about $1 \times 10^9$ CFU/swine.

In one embodiment, the composition improves the fecal score of the swine at seven days post weaning, wherein the swine ingested the effective amount of said direct fed microbial composition between zero days post weaning from a sow to seven days post weaning from the sow.

In one embodiment, the composition improves the average fecal score of the swine during an initial 14 days of a nursery period, wherein the swine ingested the effective amount of said direct fed microbial composition between zero days post weaning from a sow to 14 days post weaning from the sow.

In one embodiment, the disclosure relates to a method of improving immune system function of an animal comprising administering to an animal an effective amount of the composition described herein.

In one embodiment, the disclosure relates to a method of reducing inflammation in an animal comprising administering to an animal an effective amount of the composition described herein.

In one embodiment, the disclosure relates to a method of modulating immune function in an animal comprising administering to an animal an effective amount of the composition described herein.

In one embodiment, the disclosure relates to a method of improving survivability in a group of animal comprising administering to the group of animal an effective amount of the composition described herein.

In one embodiment, the disclosure relates to a method of decreasing mortality in a group of animal comprising administering to the group of animal an effective amount of the composition described herein.

In one embodiment, the disclosure relates to a method of providing increased feed efficiency in an animal comprising administering to an animal an effective amount of the composition described herein.

In one embodiment, the disclosure relates to a method of increasing body weight in an animal comprising administering to an animal an effective amount of the composition described herein.

In one embodiment, the disclosure relates to a method of increasing pigs weaned from a sow comprising administering to the sow an effective amount of the composition described herein. In one embodiment, the disclosure relates to a method of providing reduced pathogenic bacteria counts in a gut of an animal comprising administering to the animal an effective amount of the composition described herein.

DETAILED DESCRIPTION

Figure 1A:
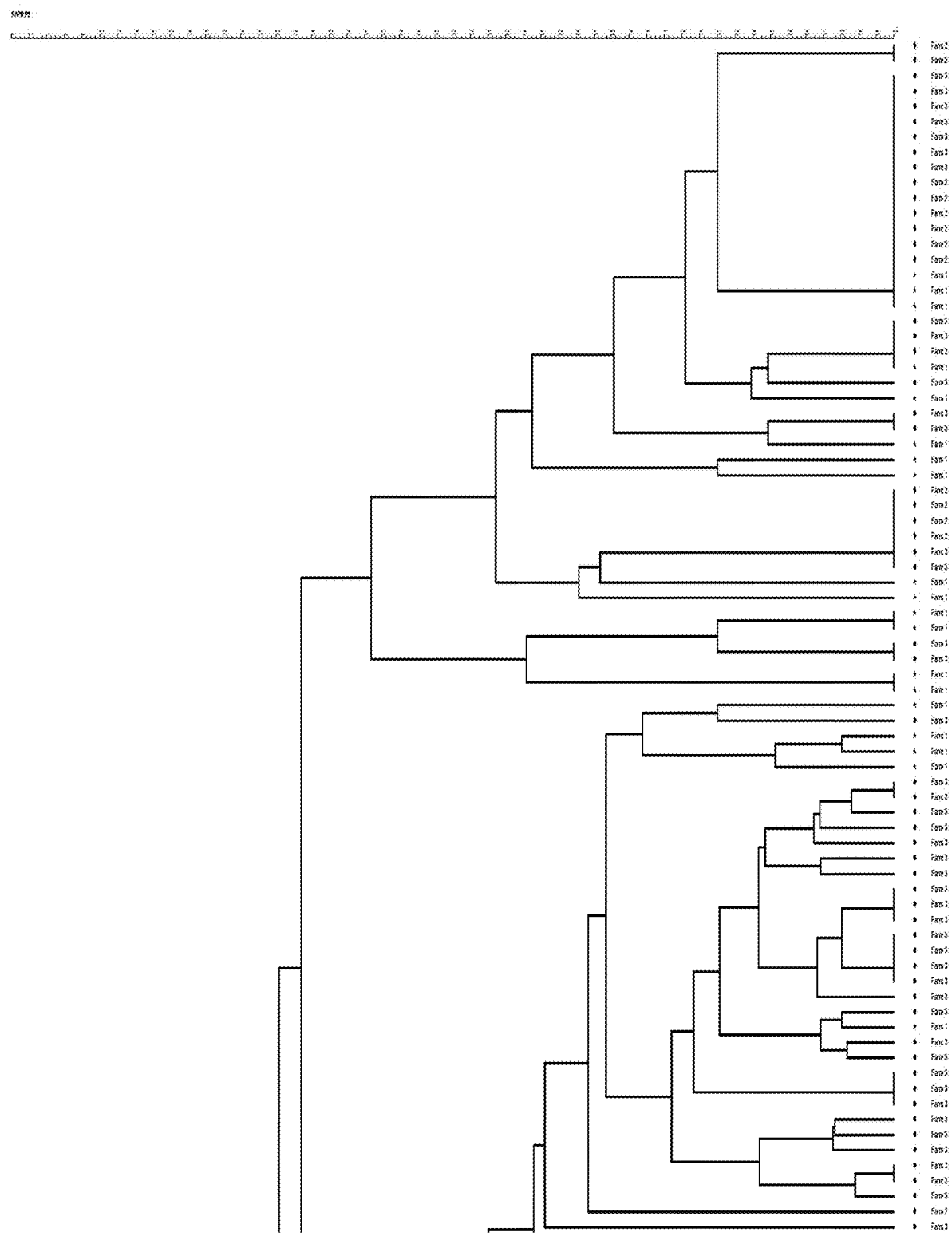
FIGS. 1A and 1B depict a graph showing a dendrogram of the genetic diversity of pathogenic *Escherichia coli* isolated from pigs selected for growth reduction assay based on RAPD fingerprint data.

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

Unless defined otherwise, all technical and scientific terms used herein have the same meaning as commonly understood by one of ordinary skill in the art to which this disclosure belongs.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

The headings provided herein are not limitations of the various aspects or embodiments of this disclosure, which can be had by reference to the specification as a whole. Accordingly, the terms defined immediately below are more fully defined by reference to the specification as a whole.

It is noted that, as used in the specification and the appended claims, the singular forms "a," "an," and "the" include plural referents unless the context clearly dictates otherwise.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, melt index, temperature etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, "administer" is meant the action of introducing the strain, and/or the combination of strains thereof to an environment.

As used herein, the term "animal" includes but is not limited to human, mammal, amphibian, bird, reptile, pigs, cows, cattle, goats, horses, sheep, poultry, and other animals kept or raised on a farm or ranch, sheep, big-horn sheep, buffalo, antelope, oxen, donkey, mule, deer, elk, caribou, water buffalo, camel, llama, alpaca, rabbit, mouse, rat, guinea pig, hamster, ferret, dog, cat, and other pets, primate, monkey, ape, and gorilla. In some embodiments, the animals are pig, including but not limited to sows, piglets and grow-finish.

By "at least one strain," is meant a single strain but also mixtures of strains comprising at least two strains of bacteria. By "a mixture of at least two strains," is meant a mixture of two, three, four, five, six or even more strains. In some embodiments of a mixture of strains, the proportions can vary from 1% to 99%. In certain embodiments, the proportion of a strain used in the mixture is at least 5%, 10%, 15%, 20%, 25%, 30%, 35%, 40%, 45%, 50%, 55%, 60%, 65%, 70%, 75%, 80%, 85%, 90%, or 95%. Other embodiments of a mixture of strains are from 25% to 75%. Additional embodiments of a mixture of strains are approximately 50% for each strain. When a mixture comprises more than two strains, the strains can be present in substantially equal proportions in the mixture or in different proportions.

As used herein, the term "feed" refers to a commercial feed. Feeds may be blended from various raw materials and additives. These blends are formulated according to the specific requirements of the target animal.

As used herein, "effective amount" is meant a quantity of strain, and/or the combination of strains thereof to improve performance of an animal. Improvement in performance can be measured as described herein or by other methods known in the art. An effective amount can be administered to the animal by providing ad libitum access to feed containing the strain and/or the combination of strains thereof. The strain and/or the combination of strains thereof can also be administered in one or more doses.

As used herein, the term "feed" is used synonymously herein with "feedstuff."

As used herein, the term "feed component" refers to all or part of the feedstuff. Part of the feedstuff may mean one constituent of the feedstuff or more than one constituent of the feedstuff. e.g. 2 or 3 or 4. The term "feed component" encompasses a premix or premix constituents.

As used herein, "performance" refers to the growth of an animal, such as a pig or poultry, measured by one or more of the following parameters: average daily gain (ADG), weight, scours, mortality, feed conversion, which includes both feed:gain and gain:feed, and feed intake. "An improvement in performance" or "improved performance" as used herein, refers to an improvement in at least one of the parameters listed under the performance definition.

As used herein, the term "protein" includes proteins, polypeptides, and peptides.

In one embodiment, the disclosure relates to one or more bacterial strains. In yet another embodiment, the disclosure relates to a composition comprising one or more bacterial strains. The bacterial strains may be selected from *Bacillus subtilis* 747, *Bacillus subtilis* 1104, *Bacillus subtilis* 1541 *Bacillus subtilis* 1781, *Bacillus subtilis* 2018, and *Bacillus subtilis* 1999 (deposits were made under the Budapest Treaty and assigned Accession Numbers, 747 NRRL B-67257, 1104 NRRL B-67258, 1541 NRRL B-67260, 1781 NRRL B-67259, 2018 NRRL B-67261, and BS1999 NRRL B-67318, respectively). The composition may be a liquid, a mixture, a solid, a powder, a solution, a dispersion, lyophilized, freeze-dried, or any combination thereof.

In one embodiment, the composition is a feed additive. In one embodiment, concentrations of the composition may be adjusted as described herein for administration to the desired animal stage. In one embodiment, the animal is a pig.

In one embodiment, one or more carriers or other ingredients can be added to the composition as disclosed herein. The composition may be administered in various physical forms, for example, a top dress, a water soluble concentrate, gels or gelatin capsules. Additives may include, but are not limited to growth substrates, enzymes, sugars, carbohydrates, extracts, and growth promoting ingredients.

The *Bacillus* strains can be produced by fermentation of the bacterial strains grown in a liquid nutrient broth. In at least one embodiment, the *Bacillus* strains are grown to a level at which the highest number of spores are formed. In a non-limiting example, fermentation can be started by scaling-up a seed culture. This involves repeatedly and aseptically transferring the culture to a larger and larger volume to serve as the inoculum for the fermentation, which is carried out in large stainless steel fermentors in medium containing proteins, carbohydrates, and minerals necessary for optimal growth. A non-limiting exemplary medium is TSB. After the inoculum is added to the fermentation vessel, the temperature and agitation are controlled to allow maximum growth. Once the culture reaches a maximum population density, the culture is harvested by separating the cells from the fermentation medium. This is commonly done by centrifugation.

In one embodiment, to prepare the *Bacillus* strains, each *Bacillus* strain is fermented to a $5 \times 10^3$ CFU/ml to about $4 \times 10^{12}$ CFU/ml level. The bacteria are harvested by centrifugation, and the supernatant is removed. In some embodiments, the bacteria is pelleted bacteria. In at least some embodiments, the pelleted bacteria are freeze-dried and mixed with a carrier. The strains can also be used with or without preservatives, and in concentrate, unconcentrated, or diluted form.

The count of the culture can then be determined. CFU or colony forming unit is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is a more useful unit measurement than cell number.

In another embodiment, the disclosure relates to a feed additive composition that may be used as a feed or in the preparation of a feed. The feed may be in the form of a solution or as a solid depending on the use and/or the mode of application and/or the mode of administration. When used as a feed or in the preparation of a feed, such as functional feed, the feed additive composition may be used in conjunction with one or more of the following: a nutritionally acceptable carrier, a nutritionally acceptable diluent, a nutritionally acceptable excipient, a nutritionally acceptable adjuvant, a nutritionally active ingredient. In one embodiment, the feed additive composition disclosed herein is mixed with a feed component to form a feedstuff. In one embodiment, the feed may be a fodder, or a premix thereof, a compound feed, or a premix thereof. In one embodiment, the feed additive composition disclosed herein may be admixed with a compound feed, a compound feed component or a premix of a compound feed or to a fodder, a fodder component, or a premix of a fodder.

In one embodiment, fodder may be obtained from one or more of the plants selected from: alfalfa (lucerne), barley, brassicas, Chau moellier, kale, rapeseed (canola), rutabaga (swede), turnip, clover, alsike clover, red clover, subterranean clover, white clover, grass, false oat grass, fescue, Bermuda grass, brome, heath grass, meadow grasses (from naturally mixed grassland swards, orchard grass, rye grass, Timothy-grass, corn (maize), millet, oats, sorghum, soybeans, trees (pollard tree shoots for tree-hay), wheat, and legumes.

Compound feeds can be complete feeds that provide all the daily required nutrients, concentrates that provide a part of the ration (protein, energy) or supplements that only provide additional micronutrients, such as minerals and vitamins. The main ingredients used in compound feed are the feed grains, which include corn, soybeans, sorghum, oats, and barley. A premix, as referred to herein, may be a composition composed of micro-ingredients such as vitamins, minerals, chemical preservatives, antibiotics, fermentation products, and other essential ingredients. Premixes are usually compositions suitable for blending into commercial rations.

In one embodiment, a feedstuff as disclosed herein may comprise one or more feed materials selected from the group comprising cereals, such as small grains (e.g., wheat, barley, rye, oats and combinations thereof) and/or large grains such as maize or sorghum; by products from cereals, such as com gluten meal, wheat bran, wheat middlings, wheat shorts, rice bran, rice hulls, oat hulls, palm kernel, and citrus pulp; protein obtained from sources such as soya, sunflower, peanut, lupin, peas, fava beans, cotton, canola, fish meal, dried plasma protein, meat and bone meal, potato protein, whey, copra, sesame; oils and fats obtained from vegetable and animal sources; and minerals and vitamins.

In yet another embodiment, a feedstuff may comprise at least one high fiber feed material and/or at least one by-product of the at least one high fiber feed material to provide a high fiber feedstuff. Examples of high fiber feed materials include: wheat, barley, rye, oats, by products from cereals, such as com gluten meal, wheat bran, wheat middlings, wheat shorts, rice bran, rice hulls, oat hulls, palm kernel, and citrus pulp. Some protein sources may also be regarded as high fiber: protein obtained from sources such as sunflower, lupin, fava beans and cotton In still another embodiment, the feed may be one or more of the following: a compound feed and premix, including pellets, a crop or crop residue: corn, soybeans, sorghum, oats, barley, copra, straw, chaff, sugar beet waste; fish meal; freshly cut grass and other forage plants; meat and bone meal; molasses; oil cake and press cake; oligosaccharides; conserved forage plants: hay and silage; seaweed; seeds and grains, either whole or prepared by crushing, milling etc.; sprouted grains and legumes; yeast extract.

In one embodiment the composition as disclosed herein is mixed with the feedstuff. Alternatively, the composition may be included in the emulsion or raw ingredients of a feedstuff.

In one embodiment, the disclosure relates to methods of increasing performance metrics of an animal. In another embodiment, the disclosure relates to methods of increasing performance metrics of a pig as described above.

Administration of the composition according to this disclosure is possible at any time, with or without feed. However, as described herein, one preferred administration is with feed.

Thus, in at least some embodiments, the effective amount of the composition according to the present disclosure is administered in an animal by supplementing a feed intended for the animal. As user herein, "supplementing," refers to the incorporation of an effective amount of the composition provided herein into the feed for the animal. As such, the animal will ingest the composition provided herein during feeding.

EXAMPLES

The following Examples are provided for illustrative purpose only. The Examples are included herein solely to aid in a more complete understanding of the presently described invention. The Examples do not limit the scope of the invention described or claimed herein in any fashion.

Example 1: Genetic Diversity of Pathogenic *E. coli* on Commercial Swine Farms and in Vitro Inhibition of *E. coli* Growth by Distinct *Bacillus subtilis* Isolates Pathogenic *E. coli* isolates can have varied susceptibility to the bacteriocins produced by different *Bacillus* strains. By isolating pathogenic *E. coli* isolates from swine at a particular farm/location and selecting a diverse set of representatives, the bacteriocins from the multiple *Bacillus* strains were tested for their effectiveness at inhibiting the growth of the pathogenic *E. coli* present in swine at a particular farm location.

*Escherichia coli* isolates were cultured from swine sources (fecal material or gastrointestinal tissue) on CHROMagar *E. coli* (CHROMagar), and grown aerobically at 37° C. for 24 h. Presumptive *E. coli* colonies were picked into Brain Heart Infusion (BHI) broth and incubated at 37° C. for 24 h.) Genomic DNA (gDNA) was extracted using the following method: Isolates were cultured overnight in 200 µL Brain Heart Infusion (BHI) broth (BD). Overnight cultures were centrifuged for 10 minutes, the supernatant discarded and the cell pellet resuspended in 500 µL of 50 mM Tris-HCl 10 mM EDTA, pH=8.0. The centrifugation process was repeated and cell pellets were resuspended in 200 µL of a 10 mg/mL lysozyme solution, and incubated for 1 hour at 37° C. Following the 1 hour incubation, 300 µL of a 6M Guanidine, 20% Triton-x 100, 10 mM Tris-HCl, pH=7.5 solution was added and the solution was incubated at room temperature for 15 minutes. Then, 20 µL of a 20 mg/mL proteinase K solution was added and the solution was incubated at 55° C. for 30 minutes. The cell lysate was then transferred into a 96 well binding plate (Promega) nested in a 96 well collection block (VWR). The binding plate was centrifuged for 5 minutes, the filtrate discarded, and 750 µL of Column Wash Solution (Promega) was added. This solution was centrifuged for 2 minutes the filtrate discarded. This wash step was repeated for a total of three washes and finally centrifuged for 10 minutes to remove excess wash solution. The binding plate was then placed in a 96 well PCR plate (VWR) and 100 µL nuclease free water, pre-warmed to 55° C., was added. The plate was incubated for 2 minutes at room temperature and centrifuged for 2 minutes to elute gDNA.

Pathogenic *E. coli* were identified by a multiplex PCR assay using primers specific for 5 adhesin and 4 toxin gene targets (Table 1). The multiplex PCR reaction mixture was as follows: 2 µL 10× GOLD PCR Buffer II, 0.4 µL of 10 mM dNTP mix, 1.5 µL 25 mM $MgCl_2$, 0.5 µL of each of the 18 primers (9 sets of Forward & Reverse primers), 5 µL of sterile water, 0.1 µL of AmpliTaq Gold (ThermoFisher Scientific), and 2 µL template gDNA (final volume=20 µL). The temperature cycle for the PCR is an initial 10 minutes at 94° C., then 35 cycles of 30 s at 94° C., 45 s at 54° C., and 90 s increasing 3 s per cycle at 72° C. Samples were run on a fragment analyzer (Advanced Analytics Technologies) to visualize amplification products. Isolates that tested positive for any one target gene were considered pathogenic.

TABLE 1

Primers used in pathogenic *E. coli* screen

| Primer | Sequence | SEQ ID NO: |
|---|---|---|
| Stx2eF | AATAGTATACGGACAGCGAT | 1 |
| Stx2eR | TCTGACATTCTGGTTGACTC | 2 |
| LTbF | GGCGTTACTATCCTCTCTAT | 3 |
| LTbR | TGGTCTCGGTCAGATATGT | 4 |
| STaPF | CAACTGAATCACTTGACTCTT | 5 |
| STaPR | TTAATAACATCCAGCACAGG | 6 |
| STbF | TGCCTATGCATCTACACAAT | 7 |
| STbR | CTCCAGCAGTACCATCTCTA | 8 |
| F18F | TGGTAACGTATCAGCAACTA | 9 |
| F18R | ACTTACAGTGCTATTCGACG | 10 |
| F41F | AGTATCTGGTTCAGTGATGG | 11 |
| F41R | CCACTATAAGAGGTTGAAGC | 12 |
| K99F | AATACTTGTTCAGGGAGAAA | 13 |
| K99R | AACTTTGTGGTTAACTTCCT | 14 |
| 987PF | AAGTTACTGCCAGTCTATGC | 15 |
| 987PR | GTAACTCCACCGTTTGTATC | 16 |
| K88F | GTTGGTACAGGTCTTAATGG | 17 |
| K88R | GAATCTGTCCGAGAATATCA | 18 |

The genetic diversity of the identified pathogenic *E. coli* was determined by obtaining randomly amplified polymorphic DNA (RAPD) profiles for each isolate. The PCR reaction was as follows: 5 µL gDNA, 2.5 µL RAPD primer 2 (10 µM) [GTTTCGCTCC, SEQ ID NO: 27], and 17.5 µL nuclease free water added to a GE RAPD bead tube (GE Healthcare). The temperature cycle was as follows: an initial 5 min at 95° C., then 45 cycles of 1 min at 95° C., 1 min at 36° C., 2 min at 72° C., and finally 5 min at 72° C. Samples were run on a fragment analyzer (Advanced Analytics Technologies) and RAPD profiles were used to compile a dendrogram of genetic similarity using BioNumerics bioinformatic software (Applied Maths).

Pathogenic *E. coli* isolates that were considered to be genetically distinct from each other (<80% genetically similar) were screened against the panel of six proprietary *B. subtilis* strains. The appropriate isolates were obtained from frozen stock cultures, picked into a 96 deep well plate containing 500 µL of BHI broth, and placed in the 37° C. incubator for 6-24 hrs. After incubation, the pure cell culture isolates were diluted in BHI by transferring 10 µL of pure *E. coli* culture into 190 µL BHI. Bacteriocin from each of the six *B. subtilis* strains was prepared by adding 170 µL of BHI to 30 µL of the *Bacillus* strain bacteriocin.

Each pure culture *E. coli* isolate was assayed in duplicate against the prepared bacteriocin from each of the six *Bacillus* strains. Briefly, the assay design included a positive control containing 195 µL of BHI and 5 µL of the diluted *E. coli* cell culture, the negative control contained 195 µL of BHI only, and the bacteriocin test wells contained 5 µL of the diluted *E. coli* culture and 195 µL of the respective bacteriocin from each of the six *Bacillus* strains. Plates were placed at 37° C. incubator for 18 hours and optical density was determined by reading on a Biotek Epoch Microplate Spectrometer at 600 nm wavelength. The following formula was used to determine the percent growth reduction of the *E. coli* culture: (1−((pure culture isolate−neg. control)/(pos. control−neg. control)))×100, and this value was used to determine the best formulation of *Bacillus* strains to include in a customized product to control a specific farm's pathogenic *E. coli*.

Figure 1B:
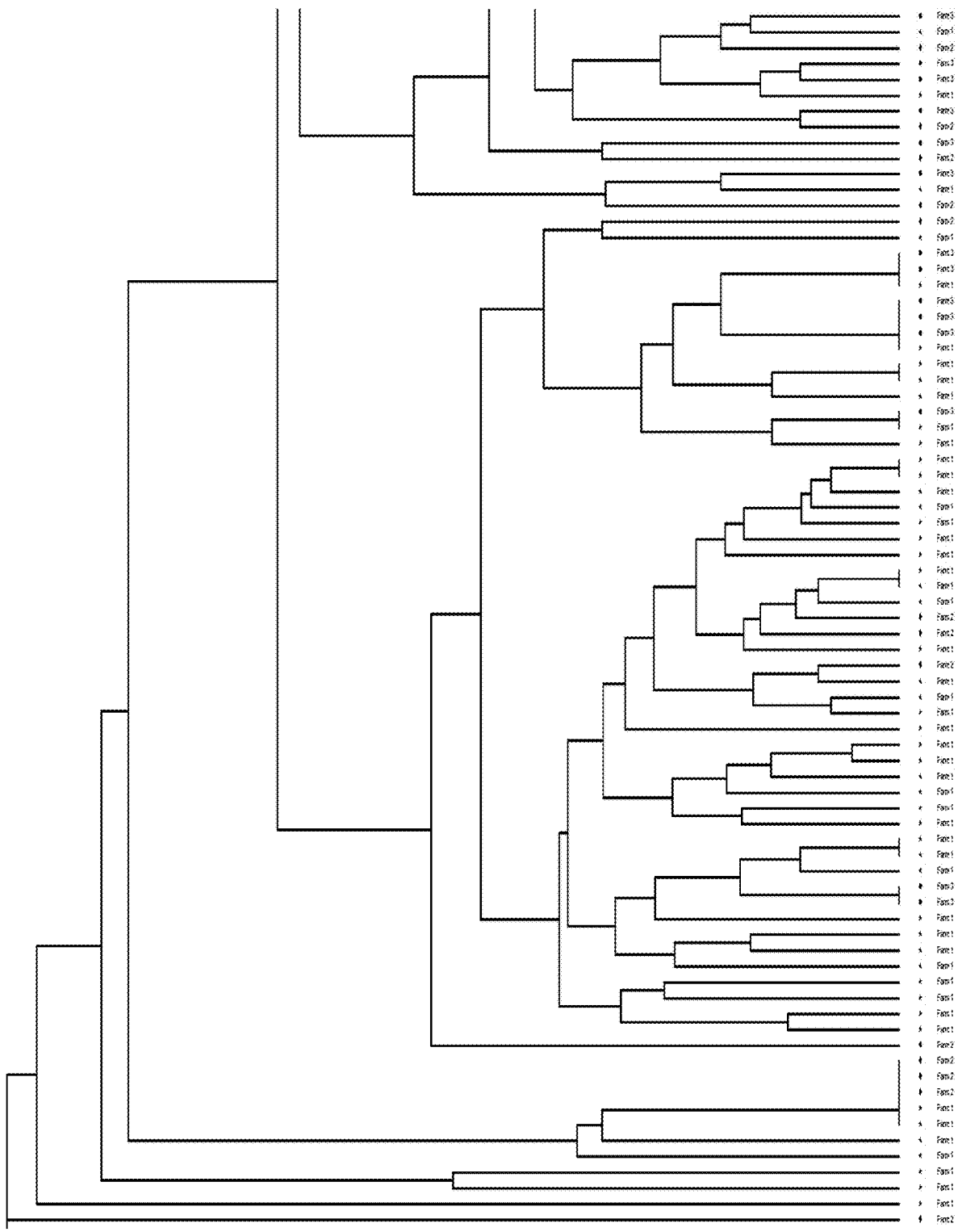

The genetic diversity of the pathogenic *E. coli* isolates obtained from three separate farms is shown in FIG. 1. Evident in this dendrogram, there are several genetically distinct *E. coli* isolates or collections of isolates that are specific to each of the three farms surveyed, whereas there are also several clusters of genetically similar isolates that are represented by two or three of the farms. At total of 107 *E. coli* isolates representing the genetic diversity were screened for growth reduction sensitivity to the *Bacillus* bacteriocins. Three of the six *Bacillus* (747, 1781, and 1999) produced bacteriocins that were highly effective in reducing the growth of the tested *E. coli* diversity as indicated by their ability to reduce *E. coli* growth approximately 90% (Table 2), compared to 55% or less growth reduction by the less effective *Bacillus* strains.

These data illustrate that the genetic diversity of pathogenic *E. coli* is represented by many isolates that are distinct to a specific swine farm. Furthermore, the *E. coli* growth inhibition assay revealed that *B. subtilis* strains varied in their individual efficacy of controlling the growth of pathogenic *E. coli*, indicating the use of strategic combinations of *Bacillus* strain customized to the pathogens specific to an individual farm is warranted.

TABLE 2

Percent growth reduction of pathogenic *E. coli* isolates by commercial *Bacillus* strains.

| E. coli ID | Farm | 747 | 1104 | 1541 | 1781 | 1999 | 2018 |
| --- | --- | --- | --- | --- | --- | --- | --- |
| B90_A08 | Farm 1 | 80.7 | 39.7 | 50.9 | 78.0 | 84.3 | 51.3 |
| B90_C01 | Farm 1 | 99.0 | 79.9 | 93.1 | 99.6 | 99.7 | 88.7 |
| B90_C12 | Farm 1 | 92.6 | 49.4 | 66.7 | 96.3 | 96.7 | 67.7 |
| B90_D10 | Farm 1 | 93.3 | 58.7 | 68.1 | 92.0 | 94.5 | 60.7 |
| B90_E01 | Farm 1 | 87.1 | 48.2 | 60.4 | 91.3 | 94.0 | 53.7 |
| B90_E06 | Farm 1 | 86.7 | 44.3 | 59.3 | 87.1 | 90.1 | 56.5 |
| B90_F01 | Farm 1 | 92.5 | 50.4 | 73.4 | 94.9 | 93.9 | 67.5 |
| B90_F12 | Farm 1 | 91.0 | 42.4 | 59.6 | 84.3 | 87.9 | 51.6 |
| B90_H01 | Farm 1 | 92.8 | 51.4 | 54.0 | 96.5 | 95.7 | 54.5 |
| B93_E02 | Farm 1 | 90.7 | 44.0 | 54.0 | 94.4 | 94.4 | 61.6 |
| B91_A04 | Farm 1 | 86.7 | 53.3 | 57.6 | 95.8 | 95.7 | 71.1 |
| B91_B01 | Farm 1 | 90.9 | 59.5 | 73.3 | 99.2 | 98.9 | 69.3 |
| B91_D07 | Farm 1 | 84.2 | 27.6 | 48.8 | 94.7 | 91.4 | 49.7 |
| B91_G03 | Farm 1 | 98.2 | 52.0 | 40.4 | 97.1 | 98.6 | 51.3 |
| B91_G09 | Farm 1 | 98.7 | 72.8 | 76.5 | 98.0 | 97.6 | 80.9 |
| B91_H02 | Farm 1 | 87.5 | 51.1 | 51.4 | 90.5 | 88.1 | 57.7 |
| B91_H10 | Farm 1 | 91.1 | 39.4 | 48.8 | 92.4 | 89.1 | 61.8 |
| B92_A04 | Farm 1 | 91.7 | 50.4 | 49.0 | 94.7 | 89.0 | 65.6 |
| B92_A03 | Farm 1 | 86.9 | 21.9 | 29.0 | 92.4 | 81.7 | 57.7 |
| B92_B05 | Farm 1 | 82.8 | 38.9 | 34.8 | 83.4 | 76.3 | 52.2 |
| B92_B08 | Farm 1 | 95.2 | 46.2 | 47.1 | 92.4 | 86.8 | 64.5 |
| B92_E01 | Farm 1 | 92.0 | 41.1 | 37.8 | 89.2 | 86.6 | 56.3 |
| B92_F03 | Farm 1 | 98.7 | 59.3 | 58.8 | 95.4 | 94.1 | 57.5 |
| B92_G04 | Farm 1 | 91.4 | 18.8 | 25.0 | 88.2 | 76.0 | 26.4 |
| B93_A03 | Farm 1 | 88.4 | 19.9 | 28.9 | 86.6 | 76.5 | 32.7 |
| B93_B01 | Farm 1 | 94.6 | 55.4 | 67.7 | 97.4 | 90.6 | 71.1 |
| B93_C10 | Farm 1 | 71.3 | 14.5 | 31.4 | 76.3 | 66.1 | 34.4 |
| B93_D04 | Farm 1 | 87.0 | 49.2 | 60.6 | 92.1 | 93.7 | 65.2 |
| B94_B01 | Farm 1 | 87.4 | 44.9 | 39.6 | 84.5 | 90.7 | 47.4 |
| B94_B11 | Farm 1 | 93.9 | 45.1 | 54.3 | 93.5 | 96.9 | 53.6 |
| B94_D02 | Farm 1 | 91.7 | 58.9 | 56.0 | 91.9 | 96.1 | 70.6 |
| B94_D11 | Farm 1 | 83.0 | 48.9 | 40.8 | 85.6 | 93.0 | 41.7 |
| B94_E08 | Farm 1 | 97.5 | 59.1 | 58.9 | 92.0 | 95.9 | 72.3 |
| B94_E11 | Farm 1 | 95.7 | 54.3 | 60.2 | 89.9 | 91.7 | 69.6 |
| B94_G04 | Farm 1 | 95.4 | 39.6 | 46.7 | 89.7 | 91.2 | 49.9 |

TABLE 2-continued

Percent growth reduction of pathogenic *E. coli* isolates by commercial *Bacillus* strains.

| E. coli ID | Farm | 747 | 1104 | 1541 | 1781 | 1999 | 2018 |
|---|---|---|---|---|---|---|---|
| B94_H01 | Farm 1 | 87.9 | 28.7 | 45.7 | 87.3 | 85.9 | 47.1 |
| B94_H05 | Farm 1 | 92.0 | 35.1 | 50.3 | 88.2 | 83.3 | 54.2 |
| B95_A10 | Farm 1 | 73.6 | 16.1 | 23.4 | 80.7 | 75.9 | 43.0 |
| B95_A12 | Farm 1 | 93.1 | 43.9 | 47.6 | 95.1 | 96.6 | 57.5 |
| B95_C01 | Farm 1 | 94.3 | 67.3 | 69.0 | 97.6 | 96.8 | 78.3 |
| B95_D07 | Farm 1 | 92.6 | 48.9 | 61.4 | 97.0 | 94.7 | 63.0 |
| B95_D08 | Farm 1 | 92.9 | 60.5 | 53.6 | 97.9 | 95.9 | 69.9 |
| B95_D12 | Farm 1 | 97.7 | 79.2 | 76.9 | 99.2 | 98.8 | 66.9 |
| B95_E05 | Farm 1 | 96.0 | 54.5 | 67.6 | 97.1 | 96.0 | 62.2 |
| B95_E07 | Farm 1 | 94.7 | 47.6 | 58.4 | 93.1 | 92.6 | 55.9 |
| B95_F03 | Farm 1 | 98.3 | 55.2 | 77.9 | 99.3 | 97.6 | 64.5 |
| B95_G03 | Farm 1 | 82.8 | 24.8 | 22.8 | 86.3 | 76.6 | 28.3 |
| B95_H02 | Farm 1 | 86.7 | 46.8 | 44.7 | 87.0 | 85.7 | 49.7 |
| B95_H05 | Farm 1 | 97.8 | 76.9 | 85.2 | 98.3 | 97.3 | 79.6 |
| B96_A09 | Farm 1 | 86.8 | 30.5 | 40.8 | 90.7 | 86.1 | 44.1 |
| B96_A12 | Farm 1 | 83.7 | 28.8 | 36.1 | 86.8 | 85.3 | 46.6 |
| B96_B01 | Farm 1 | 93.2 | 43.7 | 65.4 | 95.6 | 95.4 | 54.6 |
| B96_C02 | Farm 1 | 79.7 | 38.8 | 47.5 | 90.0 | 90.5 | 55.4 |
| B96_C03 | Farm 1 | 72.7 | 20.8 | 31.2 | 87.7 | 87.0 | 52.6 |
| B96_D09 | Farm 1 | 91.0 | 56.8 | 55.3 | 98.0 | 98.0 | 70.1 |
| B96_E05 | Farm 1 | 85.4 | 24.1 | 41.7 | 81.9 | 75.2 | 48.7 |
| B96_E12 | Farm 1 | 88.7 | 63.4 | 56.2 | 95.6 | 92.1 | 60.6 |
| B96_F08 | Farm 1 | 82.3 | 32.5 | 52.0 | 86.7 | 83.9 | 51.8 |
| B96_G02 | Farm 1 | 91.1 | 33.0 | 54.7 | 91.1 | 95.6 | 52.8 |
| B96_H05 | Farm 1 | 90.7 | 46.3 | 53.9 | 90.2 | 86.3 | 48.5 |
| B97_A12 | Farm 1 | 76.4 | 23.5 | 45.8 | 85.6 | 82.4 | 43.1 |
| B97_B06 | Farm 1 | 98.8 | 48.5 | 70.8 | 99.6 | 99.6 | 55.0 |
| B97_C04 | Farm 1 | 90.7 | 48.5 | 59.9 | 98.6 | 97.2 | 57.5 |
| B97_C06 | Farm 1 | 91.6 | 59.3 | 67.8 | 98.9 | 98.1 | 65.8 |
| B97_C09 | Farm 1 | 86.2 | 49.5 | 50.7 | 95.7 | 95.9 | 42.9 |
| B97_C10 | Farm 1 | 83.1 | 57.0 | 62.7 | 97.2 | 95.0 | 59.8 |
| B97_C11 | Farm 1 | 96.6 | 44.9 | 71.1 | 98.6 | 97.9 | 46.9 |
| B97_D03 | Farm 1 | 96.3 | 43.6 | 50.9 | 95.7 | 94.5 | 53.9 |
| B128_A09 | Farm 1 | 99.8 | 53.1 | 61.2 | 99.9 | N/A | 65.4 |
| B128_A10 | Farm 1 | 99.8 | 52.7 | 57.3 | 99.8 | N/A | 73.0 |
| B128_A11 | Farm 1 | 99.0 | 41.3 | 26.8 | 99.4 | N/A | 53.2 |
| B126_D11 | Farm 1 | 99.3 | 51.4 | 43.7 | 99.3 | N/A | 49.5 |
| B126_E10 | Farm 1 | 98.4 | 66.3 | 58.9 | 99.2 | N/A | 67.2 |
| B127_E12 | Farm 1 | 98.6 | 50.6 | 53.7 | 99.5 | N/A | 63.2 |
| B127_E11 | Farm 1 | 65.1 | 28.4 | 30.7 | 62.9 | N/A | 40.4 |
| B105_A10 | Farm 2 | 100.0 | 100.0 | 100.0 | 100.0 | 100.0 | 100.0 |
| B105_B10 | Farm 2 | 100.0 | 89.0 | 100.0 | 100.0 | 100.0 | 99.7 |
| B116_D01 | Farm 2 | 89.1 | 56.9 | 56.7 | 91.2 | 92.2 | 45.4 |
| B116_D02 | Farm 2 | 86.2 | 43.8 | 68.5 | 94.3 | 91.3 | 49.0 |
| B116_D03 | Farm 2 | 87.1 | 45.5 | 65.5 | 95.3 | 93.1 | 48.1 |
| B116_D04 | Farm 2 | 86.9 | 45.2 | 68.6 | 93.6 | 91.8 | 52.9 |
| B116_D06 | Farm 2 | 69.2 | 53.5 | 57.3 | 97.1 | 97.4 | 56.0 |
| B116_D07 | Farm 2 | 63.0 | 45.6 | 47.8 | 97.5 | 94.3 | 61.1 |
| B116_D08 | Farm 2 | 76.8 | 35.4 | 48.3 | 94.3 | 90.1 | 47.0 |
| B116_D11 | Farm 2 | 80.2 | 10.9 | 49.6 | 90.0 | 86.6 | 20.7 |
| B116_D12 | Farm 2 | 90.3 | 48.6 | 52.2 | 87.3 | 90.0 | 22.8 |
| B116_E01 | Farm 2 | 90.4 | 46.1 | 65.6 | 92.8 | 94.2 | 46.9 |
| B116_E02 | Farm 2 | 85.1 | 30.7 | 56.4 | 88.1 | 91.1 | 32.0 |
| B116_E03 | Farm 2 | 84.1 | 37.6 | 55.0 | 91.6 | 89.5 | 38.6 |
| B116_E04 | Farm 2 | 74.3 | 27.0 | 54.8 | 90.1 | 90.7 | 26.5 |
| B117_E08 | Farm 2 | 69.8 | 14.7 | 37.2 | 86.7 | 72.5 | 23.3 |
| B117_E09 | Farm 2 | 68.6 | 19.5 | 42.8 | 83.1 | 72.1 | 22.7 |
| B117_E10 | Farm 2 | 78.1 | 13.6 | 37.7 | 89.7 | 86.6 | 19.4 |
| B117_E11 | Farm 2 | 76.2 | 28.0 | 56.1 | 84.1 | 82.4 | 28.2 |
| B117_E12 | Farm 2 | 76.1 | 28.2 | 49.0 | 84.2 | 75.6 | 24.8 |
| B117_F04 | Farm 2 | 82.7 | 24.2 | 45.7 | 80.1 | 74.0 | 23.1 |
| B117_F07 | Farm 2 | 75.1 | 24.1 | 42.6 | 81.8 | 72.7 | 21.2 |
| B117_F09 | Farm 2 | 77.6 | 22.9 | 45.9 | 87.5 | 71.4 | 27.4 |
| B117_F10 | Farm 2 | 72.7 | 15.7 | 47.4 | 82.8 | 75.6 | 28.6 |
| B117_F11 | Farm 2 | 67.4 | 21.7 | 47.8 | 84.4 | 76.5 | 20.1 |
| B117_F12 | Farm 2 | 79.0 | 16.1 | 52.0 | 88.4 | 86.8 | 24.8 |
| B117_G12 | Farm 2 | 100.0 | 55.4 | 96.2 | 100.0 | 100.0 | 54.0 |
| B118_A10 | Farm 2 | 100.0 | 40.8 | 85.2 | 100.0 | 100.0 | 63.6 |
| B118_C12 | Farm 2 | 93.3 | 19.4 | 46.6 | 97.5 | 93.3 | 42.0 |
| B118_D06 | Farm 2 | 91.7 | 24.6 | 58.2 | 98.0 | 95.4 | 42.6 |
| B134_A03 | Farm 2 | 99.1 | 89.5 | 99.2 | 100.0 | 99.6 | 55.6 |
| B134_A04 | Farm 2 | 98.2 | 89.0 | 97.9 | 97.1 | 99.7 | 52.3 |

TABLE 2-continued

Percent growth reduction of pathogenic *E. coli* isolates by commercial *Bacillus* strains.

| E. coli ID | Farm | 747 | 1104 | 1541 | 1781 | 1999 | 2018 |
|---|---|---|---|---|---|---|---|
| B134_B11 | Farm 2 | 98.9 | 77.4 | 83.6 | 99.1 | 99.2 | 75.4 |
| B134_B12 | Farm 2 | 98.0 | 65.9 | 93.5 | 99.4 | 99.0 | 66.1 |
| B134_C01 | Farm 2 | 98.4 | 53.1 | 61.9 | 39.8 | 52.7 | 58.8 |
| B134_E03 | Farm 2 | 97.5 | 43.8 | 68.0 | 88.8 | 96.4 | 30.5 |
| B134_E07 | Farm 2 | 98.9 | 70.2 | 56.2 | 79.5 | 84.6 | 53.6 |
| B135_B10 | Farm 2 | 98.8 | 69.7 | 64.3 | 98.6 | 98.1 | 69.5 |
| B100_A03 | Farm 3 | 73.0 | 0.0 | 8.5 | 55.8 | 56.3 | 14.8 |
| B100_A12 | Farm 3 | 98.3 | 15.4 | 41.2 | 96.4 | 94.8 | 35.8 |
| B100_B02 | Farm 3 | 94.4 | 14.1 | 30.5 | 92.7 | 93.1 | 31.2 |
| B100_B04 | Farm 3 | 71.0 | 0.0 | 10.8 | 56.9 | 61.7 | 21.2 |
| B100_B05 | Farm 3 | 95.9 | 15.5 | 51.7 | 89.9 | 91.1 | 32.7 |
| B99_A07 | Farm 3 | 98.4 | 30.9 | 59.4 | 97.4 | 97.4 | 26.0 |
| B99_A10 | Farm 3 | 95.5 | 13.3 | 59.5 | 95.2 | 95.4 | 29.2 |
| B99_A12 | Farm 3 | 96.3 | 0.0 | 51.2 | 94.5 | 93.7 | 16.2 |
| B99_C09 | Farm 3 | 99.9 | 35.9 | 67.1 | 99.9 | 100.0 | 67.7 |
| B99_C11 | Farm 3 | 99.5 | 28.6 | 63.3 | 99.5 | 99.1 | 53.8 |
| B99_D02 | Farm 3 | 99.4 | 27.6 | 51.9 | 99.3 | 99.4 | 59.7 |
| B99_E08 | Farm 3 | 83.2 | 15.7 | 21.6 | 78.2 | 78.9 | 24.8 |
| B99_F07 | Farm 3 | 96.3 | 22.1 | 36.1 | 94.4 | 93.7 | 27.4 |
| B99_F09 | Farm 3 | 96.1 | 14.9 | 46.0 | 94.5 | 94.7 | 26.2 |
| B99_H03 | Farm 3 | 99.4 | 25.9 | 59.7 | 98.0 | 98.6 | 61.0 |
| B99_H05 | Farm 3 | 99.4 | 28.4 | 74.3 | 99.6 | 99.4 | 70.4 |
| B99_H08 | Farm 3 | 99.5 | 14.5 | 63.1 | 98.9 | 99.5 | 29.8 |
| B99_H10 | Farm 3 | 97.6 | 9.4 | 56.3 | 93.4 | 94.3 | 30.2 |
| B102_E07 | Farm 3 | 99.4 | 28.0 | 72.2 | 99.5 | 99.5 | 81.8 |
| B102_E10 | Farm 3 | 94.8 | 5.8 | 21.5 | 91.6 | 91.0 | 27.5 |
| B102_F01 | Farm 3 | 93.9 | 12.3 | 42.6 | 93.1 | 92.9 | 23.9 |
| B102_F04 | Farm 3 | 97.2 | 14.7 | 30.4 | 96.5 | 95.3 | 34.4 |
| B102_H06 | Farm 3 | 99.3 | 29.7 | 75.7 | 99.5 | 99.4 | 78.6 |
| B103_B08 | Farm 3 | 93.4 | 12.6 | 45.5 | 96.0 | 92.4 | 28.4 |
| B103_C07 | Farm 3 | 92.1 | 8.0 | 21.8 | 90.0 | 87.0 | 26.1 |
| B103_C11 | Farm 3 | 99.4 | 27.3 | 70.9 | 99.3 | 99.1 | 77.0 |
| B103_D07 | Farm 3 | 99.5 | 25.8 | 64.6 | 99.3 | 99.3 | 68.4 |
| B103_D08 | Farm 3 | 96.8 | 8.8 | 57.2 | 95.5 | 96.6 | 29.1 |
| B103_E10 | Farm 3 | 99.4 | 27.2 | 60.5 | 99.4 | 99.4 | 71.9 |
| B103_F05 | Farm 3 | 98.2 | 27.7 | 48.1 | 77.7 | 88.6 | 68.2 |
| B103_F10 | Farm 3 | 97.5 | 20.4 | 63.2 | 96.7 | 94.8 | 51.5 |
| B100_B08 | Farm 3 | 97.2 | 16.5 | 51.4 | 92.2 | 91.1 | 31.6 |
| B100_B12 | Farm 3 | 97.9 | 15.7 | 51.4 | 93.0 | 93.7 | 31.5 |
| B100_C03 | Farm 3 | 89.9 | 13.9 | 34.0 | 80.7 | 78.1 | 32.6 |
| B100_D01 | Farm 3 | 85.4 | 14.6 | 35.3 | 80.7 | 80.2 | 33.0 |
| B100_D03 | Farm 3 | 96.2 | 14.6 | 56.9 | 94.4 | 93.3 | 27.0 |
| B100_E01 | Farm 3 | 96.9 | 17.7 | 46.7 | 93.2 | 94.3 | 29.6 |
| B100_E03 | Farm 3 | 98.1 | 13.6 | 59.4 | 94.1 | 95.2 | 33.7 |
| B100_G03 | Farm 3 | 95.8 | 13.4 | 51.9 | 94.0 | 94.4 | 33.6 |
| B100_G07 | Farm 3 | 96.8 | 14.5 | 70.2 | 93.8 | 94.8 | 33.8 |
| B100_G09 | Farm 3 | 97.2 | 14.9 | 64.6 | 94.3 | 93.4 | 34.3 |
| B100_H01 | Farm 3 | 96.8 | 14.6 | 67.1 | 93.2 | 93.9 | 35.2 |
| B100_H03 | Farm 3 | 96.1 | 14.6 | 59.7 | 90.5 | 92.5 | 30.6 |
| B101_A01 | Farm 3 | 95.9 | 11.9 | 52.7 | 93.3 | 94.0 | 27.0 |
| B101_A04 | Farm 3 | 97.7 | 2.7 | 66.9 | 95.9 | 95.8 | 19.0 |
| B101_A06 | Farm 3 | 97.1 | 13.3 | 65.3 | 94.7 | 94.6 | 30.4 |
| B101_D01 | Farm 3 | 98.1 | 14.9 | 64.1 | 95.1 | 95.9 | 30.1 |
| B101_D06 | Farm 3 | 96.5 | 0.0 | 67.1 | 96.3 | 95.6 | 59.4 |
| B101_E03 | Farm 3 | 87.9 | 9.7 | 23.8 | 84.3 | 82.3 | 27.5 |
| B101_E11 | Farm 3 | 86.3 | 8.3 | 22.5 | 82.8 | 78.5 | 28.5 |
| B101_F04 | Farm 3 | 87.5 | 12.0 | 26.9 | 88.0 | 88.9 | 30.1 |
| B101_F11 | Farm 3 | 95.6 | 11.7 | 54.1 | 92.0 | 91.8 | 61.9 |
| B101_G04 | Farm 3 | 95.6 | 11.7 | 51.6 | 94.7 | 94.1 | 29.0 |
| B101_G10 | Farm 3 | 95.4 | 13.1 | 55.3 | 94.1 | 93.3 | 31.4 |
| B101_H04 | Farm 3 | 98.3 | 7.7 | 42.6 | 96.6 | 96.1 | 47.1 |
| B101_H09 | Farm 3 | 94.6 | 12.6 | 47.9 | 95.5 | 93.9 | 28.6 |
| B123_C09 | Farm 3 | 95.6 | 37.7 | 42.7 | 83.0 | 61.1 | 33.6 |
| B125_D05 | Farm 3 | 95.2 | 47.8 | 53.1 | 84.2 | 63.4 | 52.4 |
| B125_D06 | Farm 3 | 94.8 | 53.0 | 53.2 | 68.2 | 60.8 | 50.7 |
| B125_D07 | Farm 3 | 97.5 | 53.0 | 51.6 | 90.3 | 58.8 | 46.8 |
| B125_D08 | Farm 3 | 95.9 | 54.4 | 55.9 | 88.5 | 54.3 | 55.8 |
| B125_D09 | Farm 3 | 95.0 | 58.2 | 62.3 | 73.2 | 57.4 | 51.3 |
| B125_D10 | Farm 3 | 98.6 | 40.9 | 52.4 | 71.4 | 54.0 | 39.0 |
| Average (%) reduction | | 91.1% | 35.9% | 54.2% | 91.4% | 89.4% | 48.0% |

Example 2: Genetic Diversity of Pathogenic
*Clostridium perfringens* Type a on Commercial
Swine Farms and In Vitro Inhibition of Clostridial
Growth by Distinct *Bacillus subtilis* Isolates Pathogenic *C. perfringens* isolates can have varied susceptibility to the bacteriocins produced by different *B. subtilis* strains. By isolating pathogenic *Clostridia* isolates from swine at a particular farm/location and selecting a diverse set of representatives, the bacteriocins from multiple *Bacillus* strains can be tested for their effectiveness inhibiting the growth of the pathogens present.

*Clostridium* isolates were cultured from swine sources (fecal material or gastrointestinal tissue) on Tryptose Sulfite Cycloserine (TSC) agar and grown anaerobically at 37° C. for 24 h. Presumptive *Clostridium* colonies were picked Reinforced Clostridial Medium (RCM) and incubated anaerobically at 37° C. for 24 h. Genomic DNA (gDNA) was extracted from the overnight culture using the same methods previously described in Example 1. Pathogenic *C. perfringens* were identified in the overnight culture by a multiplex PCR screen using primers specific to 4 toxin gene targets (Table 3). The multiplex PCR reaction mixture included: 2 µL 10× PCR Buffer, 0.4 µL of 10 mM dNTP mix, 1.2 µL 50 mM MgCl$_2$, 1 µL of each of the 8 primers (4 sets of Forward & Reverse primers), 13.2 µL of sterile water, 0.08 µL Platinum Taq (Invitrogen), and 2 µL template gDNA (final volume=20 µL). The PCR cycles were set at: an initial 5 minutes at 94° C., then 30 cycles of 1 min at 94° C., 1 min at 55° C., and 1 min at 72° C. Samples were run on a fragment analyzer (Advanced Analytics Technologies) to visualize amplification products. Isolates that tested positive for any one target gene were considered pathogenic.

TABLE 3

Primers used in pathogenic *C. perfringens* screen

| Primer | Sequence | SEQ ID NO |
|---|---|---|
| CPA-F | GTTGATAGCGCAGGACATGTTAAG | 19 |
| CPA-R | CATGTAGTCATCTGTTCCAGCATC | 20 |
| CPB-F | ACTATACAGACAGATCATTCAACC | 21 |
| CPB-R | TTAGGAGCAGTTAGAACTACAGAC | 22 |
| CPE-F | ACTGCAACTACTACTCATACTGTG | 23 |
| CPE-R | CTGGTGCCTTAATAGAAAGACTCC | 24 |
| CPI-F | GCGATGAAAAGCCTACACCACTAC | 25 |
| CPI-R | GGTATATCCTCCACGCATATAGTC | 26 |

The genetic diversity of the identified pathogenic *C. perfringens* was determined by obtaining randomly amplified polymorphic DNA (RAPD) profiles for each isolate. The PCR reaction included: 5 µL gDNA, 2.5 µL RAPD primer 2 (10 µM) [GTTTCGCTCC, SEQ ID NO: 27], and 17.5 µL nuclease free water added to a GE RAPD bead tube (GE Healthcare). The PCR temperature cycle was as follows: an initial 5 min at 95° C., then 45 cycles of 1 min at 95° C., 1 min at 36° C., 2 min at 72° C., and finally 5 min at 72° C. Samples were run on a fragment analyzer (Advanced Analytics Technologies) and RAPD profiles were used to compile a dendrogram of genetic similarity using BioNumerics software (Applied Maths).

Toxigenic *C. perfringens* isolates were stored at −80° C. prior to growing on Tryptose Sulfite Cycloserine (TSC) agar containing 100 mg/mL of D-cycloserine. The plates were incubated at 37° C. in anaerobic conditions (anaerobic chamber with two Pack—Anaero) for 24 hours. A single colony was picked from the TSC plate and transferred to a 96 deep well block containing 500 µL of Reinforced Clostridial Media (RCM). *Clostridium* isolates were incubated at 37° C. in anaerobic conditions for 6-24 hrs. After incubation, the *Clostridium* isolates were diluted by transferring 10 µL of the overnight culture to 190 µL of Brain Heart Infusion broth with 0.5 g/L of L-cysteine (BHI+). *Bacillus* bacteriocin from a panel of six *B. subtilis* strains was diluted by adding 170 µL of BHI+ broth to 30 µL of the respective *Bacillus* strain bacteriocin (747, 1104, 1541, 1781, 1999, and 2018).

Each diluted *Clostridium* isolate was assayed in duplicate against the prepared bacteriocin from each of the six *Bacillus* strains. Briefly, the assay design included a positive control containing 195 µL of BHI+ and 5 µL of the diluted *C. perfringens* cell culture, the negative control contained 195 µL of BHI+ only, and the bacteriocin test wells contained 5 µL of the diluted *C. perfringens* culture and 195 µL of the respective bacteriocin from each of the six *Bacillus* strains. Plates were placed at 37° C. incubator for 18 hours and optical density was determined by reading on a Biotek Epoch Microplate Spectrometer at 600 nm wavelength. The following formula was used to determine the percent growth reduction of the *C. perfringens* culture by the *Bacillus* bacteriocin: (1−((pure culture isolate−neg. control)/(pos. control−neg. control)))×100, and this value was used to determine the best formulation of *Bacillus* strains to include in a customized product to control a specific farm's pathogenic *Clostridium*.

Figure 2A:
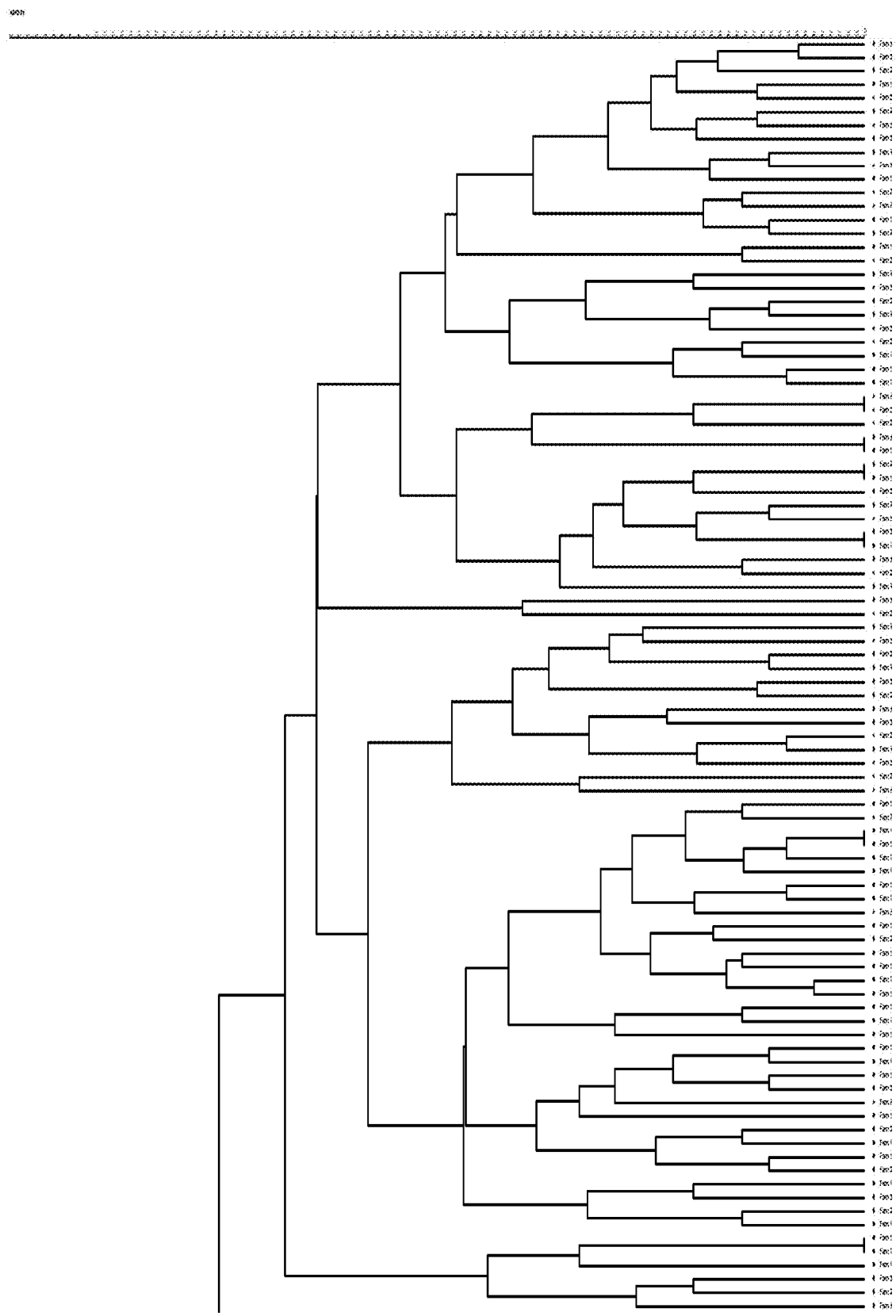
FIGS. 2A and 2B depict a graph showing a dendrogram of the genetic diversity of pathogenic *Clostridium perfringens* isolated from pigs.
Figure 2B:
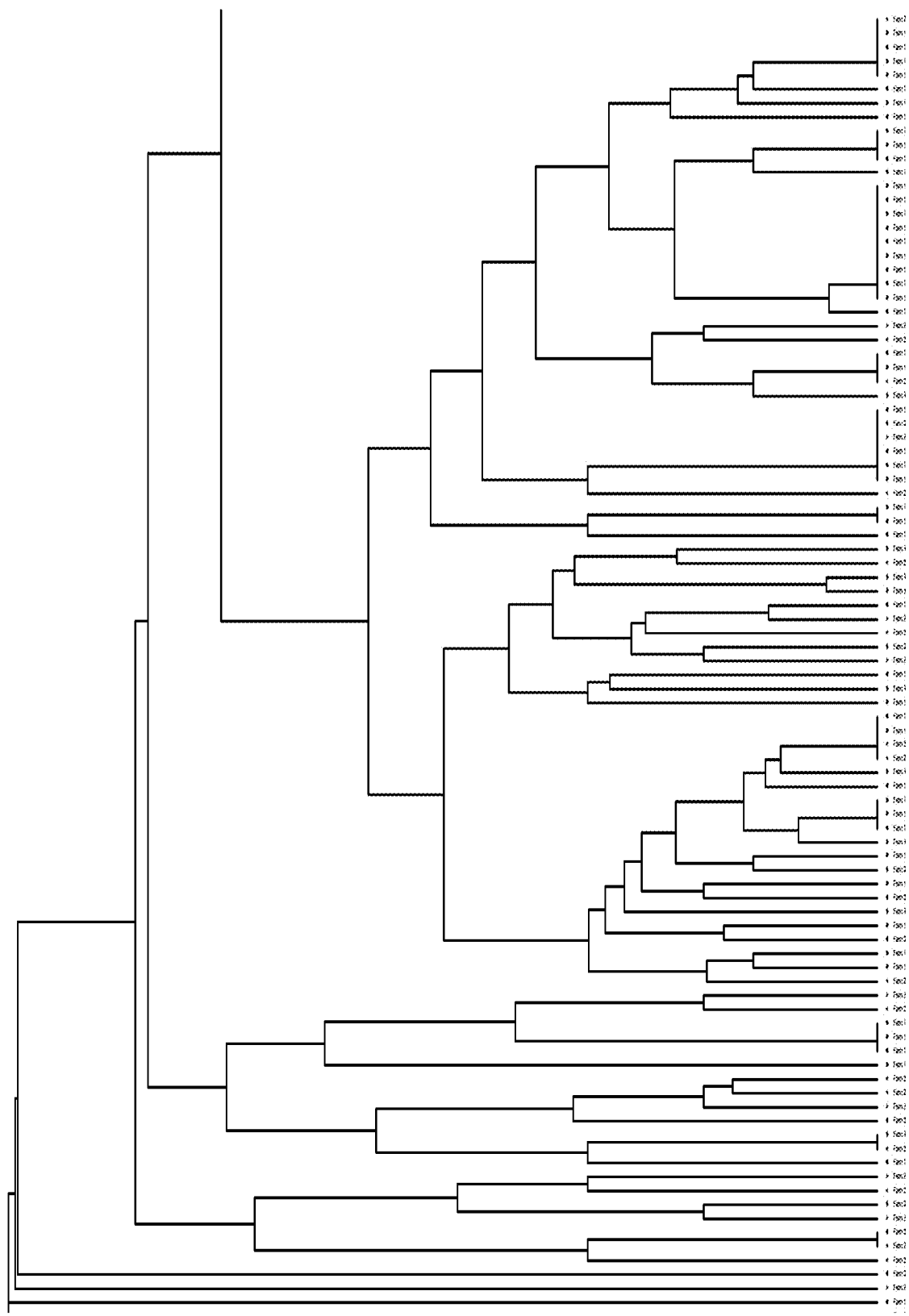
Figure 3A:
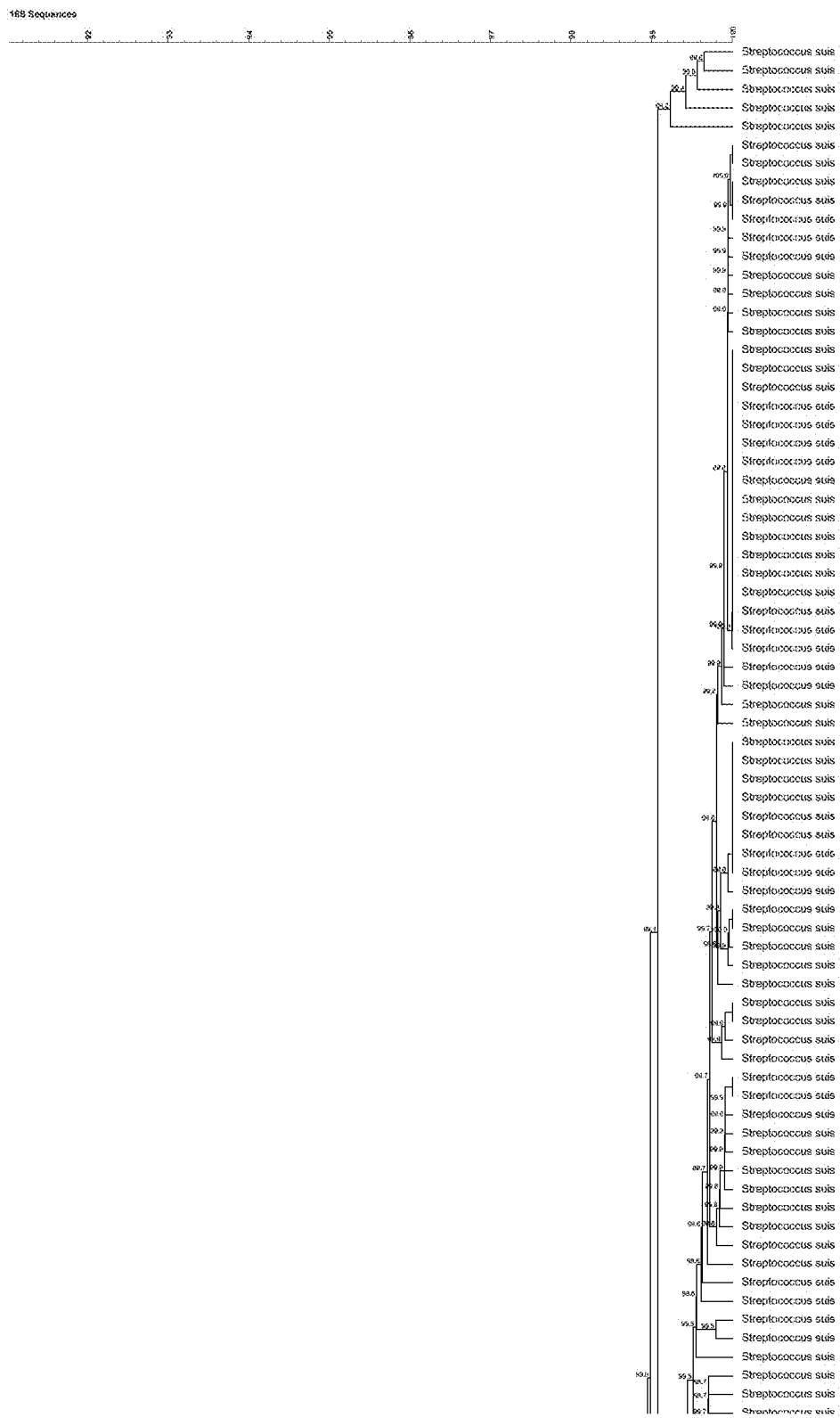
FIGS. 3A, 3B, 3C, and 3D depict a graph showing a dendrogram of the genetic diversity of *Streptococcus* sp isolated from pigs.
Figure 3B:
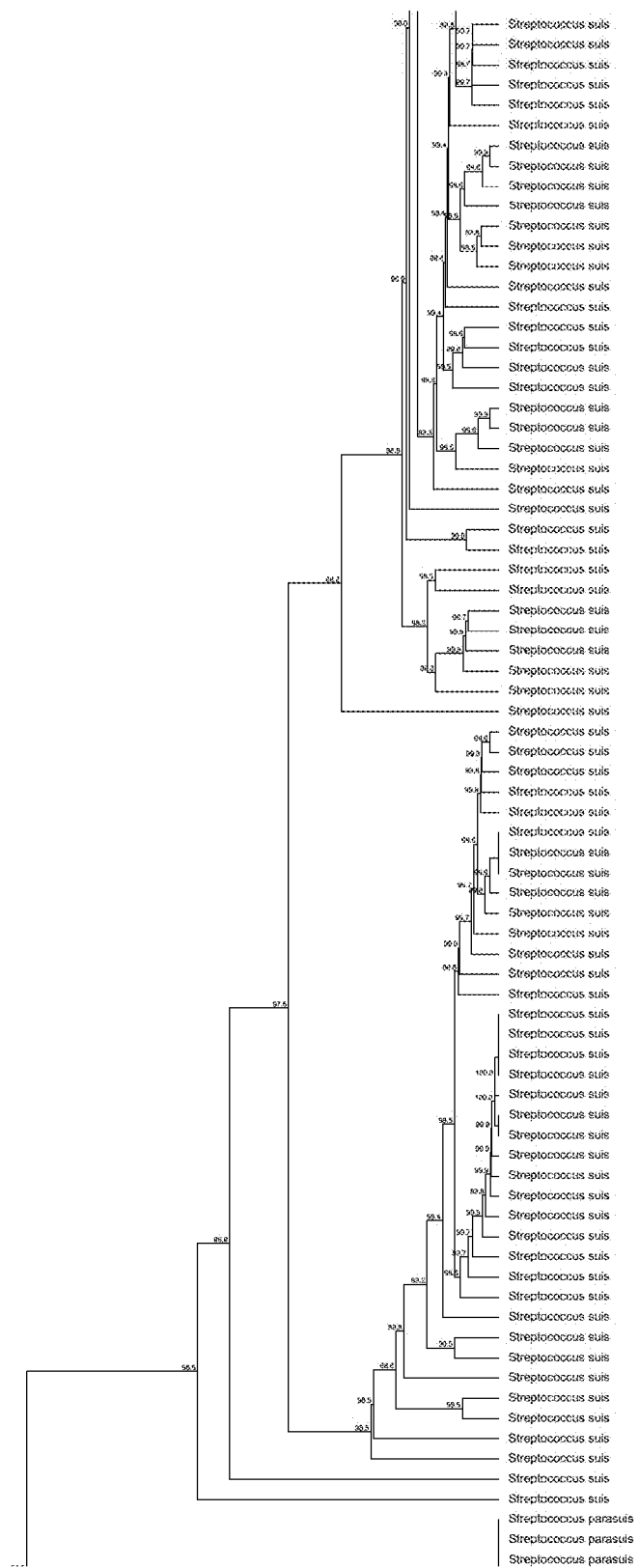
Figure 3C:
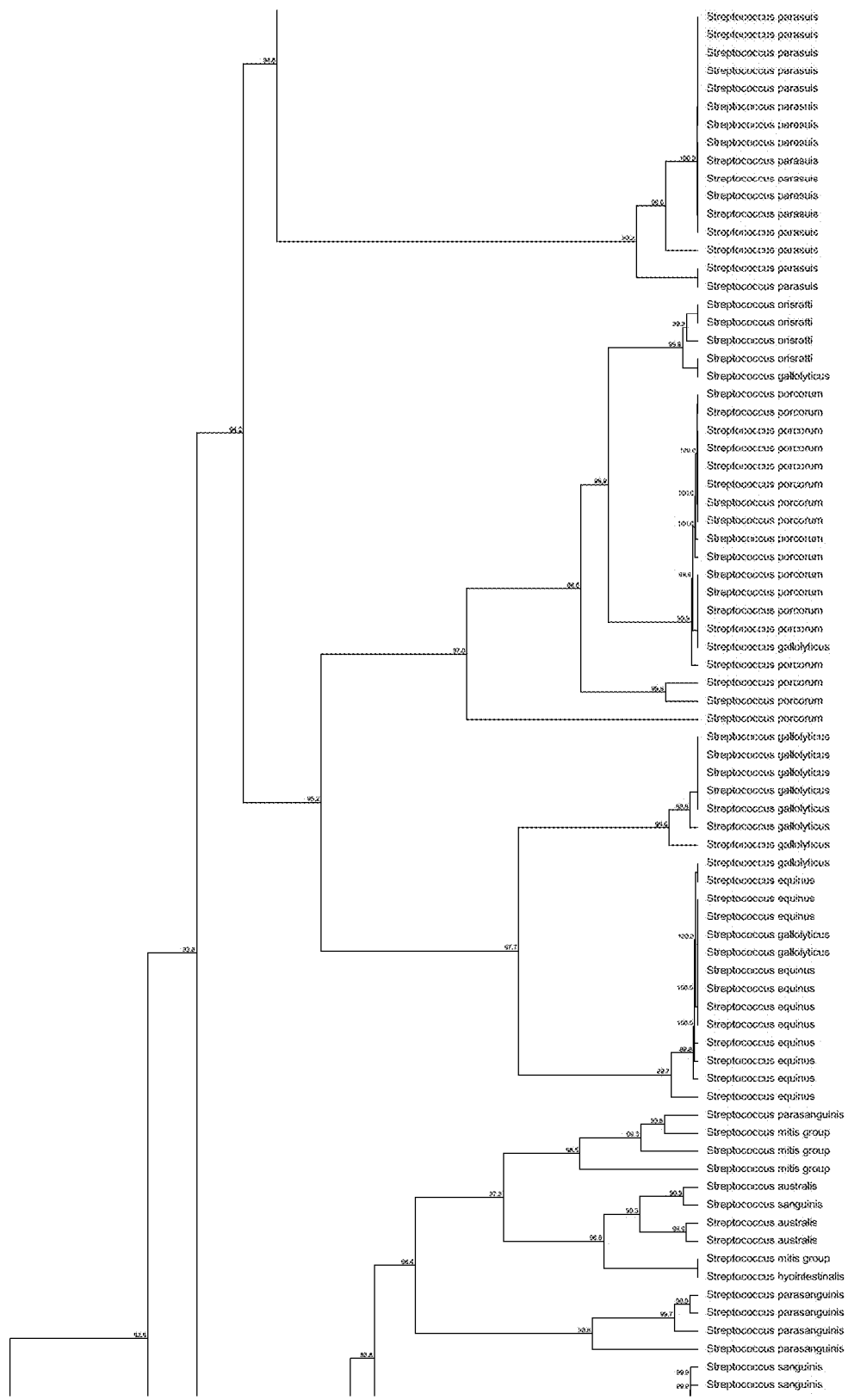
Figure 3D:
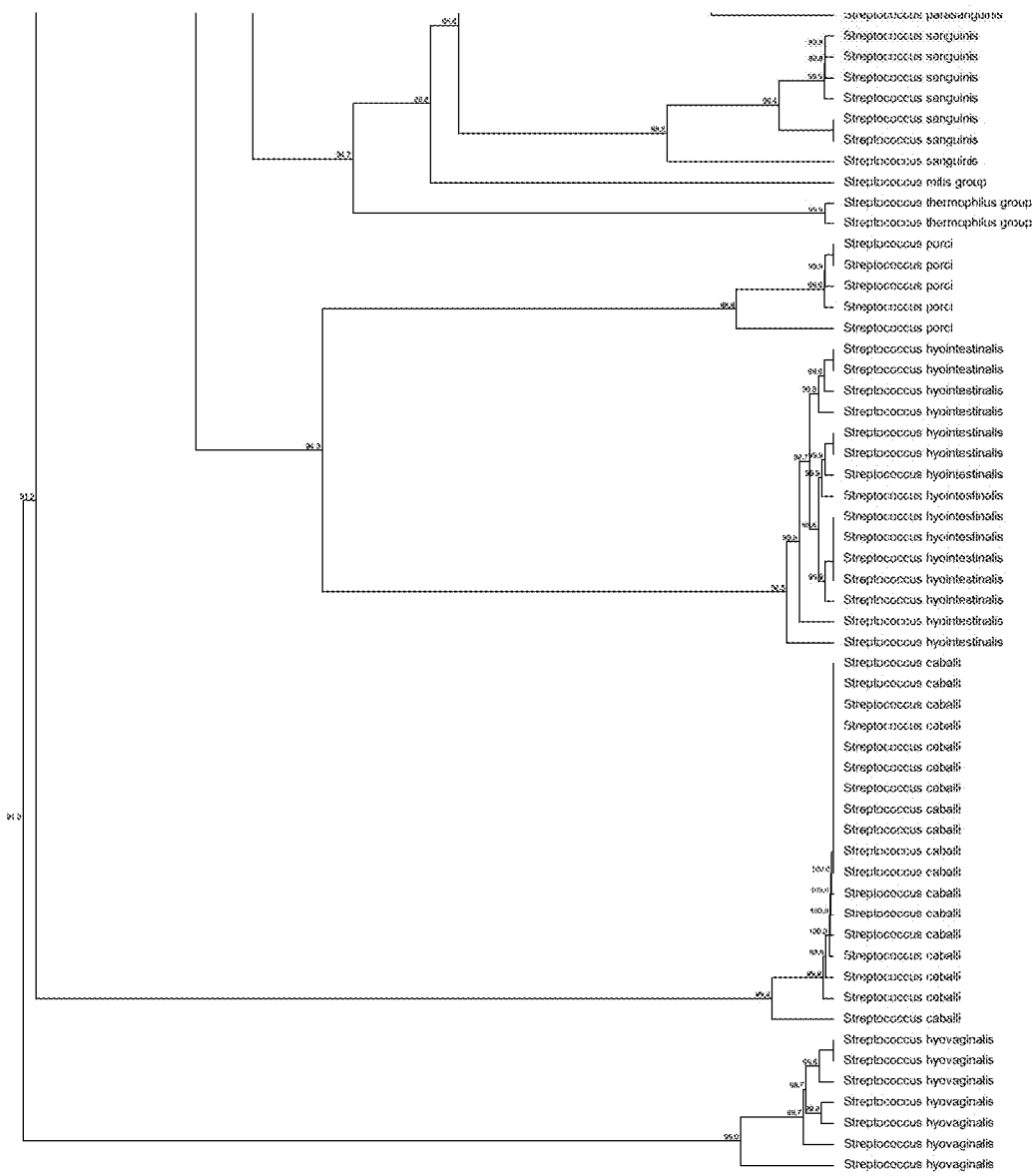
Figure 4:
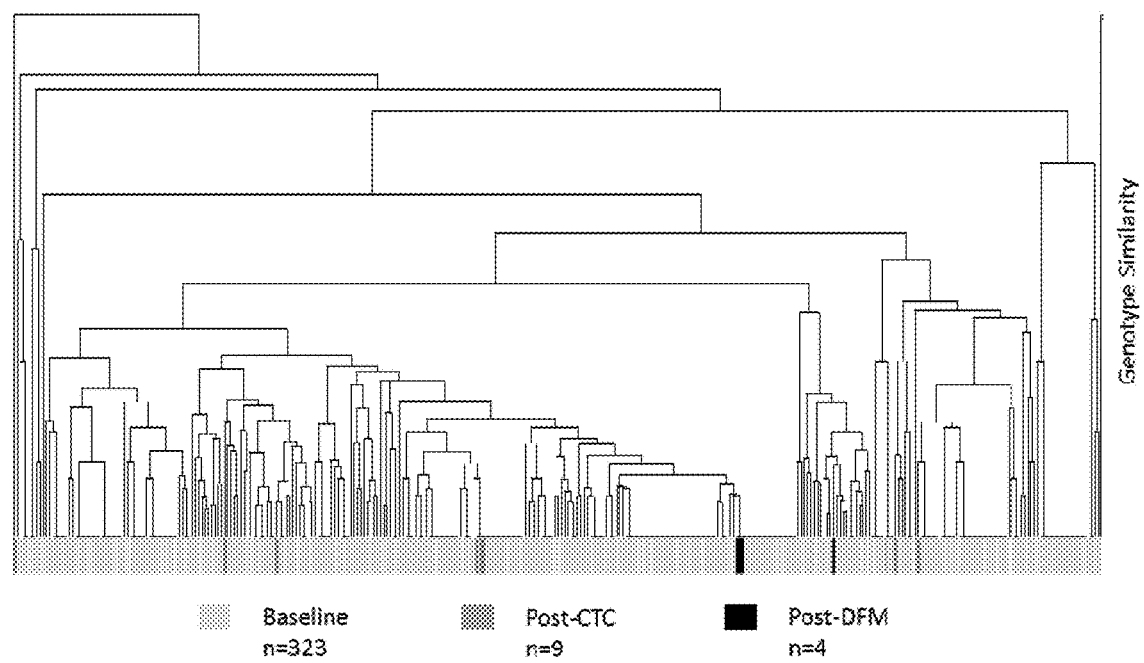
FIG. 4 is a graph showing *E. coli* diversity in pigs at baseline, post-CTC, Post-DFM administration.
Figure 5:
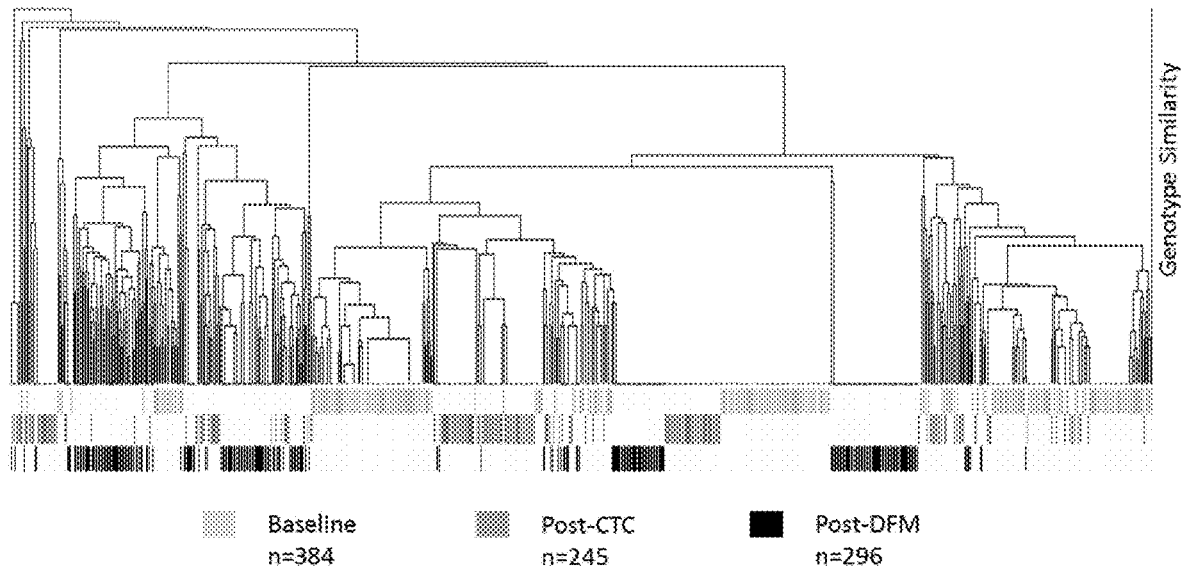
FIG. 5 is a graph showing *Clostridia* populations in pigs at baseline, post-CTC, post-DFM administration.

The genetic diversity of the *C. perfringens* isolates obtained from three separate swine farms is shown in FIG. 2. Evident in this dendrogram, there are several genetically distinct *C. perfringens* isolates and collections of isolates that are specific to each of the three farms surveyed, whereas there are also several clusters of genetically similar isolates that originated from two or three of the farms. A total of 194 *C. perfringens* isolates representing the genetic diversity were screened for growth reduction sensitivity to the *Bacillus* bacteriocins. All six of the *Bacillus* produced bacteriocins that were highly effective in reducing the growth of the tested *C. perfringens* diversity, as indicated by their ability to reduce clostridial growth by >90% over the control (Table 4). These data illustrate that the genetic diversity of *C. perfringens* is represented by many isolates that are distinct to a specific swine farm. Furthermore, the *Clostridium* growth inhibition assay revealed that *B. subtilis* strains are effective at controlling the growth of *Clostridium*.

TABLE 4

Percent growth reduction of *Clostridium perfringens* isolates by commercial *Bacillus* strains.

| Clostridium ID | Farm | 747 | 1104 | 1541 | 1781 | 1999 | 2018 |
|---|---|---|---|---|---|---|---|
| B36_A12 | Farm 1 | 100.0 | 100.0 | 99.9 | 99.5 | 99.8 | 99.8 |
| B36_B08 | Farm 1 | 100.0 | 100.0 | 100.0 | 100.0 | 100.0 | 100.0 |
| B36_E12 | Farm 1 | 100.0 | 100.0 | 100.0 | 100.0 | 98.0 | 100.0 |
| B36_G05 | Farm 1 | 100.0 | 100.0 | 100.0 | 100.0 | 100.0 | 100.0 |
| B36_G08 | Farm 1 | 100.0 | 98.9 | 100.0 | 100.0 | 100.0 | 100.0 |
| B36_H03 | Farm 1 | 100.0 | 100.0 | 100.0 | 100.0 | 100.0 | 90.9 |
| B36_H04 | Farm 1 | 100.0 | 100.0 | 100.0 | 100.0 | 100.0 | 99.5 |
| B36_H05 | Farm 1 | 100.0 | 100.0 | 100.0 | 100.0 | 100.0 | 100.0 |
| B37_A11 | Farm 1 | 100.0 | 99.3 | 100.0 | 100.0 | 100.0 | 100.0 |
| B37_C05 | Farm 1 | 100.0 | 100.0 | 100.0 | 100.0 | 100.0 | 100.0 |
| B37_D04 | Farm 1 | 100.0 | 99.2 | 100.0 | 100.0 | 100.0 | 100.0 |
| B37_D10 | Farm 1 | 99.5 | 100.0 | 100.0 | 100.0 | 100.0 | 99.6 |
| B37_F08 | Farm 1 | 100.0 | 99.3 | 100.0 | 98.9 | 100.0 | 89.8 |
| B37_F10 | Farm 1 | 100.0 | 100.0 | 100.0 | 100.0 | 100.0 | 100.0 |
| B37_G06 | Farm 1 | 0.0 | 0.0 | 0.0 | 0.0 | 0.0 | 4.2 |
| B38_B03 | Farm 1 | 100.0 | 100.0 | 100.0 | 100.0 | 100.0 | 100.0 |
| B38_B07 | Farm 1 | 99.2 | 99.9 | 99.9 | 99.7 | 99.7 | 99.6 |
| B38_B08 | Farm 1 | 100.0 | 100.0 | 100.0 | 100.0 | 100.0 | 100.0 |
| B38_B10 | Farm 1 | 100.0 | 100.0 | 100.0 | 100.0 | 100.0 | 100.0 |
| B38_C02 | Farm 1 | 100.0 | 100.0 | 100.0 | 100.0 | 100.0 | 98.1 |
| B38_C06 | Farm 1 | 100.0 | 100.0 | 99.7 | 100.0 | 100.0 | 100.0 |
| B38_C09 | Farm 1 | 44.0 | 35.6 | 37.0 | 36.1 | 38.8 | 37.2 |
| B38_D01 | Farm 1 | 100.0 | 100.0 | 100.0 | 100.0 | 100.0 | 100.0 |
| B38_D11 | Farm 1 | 100.0 | 99.9 | 99.8 | 99.8 | 99.8 | 99.8 |
| B38_E08 | Farm 1 | 100.0 | 100.0 | 100.0 | 100.0 | 100.0 | 100.0 |
| B38_F10 | Farm 1 | 100.0 | 100.0 | 100.0 | 100.0 | 100.0 | 100.0 |
| B39_A02 | Farm 1 | 100.0 | 100.0 | 100.0 | 100.0 | 100.0 | 100.0 |
| B39_C11 | Farm 1 | 100.0 | 100.0 | 100.0 | 100.0 | 100.0 | 100.0 |
| B39_D05 | Farm 1 | 100.0 | 100.0 | 100.0 | 100.0 | 100.0 | 100.0 |
| B39_D06 | Farm 1 | 91.5 | 92.5 | 89.9 | 94.4 | 90.4 | 98.2 |
| B39_D12 | Farm 1 | 100.0 | 100.0 | 100.0 | 100.0 | 99.2 | 98.2 |
| B39_E02 | Farm 1 | 100.0 | 100.0 | 100.0 | 99.5 | 100.0 | 100.0 |
| B39_E07 | Farm 1 | 44.4 | 12.8 | 35.3 | 44.2 | 46.5 | 30.7 |
| B39_E12 | Farm 1 | 100.0 | 100.0 | 100.0 | 100.0 | 100.0 | 99.5 |
| B39_F07 | Farm 1 | 100.0 | 100.0 | 100.0 | 100.0 | 100.0 | 100.0 |
| B39_G04 | Farm 1 | 100.0 | 99.9 | 100.0 | 100.0 | 100.0 | 100.0 |
| B39_H06 | Farm 1 | 100.0 | 100.0 | 100.0 | 100.0 | 100.0 | 100.0 |
| B40_A09 | Farm 1 | 100.0 | 100.0 | 100.0 | 100.0 | 100.0 | 100.0 |
| B40_B01 | Farm 1 | 100.0 | 100.0 | 100.0 | 100.0 | 100.0 | 100.0 |
| B40_C01 | Farm 1 | 100.0 | 100.0 | 100.0 | 100.0 | 100.0 | 100.0 |
| B40_C03 | Farm 1 | 100.0 | 100.0 | 100.0 | 100.0 | 100.0 | 100.0 |
| B40_C09 | Farm 1 | 100.0 | 100.0 | 100.0 | 100.0 | 100.0 | 100.0 |
| B40_E04 | Farm 1 | 100.0 | 100.0 | 100.0 | 100.0 | 100.0 | 100.0 |
| B40_E11 | Farm 1 | 100.0 | 100.0 | 100.0 | 96.3 | 100.0 | 100.0 |
| B64_A01 | Farm 1 | 99.8 | 100.0 | 100.0 | 100.3 | N/A | 100.0 |
| B64_A02 | Farm 1 | 95.4 | 95.9 | 95.9 | 95.8 | N/A | 96.0 |
| B64_A11 | Farm 1 | 100.0 | 100.0 | 100.0 | 100.0 | N/A | 100.0 |
| B64_A12 | Farm 1 | 99.9 | 100.0 | 100.0 | 100.0 | N/A | 100.0 |
| B64_B06 | Farm 1 | 100.0 | 100.0 | 100.0 | 100.0 | N/A | 100.0 |
| B64_B12 | Farm 1 | 99.7 | 100.0 | 100.0 | 100.0 | N/A | 100.0 |
| B64_C01 | Farm 1 | 99.8 | 100.0 | 100.0 | 100.0 | N/A | 100.0 |
| B64_D01 | Farm 1 | 99.6 | 100.0 | 100.0 | 100.0 | N/A | 100.0 |
| B64_D02 | Farm 1 | 100.0 | 100.0 | 100.0 | 100.0 | N/A | 100.0 |
| B64_D03 | Farm 1 | 100.0 | 100.0 | 100.0 | 100.0 | N/A | 100.0 |
| B64_E09 | Farm 1 | 100.0 | 100.0 | 100.0 | 100.0 | N/A | 100.0 |
| B64_E12 | Farm 1 | 100.0 | 100.0 | 100.0 | 100.0 | N/A | 100.0 |
| B64_G01 | Farm 1 | 100.0 | 100.0 | 100.0 | 100.0 | N/A | 100.0 |
| B64_G07 | Farm 1 | 99.9 | 99.9 | 99.9 | 99.7 | N/A | 99.8 |
| B65_A08 | Farm 1 | 100.0 | 100.0 | 100.0 | 100.0 | N/A | 100.0 |
| B65_A09 | Farm 1 | 100.0 | 100.0 | 100.0 | 100.0 | N/A | 100.0 |
| B65_B01 | Farm 1 | 100.0 | 100.0 | 100.0 | 100.0 | N/A | 100.0 |
| B65_C01 | Farm 1 | 100.0 | 100.0 | 100.0 | 100.0 | N/A | 100.0 |
| B65_C11 | Farm 1 | 100.0 | 100.0 | 100.0 | 100.0 | N/A | 100.0 |
| B65_D04 | Farm 1 | 100.0 | 100.0 | 100.0 | 100.0 | N/A | 100.0 |
| B65_D08 | Farm 1 | 100.0 | 100.0 | 100.0 | 100.0 | N/A | 100.0 |
| B65_E08 | Farm 1 | 100.0 | 100.0 | 100.0 | 100.0 | N/A | 100.0 |
| B65_F01 | Farm 1 | 100.0 | 100.0 | 100.0 | 100.0 | N/A | 100.0 |
| B65_F04 | Farm 1 | 100.0 | 100.0 | 100.0 | 100.0 | N/A | 100.0 |
| B65_F07 | Farm 1 | 100.0 | 100.0 | 100.0 | 100.0 | N/A | 100.0 |
| B65_G10 | Farm 1 | 100.0 | 100.0 | 100.0 | 100.0 | N/A | 100.0 |
| B66_A04 | Farm 1 | 100.0 | 100.0 | 100.0 | 100.0 | N/A | 100.0 |
| B66_A05 | Farm 1 | 100.0 | 100.0 | 100.0 | 100.0 | N/A | 100.0 |
| B66_A11 | Farm 1 | 100.0 | 100.0 | 100.0 | 100.0 | N/A | 100.0 |
| B66_B09 | Farm 1 | 100.0 | 100.0 | 100.0 | 99.9 | N/A | 100.0 |

TABLE 4-continued

Percent growth reduction of *Clostridium perfringens* isolates by commercial *Bacillus* strains.

| Clostridium ID | Farm | 747 | 1104 | 1541 | 1781 | 1999 | 2018 |
|---|---|---|---|---|---|---|---|
| B66_C01 | Farm 1 | 100.0 | 100.0 | 100.0 | 100.0 | N/A | 100.0 |
| B66_C04 | Farm 1 | 100.0 | 100.0 | 100.0 | 100.0 | N/A | 100.0 |
| B66_C12 | Farm 1 | 100.0 | 100.0 | 100.0 | 100.0 | N/A | 100.0 |
| B66_D06 | Farm 1 | 100.0 | 100.0 | 100.0 | 100.0 | N/A | 100.0 |
| B66_D12 | Farm 1 | 100.0 | 100.0 | 100.0 | 100.0 | N/A | 100.0 |
| B66_E09 | Farm 1 | 100.0 | 100.0 | 100.0 | 100.0 | N/A | 100.0 |
| B66_E10 | Farm 1 | 100.0 | 100.0 | 100.0 | 100.0 | N/A | 100.0 |
| B66_F08 | Farm 1 | 100.0 | 100.0 | 100.0 | 100.0 | N/A | 100.0 |
| B66_F11 | Farm 1 | 100.0 | 100.0 | 100.0 | 100.0 | N/A | 100.0 |
| B66_G08 | Farm 1 | 100.0 | 100.0 | 100.0 | 100.0 | N/A | 100.0 |
| B66_G12 | Farm 1 | 100.0 | 100.0 | 100.0 | 100.0 | N/A | 100.0 |
| B66_H03 | Farm 1 | 100.0 | 100.0 | 100.0 | 100.0 | N/A | 100.0 |
| B66_H06 | Farm 1 | 100.0 | 100.0 | 100.0 | 100.0 | N/A | 100.0 |
| B66_H07 | Farm 1 | 100.0 | 100.0 | 100.0 | 100.2 | N/A | 100.0 |
| B66_H08 | Farm 1 | 100.0 | 100.0 | 100.0 | 100.2 | N/A | 100.0 |
| B67_A03 | Farm 1 | 100.0 | 100.0 | 99.3 | 99.3 | N/A | 100.0 |
| B67_A04 | Farm 1 | 99.6 | 99.7 | 99.7 | 99.7 | N/A | 99.7 |
| B67_A07 | Farm 1 | 99.8 | 99.9 | 99.9 | 99.7 | N/A | 99.9 |
| B42_E05 | Farm 2 | 89.2 | 20.0 | 60.2 | 85.7 | 83.3 | 61.9 |
| B42_B06 | Farm 2 | 97.9 | 98.0 | 96.4 | 93.4 | 98.1 | 85.7 |
| B42_D05 | Farm 2 | 94.2 | 18.1 | 48.2 | 98.7 | 93.6 | 56.5 |
| B47_D12 | Farm 2 | 100.0 | 100.0 | 100.0 | 100.0 | 100.0 | 100.0 |
| B46_B10 | Farm 2 | 100.0 | 100.0 | 100.0 | 100.0 | 100.0 | 100.0 |
| B46_B11 | Farm 2 | 100.0 | 100.0 | 100.0 | 100.0 | 100.0 | 100.0 |
| B46_B12 | Farm 2 | 100.0 | 100.0 | 100.0 | 100.0 | 100.0 | 100.0 |
| B46_C05 | Farm 2 | 100.0 | 100.0 | 100.0 | 100.0 | 100.0 | 100.0 |
| B47_B10 | Farm 2 | 100.0 | 100.0 | 100.0 | 100.0 | 100.0 | 100.0 |
| B47_C01 | Farm 2 | 100.0 | 100.0 | 100.0 | 100.0 | 100.0 | 100.0 |
| B45_F09 | Farm 2 | 100.0 | 0.0 | 70.7 | 100.0 | 96.7 | 82.0 |
| B45_F12 | Farm 2 | 100.0 | 100.0 | 100.0 | 100.0 | 100.0 | 100.0 |
| B45_G01 | Farm 2 | 100.0 | 100.0 | 100.0 | 100.0 | 100.0 | 100.0 |
| B45_G09 | Farm 2 | 100.0 | 99.1 | 100.0 | 100.0 | 100.0 | 100.0 |
| B58_A09 | Farm 2 | 100.0 | 100.0 | 100.0 | 100.0 | 100.0 | 100.0 |
| B58_A10 | Farm 2 | 100.0 | 100.0 | 100.0 | 100.0 | 100.0 | 100.0 |
| B58_B02 | Farm 2 | 100.0 | 100.0 | 100.0 | 100.0 | 100.0 | 100.0 |
| B58_D04 | Farm 2 | 100.0 | 100.0 | 100.0 | 100.0 | 100.0 | 100.0 |
| B58_D06 | Farm 2 | 100.0 | 100.0 | 100.0 | 100.0 | 100.0 | 100.0 |
| B58_D10 | Farm 2 | 100.0 | 100.0 | 100.0 | 100.0 | 100.0 | 100.0 |
| B58_E12 | Farm 2 | 100.0 | 100.0 | 100.0 | 100.0 | 100.0 | 100.0 |
| B58_F08 | Farm 2 | 100.0 | 100.0 | 100.0 | 100.0 | 100.0 | 100.0 |
| B58_G01 | Farm 2 | 100.0 | 100.0 | 100.0 | 100.0 | 100.0 | 100.0 |
| B58_G02 | Farm 2 | 100.0 | 100.0 | 100.0 | 100.0 | 100.0 | 100.0 |
| B60_C02 | Farm 2 | 96.0 | 96.1 | 94.6 | 94.5 | 94.3 | 96.1 |
| B58_H03 | Farm 2 | 100.0 | 100.0 | 100.0 | 100.0 | 100.0 | 100.0 |
| B58_H07 | Farm 2 | 100.0 | 100.0 | 100.0 | 100.0 | 100.0 | 100.0 |
| B60_D06 | Farm 2 | 93.3 | 0.3 | 84.0 | 84.3 | 82.5 | 83.6 |
| B67_C01 | Farm 2 | 100.0 | 97.8 | 97.8 | 98.9 | 97.8 | 97.8 |
| B67_C03 | Farm 2 | 99.3 | 99.4 | 99.6 | 99.6 | 99.6 | 99.4 |
| B67_C07 | Farm 2 | 99.3 | 99.3 | 99.3 | 99.6 | 99.3 | 99.6 |
| B67_C09 | Farm 2 | 92.5 | 81.4 | 86.3 | 91.6 | 96.1 | 32.4 |
| B67_C12 | Farm 2 | 99.4 | 99.3 | 99.1 | 99.3 | 99.4 | 99.5 |
| B67_D02 | Farm 2 | 99.3 | 99.5 | 99.7 | 99.5 | 99.7 | 99.8 |
| B67_D03 | Farm 2 | 98.5 | 98.5 | 98.5 | 98.8 | 98.5 | 98.5 |
| B67_D04 | Farm 2 | 98.5 | 98.1 | 98.9 | 98.5 | 98.1 | 97.8 |
| B67_D05 | Farm 2 | 99.3 | 99.1 | 99.1 | 98.7 | 99.5 | 99.5 |
| B67_D09 | Farm 2 | 99.3 | 99.3 | 99.3 | 99.3 | 99.3 | 94.3 |
| B67_D10 | Farm 2 | 99.0 | 99.0 | 99.1 | 98.8 | 98.8 | 58.6 |
| B67_D11 | Farm 2 | 96.7 | 99.1 | 92.4 | 95.7 | 97.7 | 96.2 |
| B67_D12 | Farm 2 | 87.9 | 84.0 | 79.0 | 87.2 | 81.0 | 89.1 |
| B67_E01 | Farm 2 | 97.2 | 99.3 | 99.7 | 97.5 | 99.3 | 99.9 |
| B67_E02 | Farm 2 | 99.1 | 99.2 | 99.2 | 99.1 | 99.4 | 99.1 |
| B67_E03 | Farm 2 | 54.8 | 81.0 | 89.3 | 32.1 | 95.2 | 95.2 |
| B67_E06 | Farm 2 | 99.5 | 99.3 | 99.4 | 99.1 | 99.6 | 99.6 |
| B68_A01 | Farm 2 | 94.5 | 95.8 | 93.8 | 96.6 | 94.1 | 91.5 |
| B68_A05 | Farm 2 | 99.4 | 99.0 | 99.2 | 99.4 | 99.5 | 99.2 |
| B68_A08 | Farm 2 | 50.8 | 99.5 | 99.4 | 98.7 | 99.8 | 99.8 |
| B68_B09 | Farm 2 | 91.1 | 92.0 | 88.1 | 90.4 | 98.9 | 81.6 |
| B68_B12 | Farm 2 | 99.2 | 99.2 | 99.4 | 99.3 | 98.3 | 99.0 |
| B68_C04 | Farm 2 | 99.4 | 99.3 | 99.5 | 99.6 | 98.7 | 92.8 |
| B56_A02 | Farm 3 | 100.0 | 100.0 | 100.0 | 100.0 | 100.0 | 100.0 |
| B56_B10 | Farm 3 | 100.0 | 100.0 | 100.0 | 100.0 | 100.0 | 100.0 |
| B50_E03 | Farm 3 | 100.0 | 100.0 | 100.0 | 100.0 | 100.0 | 100.0 |
| B50_F01 | Farm 3 | 100.0 | 100.0 | 100.0 | 100.0 | 100.0 | 100.0 |
| B50_F03 | Farm 3 | 100.0 | 13.4 | 90.3 | 100.0 | 100.0 | 100.0 |

TABLE 4-continued

Percent growth reduction of *Clostridium perfringens* isolates by commercial *Bacillus* strains.

| Clostridium ID | Farm | 747 | 1104 | 1541 | 1781 | 1999 | 2018 |
|---|---|---|---|---|---|---|---|
| B50_G06 | Farm 3 | 100.0 | 100.0 | 100.0 | 100.0 | 100.0 | 100.0 |
| B50_H01 | Farm 3 | 100.0 | 100.0 | 100.0 | 100.0 | 100.0 | 100.0 |
| B50_H02 | Farm 3 | 100.0 | 100.0 | 100.0 | 100.0 | 100.0 | 100.0 |
| B50_H07 | Farm 3 | 100.0 | 100.0 | 100.0 | 100.0 | 100.0 | 100.0 |
| B50_H08 | Farm 3 | 100.0 | 100.0 | 100.0 | 100.0 | 100.0 | 100.0 |
| B55_F10 | Farm 3 | 100.0 | 100.0 | 100.0 | 100.0 | 100.0 | 100.0 |
| B55_F12 | Farm 3 | 100.0 | 96.9 | 100.0 | 100.0 | 100.0 | 100.0 |
| B55_G02 | Farm 3 | 100.0 | 78.9 | 100.0 | 100.0 | 100.0 | 97.2 |
| B49_C10 | Farm 3 | 100.0 | 90.6 | 100.0 | 100.0 | 100.0 | 100.0 |
| B49_D05 | Farm 3 | 98.0 | 50.8 | 83.1 | 91.5 | 81.6 | 81.3 |
| B49_E11 | Farm 3 | 100.0 | 100.0 | 100.0 | 100.0 | 100.0 | 100.0 |
| B49_F10 | Farm 3 | 96.6 | 99.8 | 99.9 | 99.8 | 100.0 | 100.0 |
| B49_H03 | Farm 3 | 92.8 | 19.6 | 40.9 | 67.6 | 96.3 | 83.6 |
| B50_A04 | Farm 3 | 99.7 | 99.8 | 99.7 | 99.9 | 99.9 | 100.0 |
| B50_A06 | Farm 3 | 99.8 | 99.6 | 99.9 | 99.6 | 100.0 | 100.0 |
| B50_A07 | Farm 3 | 99.9 | 99.8 | 99.7 | 99.8 | 100.0 | 100.0 |
| B50_A10 | Farm 3 | 99.6 | 99.7 | 99.7 | 99.7 | 99.8 | 99.8 |
| B50_A11 | Farm 3 | 99.6 | 99.5 | 99.6 | 99.6 | 99.7 | 99.7 |
| B50_B01 | Farm 3 | 99.8 | 66.7 | 96.8 | 98.2 | 90.8 | 98.2 |
| B50_B10 | Farm 3 | 100.0 | 100.0 | 100.0 | 100.0 | 100.0 | 100.0 |
| B50_B11 | Farm 3 | 100.0 | 100.0 | 100.0 | 100.0 | 100.0 | 100.0 |
| B50_B12 | Farm 3 | 100.0 | 100.0 | 100.0 | 100.0 | 100.0 | 100.0 |
| B50_C05 | Farm 3 | 83.6 | 0.0 | 0.0 | 55.7 | 72.8 | 100.0 |
| B50_C08 | Farm 3 | 92.0 | 65.0 | 59.2 | 56.9 | 91.0 | 100.0 |
| B50_D09 | Farm 3 | 100.0 | 99.6 | 100.0 | 100.0 | 100.0 | 100.0 |
| B48_A08 | Farm 3 | 100.0 | 100.0 | 100.0 | 100.0 | 100.0 | 100.0 |
| B48_A11 | Farm 3 | 100.0 | 100.0 | 100.0 | 100.0 | 100.0 | 100.0 |
| B48_B01 | Farm 3 | 100.0 | 100.0 | 100.0 | 100.0 | 100.0 | 100.0 |
| B48_B03 | Farm 3 | 100.0 | 100.0 | 100.0 | 100.0 | 100.0 | 100.0 |
| B48_B11 | Farm 3 | 100.0 | 100.0 | 100.0 | 100.0 | 100.0 | 100.0 |
| B48_D02 | Farm 3 | 100.0 | 100.0 | 100.0 | 100.0 | 100.0 | 100.0 |
| B48_D06 | Farm 3 | 100.0 | 100.0 | 100.0 | 100.0 | 100.0 | 100.0 |
| B48_D12 | Farm 3 | 100.0 | 100.0 | 100.0 | 100.0 | 100.0 | 100.0 |
| B48_E06 | Farm 3 | 100.0 | 100.0 | 100.0 | 100.0 | 100.0 | 100.0 |
| B48_F08 | Farm 3 | 100.0 | 100.0 | 100.0 | 100.0 | 100.0 | 100.0 |
| B48_G10 | Farm 3 | 100.0 | 14.8 | 100.0 | 100.0 | 100.0 | 100.0 |
| B48_H02 | Farm 3 | 100.0 | 100.0 | 100.0 | 100.0 | 100.0 | 100.0 |
| B49_A05 | Farm 3 | 79.8 | 77.4 | 55.4 | 74.7 | 0.0 | 67.8 |
| B49_A07 | Farm 3 | 100.0 | 100.0 | 100.0 | 100.0 | 100.0 | 100.0 |
| B44_A10 | Farm 3 | 89.1 | 56.1 | 87.7 | 100.0 | 80.9 | 87.7 |
| B44_B01 | Farm 3 | 93.3 | 91.7 | 100.0 | 68.9 | 97.0 | 98.1 |
| B44_B02 | Farm 3 | 67.7 | 100.0 | 69.6 | 97.3 | 77.5 | 100.0 |
| B45_B11 | Farm 3 | 100.0 | 100.0 | 100.0 | 100.0 | 100.0 | 100.0 |
| B43_D08 | Farm 3 | 100.0 | 100.0 | 100.0 | 100.0 | 100.0 | 100.0 |
| B43_F12 | Farm 3 | 93.7 | 90.3 | 56.8 | 100.0 | 96.2 | 97.5 |
| Average (%) Reduction | | 97.3% | 93.2% | 95.7% | 96.9% | 96.2% | 96.6% |

Example 3: Genetic Diversity of *Salmonella* on Commercial Swine Farms and In Vitro Inhibition of *Salmonella* Growth by Distinct *Bacillus subtilis* Isolates To determine the genetic diversity of *Salmonella* serovars and the efficacy of six proprietary *B. subtilis* strains to inhibit the growth of *Salmonella* in infected swine herds, 30 *Salmonella* isolates were obtained from swine gastrointestinal tracts sampled from a commercial swine facility. The gastrointestinal tracts were dissected into four sections, including the stomach, jejunum, cecum, and colon, and tetrathionate (TT) broth with brilliant green and iodine was used to enrich for *Salmonella* from each of the swine gastrointestinal tract sections. A 1 mL aliquot from the diluted GIT sample was dispensed into 5 ml TT broth in a 15 ml conical tube and placed in a water bath at 41.5° C. for 24 hrs. After 24 hrs the enrichment tubes were moved to room temperature for 3 days. A 500 µl aliquot was taken from the enrichment tubes after the room temperature incubation. A freezer stock containing 300 µl of enrichment plus 300 µl peptone with glycerol was prepared for storage and the remaining 200 µl was used for DNA isolations. The 200 µl TT *Salmonella* culture was incubated overnight and genomic DNA (gDNA) was extracted using the methods described previously in Example 1.

Presumptive *Salmonella* isolates were confirmed by using polymerase chain reaction (PCR) using the invA gene primers (invA-F 5' GATYTGAARGCCGGTATTATTG 3', SEQ ID NO: 28; invA R 5' ATAAACTTCACGCACCGTCA 3', SEQ ID NO: 29). Each reaction mixture contained 1× Platinum Taq PCR Buffer (Invitrogen), 2 mM magnesium chloride, 1 mM deoxynucleoside triphosphates, 0.10 µM of each primer (IDT Technologies), 0.08 µl Platinum Taq DNA polymerase (Invitrogen), and 2 µl of template gDNA in a total reaction volume of 20 µl. The reaction was run on an Applied Biosystems Thermal Cycler with the following protocol: 95° C. for 5 min; 35 cycles of 95° C. for 30 s, 60° C. for 30 s, 72° C. for 1 min; and a final cycle of 72° C. for 10 min. The PCR product was then run through capillary gel electrophoresis using a Fragment Analyzer from Advance Analytical Technologies, Inc. and visualized on PROsize 2.0

(Advance Analytical Technologies, Inc). *Salmonella* pathogenic positive isolates should have an amplicon size of 107 bp.

Of the confirmed pathogenic *Salmonella* isolates, 30 genetically distinct isolates as determined by Clustered Regularly Spaced Palindromic Repeat (CRISPR) sequencing (Shariat et al., 2013) were selected for a bacteriocin inhibition assay. Briefly, each of the five *Bacillus* strains were grown from the −80° C. cell stock in Brain Heart Infusion (BHI) broth 24 h at 32° C. in a shaking incubator. A 1% transfer inoculation into fresh BHI was performed and cultures were incubated at 32° C. in a shaking incubator for 36 to 48 h. Cultures were then centrifuged 20 min at 14,000×g. Supernatants were filtered through a 0.2 μm filter. Cell-free bacteriocin solution filtrates from each *Bacillus* strain were used in the assay to determine their efficacy to inhibit *Salmonella* growth in vitro. The representative *Salmonella* isolates were grown on XLT-4 agar plates from frozen stock by incubating at 37° C. for 24 hours. A 0.125% inoculum of the overnight *Salmonella* culture was transferred to individual wells in 96 well plates with fresh BHI and 15% of a bacteriocin solution from one of the five *Bacillus* strains. Samples were incubated 24 h at 37° C. and optical density was determined by reading on a Biotek Epoch Microplate Spectrometer at 600 nm wavelength. The percent growth reduction was calculated using the following formula: (1−((pure culture isolate−neg. control)/(pos. control−neg. control)))×100), and this value was used to determine the best formulation of *Bacillus* strains to include in a customized product to control a specific farm's pathogenic *Salmonella*.

A total of 150 total *Salmonella* isolates were obtained from the gastrointestinal tract sections sampled from the commercial swine facility. From these, the growth of the 30 genetically distinct isolates selected for the bacteriocin assay was reduced most effectively by *Bacillus* strains 747 and 1781, which averaged 69.99% and 69.37%, respectively (Table 5); whereas, *Bacillus* 2018 exhibited the weakest growth reduction effect with an average of 38.02%. These data demonstrate the efficacy of *Bacillus* strains for growth inhibition of *Salmonella* in vitro, particularly by *Bacillus* strains 747 and 1781. The varying levels of effectiveness across the different *Bacillus* strains also indicates the need for a customer based approach when choosing an enteric pathogen control probiotic, to ensure the probiotic effectiveness against the targeted pathogens.

TABLE 5

Percent growth reduction by proprietary *Bacillus* strains 747, 1104, 1541, 1781, and 2018 against pathogenic swine *Salmonella* isolates.

| *Salmonella* ID | Farm | Site | Sample Type | Proprietary *Bacillus* strains | | | | |
|---|---|---|---|---|---|---|---|---|
| | | | | 747 | 1104 | 1541 | 1781 | 2018 |
| S.15C.2 | 1 | A | Cecum | 96.11 | 59.36 | 59.7 | 94.64 | 49.21 |
| S.16J.1 | 1 | A | Jejunum | 84.59 | 51.51 | 49.05 | 84.31 | 48.98 |
| S.17L.1 | 1 | A | Colon | 87.03 | 48.11 | 51.37 | 85.17 | 50.04 |
| S.20C.1 | 1 | A | Cecum | 83.74 | 51.82 | 53.25 | 83.06 | 47.66 |
| S.21S.2 | 1 | A | Stomach | 92.78 | 58.03 | 63.62 | 87.76 | 54.92 |
| S.14L.2 | 1 | A | Colon | 86.70 | 49.73 | 45.43 | 85.70 | 37.28 |
| S.22C.2 | 1 | A | Cecum | 86.35 | 33.30 | 48.93 | 86.44 | 27.98 |
| S.23C.3 | 1 | A | Cecum | 87.35 | 47.76 | 20.46 | 87.82 | 24.07 |
| S.24C.3 | 1 | A | Cecum | 89.01 | 55.46 | 66.28 | 88.84 | 35.77 |
| S.20S.1 | 1 | A | Stomach | 89.56 | 47.81 | 43.51 | 88.84 | 41.27 |
| S.9S.1 | 1 | B | Stomach | 84.79 | 43.63 | 50.92 | 65.21 | 50.69 |
| S.9S.2 | 1 | B | Stomach | 80.81 | 48.39 | 48.73 | 81.32 | 42.95 |
| S.12C.2 | 1 | B | Cecum | 84.17 | 44.13 | 45.61 | 86.96 | 42.99 |
| S.24C.4 | 1 | B | Cecum | 43.79 | 34.45 | 39.19 | 43.44 | 46.86 |
| S.17J.1 | 1 | B | Jejunum | 54.60 | 35.84 | 65.84 | 56.42 | 38.05 |
| S.17J.3 | 1 | B | Jejunum | 85.78 | 48.18 | 44.33 | 82.07 | 49.09 |
| S.16L.3 | 1 | B | Colon | 66.04 | 46.82 | 46.25 | 63.71 | 41.71 |
| S.20L.4 | 1 | B | Colon | 88.16 | 63.51 | 67.83 | 89.13 | 59.72 |
| S.12C.5 | 1 | B | Cecum | 84.62 | 48.15 | 46.99 | 85.55 | 46.45 |
| S.16L.1 | 1 | B | Colon | 67.40 | 47.08 | 51.59 | 66.87 | 43.82 |
| S.01S.1 | 1 | C | Stomach | 36.13 | 16.33 | 0.41 | 11.45 | 14.84 |
| S.03C.3 | 1 | C | Cecum | 85.55 | 60.37 | 67.96 | 81.84 | 54.56 |
| S.03C.4 | 1 | C | Cecum | 75.94 | 57.60 | 58.07 | 84.09 | 53.92 |
| S.05S.1 | 1 | C | Stomach | 31.18 | 19.87 | 0.72 | 34.41 | 17.16 |
| S.06S.1 | 1 | C | Stomach | 64.26 | 25.13 | 30.53 | 61.37 | 26.18 |
| S.21C.2 | 1 | C | Cecum | 66.86 | 42.68 | 38.98 | 80.76 | 43.01 |
| S.22S.1 | 1 | C | Stomach | 27.07 | 4.56 | 5.25 | 22.73 | 12.97 |
| S.24J.1 | 1 | C | Jejunum | 39.06 | 16.51 | 14.48 | 41.13 | 17.83 |
| S.24C.1 | 1 | C | Cecum | 26.47 | 13.48 | 21.18 | 39.49 | 4.83 |
| S.24L.1 | 1 | C | Colon | 23.87 | 12.86 | 2.53 | 30.60 | 15.85 |
| Average: | | | | 69.99 | 41.08 | 41.63 | 69.37 | 38.02 |

Example 4: Genetic Diversity of *Streptococcus* sp. on Commercial Swine Farms and In Vitro Inhibition of *Streptococcus* Growth by Distinct *Bacillus subtilis* Strains Potentially pathogenic *Streptococcus* are capable of causing a range of disease in swine, including meningitis, sepsis, endocarditis, and pneumonia, with *S. suis* being the causative agent in most *Streptococcus*-related disease in swine. Limiting the load of *Streptococcus* in the gastrointestinal tract of pigs could potentially play a role in preventing the translocation of *Streptococcus* across the mucosal surface associated with systemic infection by modulating the Streptococci population present in the gastrointestinal tract. In this study, the *Streptococcus* populations were assessed from samples obtained on a commercial swine facility and the efficacy of six proprietary *B. subtilis* strains (747, 1104, 1541, 1781, 2018, and 1999) to inhibit growth of *Streptococcus* isolates in vitro was determined.

*Streptococcus* isolates were cultured from swine sources (fecal material or gastrointestinal tissue) on Columbia CNA agar with 5% sheep blood (BD) and grown at 37° C. for 24 h. Presumptive *Streptococcus* isolates were collected and grown up in Todd-Hewitt Broth (BD). Genomic DNA (gDNA) was extracted using the same methods previously described in Example 1.

*Streptococcus* sp. determination was performed by sequencing of the PCR amplified 16S rRNA gene using primers 27F-YM (AGAGTTTGATYMTGGCTCAG, SEQ ID NO: 30) and 1492R-Y (TACCTTGTTAYGACTT, SEQ ID NO: 13). The PCR reaction mixture contained 1× Platinum Taq PCR buffer (Invitrogen), 2 mM $MgCl_2$, 1 mM dNTPs, 0.4 µM of each primer, 2 µL gDNA, and 0.08 µL Platinum Taq DNA polymerase (Invitrogen) in a reaction volume of 20 µL. The PCR temperature cycle used included an initial 95° C. for 4 min, 35 cycles of 95° C. for 30 s, 50° C. for 30 s, 72° C. for 2 min, and a final 72° C. for 7 min. Unpurified PCR samples were sent to Genewiz (www.genewiz.com) for standard Sanger sequencing. Obtained sequences were compared to known bacterial strains in the EZbiocloud online database (www.ezbiocloud.net) to identify the isolates. A dendrogram of genetic diversity was constructed in BioNumerics (Applied Maths) using the obtained 16S rRNA sequences (FIG. 3.)

To generate bacteriocin from each of the six proprietary *Bacillus* strains, each was grown from frozen stock in Brain Heart Infusion (BHI) broth 24 h at 32° C. in a shaking incubator. A 1% transfer inoculation into fresh BHI was performed and cultures were incubated at 32° C. in a shaking incubator for 36 to 48 h. Cultures were then centrifuged 20 min at 14,000×g, and supernatants were filtered through a 0.2 µm filter. The effectiveness of the bacteriocin produced from each *Bacillus* strain in reducing growth of *Streptococcus* was measured using an in vitro assay. Briefly, a selection of *Streptococcus* isolates representing the genetic diversity of those collected, were struck from frozen stock onto Todd-Hewitt agar plates and incubated 24 h at 37° C. Isolated colonies were inoculated into BHI and incubated 24 h at 37° C. A 0.125% inoculum of the overnight culture was transferred to individual wells in 96 well plates with fresh BHI and 15% of a bacteriocin solution from one of the six *Bacillus* strains. Samples were incubated 24 h at 37° C. and optical density was determined by reading on a Biotek Epoch Microplate Spectrometer at 600 nm wavelength. The percent growth reduction was calculated with the following formula, (1−((pure culture isolate−neg. control)/(pos. control−neg. control))×100, and this value was used to determine the best formulation of *Bacillus* strains to include in a customized product to control a specific farm's pathogenic *Streptococcus*.

Three of the six *Bacillus* strains tested (747, 1781, and 1999) produced bacteriocins that were highly effective in reducing the growth of the tested *Streptococcus* diversity (Table 6). These three *Bacillus* strains each was able to reduce *Streptococcus* growth by >95%. These data demonstrate that *Bacillus* strains are very effective in reducing the growth of diverse representatives of the *Streptococcus* community, particularly *Bacillus* strains 747, 1781, and 1999. The varying levels of effectiveness for growth inhibition of *Streptococcus* sp. across the different *Bacillus* strains indicates at the use of a combination probiotic would be most effective for control, and supports the need for a customer based approach when choosing a pathogen control probiotic, to ensure effectiveness against the customer's targeted pathogens.

TABLE 6

Percent growth reduction of *Streptococcus* by different *Bacillus* strains.

| | | % Growth Reduction by *Bacillus* Strain | | | | | |
|---|---|---|---|---|---|---|---|
| Isolate ID | 16S ID | 747 | 1104 | 1541 | 1781 | 1999 | 2018 |
| B21_B08 | *S. suis* | 95.0 | 42.7 | 36.0 | 83.3 | 36.4 | 10.1 |
| B21_C09 | *S. suis* | 98.8 | 99.6 | 95.8 | 100.1 | 99.7 | 99.4 |
| B21_E12 | *S. suis* | 64.6 | 99.2 | 99.8 | 99.4 | 99.8 | 99.6 |
| B21_G03 | *S. suis* | 99.8 | 99.3 | 99.5 | 74.7 | 99.3 | 99.3 |
| B22_B01 | *S. suis* | 98.9 | 99.6 | 99.9 | 99.4 | 99.9 | 99.9 |
| B22_D02 | *S. suis* | 100.0 | 99.8 | 100.2 | 100.2 | 100.0 | 98.4 |
| B24_A04 | *S. suis* | 99.7 | 98.5 | 99.7 | 99.8 | 98.4 | 99.5 |
| B24_A09 | *S. suis* | 100.5 | 100.0 | 100.3 | 100.5 | 100.3 | 100.5 |
| B27_D06 | *S. suis* | 99.9 | 99.9 | 99.7 | 100.1 | 99.7 | 99.9 |
| B27_E03 | *S. suis* | 99.6 | 99.6 | 99.8 | 99.6 | 99.4 | 99.8 |
| B27_H06 | *S. suis* | 99.8 | 99.5 | 99.5 | 100.2 | 100.0 | 99.8 |
| B28_C02 | *S. suis* | 52.0 | 99.7 | 99.8 | 97.3 | 99.8 | 100.0 |
| B28_E11 | *S. suis* | 74.0 | 99.7 | 99.7 | 100.0 | 99.7 | 99.7 |
| B29_B02 | *S. suis* | 99.8 | 53.1 | 91.8 | 100.2 | 99.3 | 96.9 |
| B29_C11 | *S. suis* | 49.3 | 99.7 | 100.0 | 100.1 | 99.9 | 99.1 |
| B30_D09 | *S. suis* | 100.0 | 74.6 | 95.5 | 99.4 | 98.8 | 90.4 |
| B30_D11 | *S. suis* | 100.0 | 98.4 | 99.8 | 100.0 | 99.3 | 99.8 |
| B22_C03 | *S. parasuis* | 99.0 | 99.4 | 99.7 | 99.4 | 99.0 | 99.0 |
| B26_H02 | *S. parasuis* | 99.1 | 99.0 | 72.6 | 99.0 | 96.5 | 99.3 |
| B13_B10 | *S. gallolyticus* | 98.1 | 98.1 | 97.9 | 98.1 | 99.1 | 94.3 |
| B39_E04 | *S. gallolyticus* | 98.5 | 11.9 | 98.4 | 98.5 | 99.4 | 98.8 |
| B41_G04 | *S. gallolyticus* | 98.9 | 99.0 | 99.1 | 99.1 | 99.5 | 98.8 |
| B72_G01 | *S. gallolyticus* | 97.2 | 97.8 | 98.0 | 98.1 | 98.8 | 95.5 |
| B75_E06 | *S. gallolyticus* | 98.6 | 17.7 | 32.6 | 98.7 | 99.5 | 30.8 |
| B91_A08 | *S. gallolyticus* | 98.0 | 98.3 | 98.2 | 97.8 | 99.4 | 98.5 |
| B91_G04 | *S. gallolyticus* | 59.3 | 65.8 | 72.5 | 47.2 | 47.6 | 71.0 |
| B93_C06 | *S. gallolyticus* | 98.6 | 99.1 | 44.3 | 99.1 | 99.6 | N/A |
| B93_F04 | *S. gallolyticus* | 99.0 | 18.8 | 18.5 | 99.1 | 99.6 | 24.9 |
| B12_D05 | *S. hyointestinalis* | 97.9 | 97.7 | 98.7 | 97.8 | 99.5 | 97.9 |
| B12_F01 | *S. hyointestinalis* | 98.0 | 97.8 | 97.9 | 98.2 | 99.1 | 60.8 |
| B13_B08 | *S. hyointestinalis* | 98.9 | 8.6 | 23.5 | 99.0 | 99.6 | 17.4 |
| B38_D04 | *S. hyointestinalis* | 97.3 | 97.2 | 97.5 | 98.0 | 98.5 | 95.9 |
| B41_B08 | *S. hyointestinalis* | 98.3 | 98.5 | 98.4 | 98.6 | 98.9 | 95.2 |
| B72_C01 | *S. leutinensis* | 98.0 | 96.9 | 98.0 | 97.2 | 97.8 | 97.1 |
| B74_C05 | *S. leutinensis* | 96.5 | 97.4 | 97.5 | 97.4 | 98.7 | 94.8 |
| B49_F07 | *S. oralis* | 95.1 | 95.1 | 93.4 | 93.9 | 95.1 | 94.2 |
| Average % Inhibition | | 93.2 | 84.9 | 87.6 | 96.4 | 96.0 | 87.3 |

Example 5. Effect of In-Feed Administration of *Bacillus* Strains Customized to Control a Swine Farm's Specific Pathogenic Challenges Shifts in genetic diversity of *E. coli* and *C. perfringens* was assessed in sows on a commercial swine operation after the administration of chlortetracycline (CTC) antibiotic and after the administration of a *B. subtilis* probiotic composed of *Bacillus* strains 747 and 1781. To obtain a baseline assessment of the pathogenic diversity present in the sow herd prior to administration of CTC or the *Bacillus* probiotic, rectal swabs from 60 sows distributed throughout the breeding, gestation, and lactation production phases. Approximately one month after obtaining the baseline rectal swabs, CTC was administered to the sow herd for two weeks and rectal swabs were obtained from the same 60 sows to assess shifts in the pathogenic diversity after antibiotic treatment. Then the *Bacillus* probiotic was added to feed following the CTC treatment and rectal swabs from the same 60 sows were obtains to assess the shifts in pathogenic diversity after the probiotic treatment.

Swabs were washed in a sterile peptone tube and serial 10-fold dilutions were plated on CHROM agar and Tryptose Sulfite Cyclocerine agar for growth of *E. coli* and *Clostridium*, respectively. Presumptive *E. coli* and *Clostridium* colonies were picked from the plates and multiplex PCR was performed on each of the picked isolates using a PCR primer panel that included genes associated with pathogenicity of *E. coli* and *Clostridium* (Table 1). Bionumerics software was used to generate dendrograms to determine genetic diversity of the pathogenic isolates detected for each of the pathogens. Genetically distinct isolates from the initial baseline sampling were assayed for growth inhibition by a panel of six proprietary *Bacillus* strains and a probiotic formulation was designed to provide optimal control of the specific pathogen diversity measured for the swine herd.

A total of 323 pathogenic *E. coli* isolates were collected from 60 rectal swabs that served as a baseline sampling prior to the administration of CTC or the *Bacillus* probiotic (FIG. 1). Following the administration of CTC, nine pathogenic *E. coli* isolates were obtained from rectal swabs from the same 60 sows and only four pathogenic *E. coli* isolates were collected from the 60 sows following the *Bacillus* probiotic treatment. Although the number of pathogenic *C. perfringens* isolates collected from the same 60 sows were similar (~250 to 330 total isolates) at the baseline sampling, after CTC, and after the *Bacillus* probiotic timepoints, there is an evident shift in the genetic diversity of the *C. perfringens* isolates detects at each sampling point.

Example 6: *Bacillus* 747 Improves Fecal Scores in Nursery Pigs

Commercial nursery pigs were evaluated to determine the impact of feeding *Bacillus*-based microbials on post-weaning growth performance, biological responses, and health status. A total of 1,200 mixed-sex weanling pigs were grouped and randomly placed in 48 pens with 20-27 pigs per pen upon arrival to the growing facility (day 0). Pigs were weighed by pen on day 0, blocked by initial BW and assigned to one of two dietary treatments (Table 7), a control basal diet (Treatment A) and experimental diet with *Bacillus* added at 1 lb/ton of feed (Treatment B). The basal nursery diets were formulated to meet or exceed the nutrient requirements of nursery pigs for each diet phase.

TABLE 7

Experimental treatments

| Treatment | Nursery Bacillus[1] | Diet in Nursery | Inclusion of Bacillus[1] | #Pens in Nursery | #Pigs per Pen | Total # Pigs |
|---|---|---|---|---|---|---|
| A | − | Basal | None | 24 | 20-27 | 600 |
| B | + | Experimental | 1 lb/ton Bacillus | 24 | 20-27 | 600 |

[1]Bacillus test product consisted of strain 747 for a target of $1.5 \times 10^5$ CFU per gram of feed.

TABLE 8

Feeding program for nursery phases

| Nursery Phase | Diet | Days on Feed |
|---|---|---|
| Phase 1: 9-15 lb BW | Experimental | 11 |
| Phase 2: 15-25 lb BW | Experimental | 14 |

The nursery pig trial was conducted for 25 days in two-phase feeding program (Table 8), and pen weights and feed intake by pen were determined initially and at the end of each diet phase. The data was used to calculate average daily gain (ADG), average daily feed intake (ADFI), and feed:gain ratio (F:G) for each nursery phase. Fecal scores were obtained for pigs on Day 3, 5, 7, and 10 post-weaning, using a fecal scoring system described by Marquardt et al. (1999). Fecal samples were collected at two time points from each pen for microbial counts on day 3 and day 15 post-weaning. Briefly, 11 grams of fecal material was placed in a whirlpak bag with 99 mL peptone and masticated. To obtain *E. coli* counts, the masticated sample was serially diluted 10-fold and plated on CHROMagar. The plates were incubated aerobically at 37° C. for 24 hours and *E. coli* colonies were enumerated to determine CFU/g of fecal material. To obtain *Clostridium* counts, the masticated samples were spore treated for 30 minutes at 55° C., diluted, and plated on tryptose sulfite cycloserine agar. The plates were incubated anaerobically at 37° C. for 24 hours and *Clostridium* colonies were enumerated to determine CFU/g of fecal material.

Blood samples were obtained from two barrows from each pen on d 0 and at the end of Phase 2 for immunological analyses, including immunocrit and serum cytokine concentrations. Immunocrit was measured following the procedure described by Vallet et al. (2013). Briefly, fifty microliters of serum were mixed with 50 µL 40% $(NH_4)_2SO_4$, and the sample was centrifuged (Damon/IEC micro-hematocrit centrifuge) in a hematocrit microcapillary tube (Fisher Scientific) for 10 min (12,700 g). The length of the Ig precipitate in the tube was divided by the length of the solution in the tube to generate a ratio with no units. Serum cytokines were measured using a commercially available kit called Cytokine & Chemokine 9-Plex Porcine ProcartaPlex™ Panel #1 (Invitrogen, Carlsbad, Calif.) at Veterinary Diagnostic Labs of University of Minnesota.

Statistical analysis of the data was analyzed using ANOVA by the MIXED procedure of SAS. Pen served as the experimental unit. The statistical model included fixed effect of dietary treatments and random effect of block. Multiple comparisons between treatments were performed using the Tukey adjustment option of SAS. All results were reported as least squares means. The significance level chosen was α=0.05. Treatment effect was considered significant if P<0.05, whereas values between 0.05≤P≤0.10 were considered as statistical trends.

The administration of the *Bacillus* probiotic did not improve growth performance over the control pigs, but did improve the fecal score of pigs at 7 days post-weaning (P=0.01) and the overall averaged fecal scores (P=0.05) during the first two weeks of the nursery period (Table 9). Fecal counts of *E. coli* and *Clostridium* (Table 10), serum cytokine levels (Table 11), and immunocrit values (Table 12) were not affected by dietary treatment in this study. These data demonstrate that *Bacillus* strain 747 effectively improves gastrointestinal health of nursery pigs as indicated by the improvement in fecal scores observed in treated pigs during the first two weeks after weaning.

TABLE 9

Effects of feeding *Bacillus* fermentation product on growth performance of pigs (values are least square means)

| | Treatment | | | |
|---|---|---|---|---|
| Item | Control | *Bacillus*[1] | PSE | P-value |
| # of Pens | 24 | 24 | | |
| # of Pigs | 600 | 600 | | |
| Start BW, lb | 12.9 | 12.9 | 0.2 | 0.98 |
| Phase 1; 11 days | | | | |
| ADG, lb/day | 0.15 | 0.16 | 0.02 | 0.68 |
| ADFI, lb/day | 0.52 | 0.52 | 0.02 | 0.92 |
| G/F | 0.29 | 0.30 | 0.04 | 0.68 |
| BW end of Phase 1, lb | 14.3 | 14.4 | 0.3 | 0.80 |
| Phase 2; 14 days | | | | |
| ADG, lb/day | 0.76 | 0.76 | 0.02 | 0.76 |
| ADFI, lb/day | 0.96 | 0.97 | 0.02 | 0.47 |
| F/G | 1.28 | 1.28 | 0.02 | 0.93 |
| BW end of Phase 2, lb | 25.1 | 25.2 | 0.6 | 0.75 |
| Phase 1 + 2; 25 days | | | | |
| ADG, lb/day | 0.51 | 0.52 | 0.02 | 0.60 |
| ADFI, lb/day | 0.78 | 0.79 | 0.01 | 0.60 |
| F/G | 1.54 | 1.52 | 0.03 | 0.57 |
| Removal, % | 3.7 | 2.8 | | 0.42 |
| Treated pigs, % | 24.2 | 21.0 | | 0.25 |
| Fecal score | | | | |
| Day 3 | 1.25 | 1.46 | 0.18 | 0.24 |
| Day 5 | 1.46 | 1.67 | 0.14 | 0.15 |
| Day 7 | 1.00 | 1.38 | 0.15 | 0.01 |
| Day 10 | 0.79 | 0.75 | 0.12 | 0.74 |
| Average | 0.90 | 1.05 | 0.07 | 0.05 |

[1]*Bacillus* fermentation product consisted of strain 747 for a target of $1.5 \times 10^5$ CFU per gram of feed.

TABLE 10

Effects of feeding *Bacillus* fermentation product on fecal measurements of nursery pigs (values are least square means)

| | Treatment | | | |
|---|---|---|---|---|
| Item | Control | *Bacillus*[1] | PSE | P-value |
| At weaning | | | | |
| E coli., log cfu/g | 8.1 | 8.0 | 0.1 | 0.53 |
| Clostridium, log cfu/g | 6.0 | 6.1 | 0.2 | 0.53 |
| End of Phase 2 | | | | |
| E coli., log cfu/g | 7.8 | 7.7 | 0.2 | 0.65 |
| Clostridium, log cfu/g | 3.3 | 3.4 | 0.2 | 0.53 |

[1]*Bacillus* fermentation product consisted of strain 747 for a target of $1.5 \times 10^5$ CFU per gram of feed.

TABLE 11

Effects of feeding *Bacillus* fermentation product on serum cytokines of nursery pigs (values are least square means)

| | Treatment | | | |
|---|---|---|---|---|
| Item | Control | *Bacillus*[1] | PSE | P-value |
| End of Phase 2 | | | | |
| IFN-alpha, pg/ml | 1.55 | 1.69 | 8.55 | 0.60 |
| IL-6, pg/ml | 23.8 | 27.5 | 4.2 | 0.39 |
| IL-8, pg/ml | 56.3 | 53.6 | 15.8 | 0.87 |
| IL-12, pg/ml | 405.6 | 458.3 | 126.6 | 0.58 |

[1]*Bacillus* fermentation product consisted of strain 747 for a target of $1.5 \times 10^5$ CFU per gram of feed.

TABLE 12

Effects of feeding *Bacillus* fermentation product on immunocrit ratio of nursery pigs (values are least square means)

| | Treatment | | | |
|---|---|---|---|---|
| Item | Control | *Bacillus*[1] | PSE | P-value |
| Nursery Pig Immunocrit | | | | |
| At weaning | 0.027 | 0.027 | 0.001 | 0.91 |
| End of Phase 2 | 0.041 | 0.041 | 0.003 | 0.89 |

[1]*Bacillus* fermentation product consisted of strain 747 for a target of $1.5 \times 10^5$ CFU per gram of feed.

Example 7: *Bacillus* 747 Improves Growth Performance and Reduces Severity of Diarrhea in *E. coli* Challenged Pigs A total of 60 weanling barrows with an average wean age of 19.7 days old and an average weight for the group of 12.1 lb were used to determine the effect of feeding a *Bacillus*-based direct fed microbial for controlling F18 *E. coli*. Weanling pigs were individually weighed at arrival (day-5) and blocked by body weight. Pigs within each weight block were randomly allotted to one of three treatments: A) an unchallenged control group; B) a challenged control group inoculated with F18 *E. coli*; C) a *Bacillus* treatment group inoculated with F18 *E. coli* and fed a *Bacillus* supplemented diet (Table 13). This experimental design resulted in 2 pigs per pen and 10 pens representing each of the three treatments. Unchallenged pens were located away from the challenged pens and barriers were placed between treatments to reduce the chance of treatment contamination.

The basal nursery diet were formulated to meet or exceed the nutrient requirements of nursery pigs for each diet phase, and the *Bacillus* treatment was added to this basal diet to provide $3.75 \times 10^5$ CFU/g of feed. Pigs were fed their respective experimental diets from day-5 to 0 of the trial. On day 0 and day 1 of the study, each pig was orally inoculated with 5 mL of F18 *E. coli* inoculant, to provide $2.0 \times 10^8$ CFU/mL for a total challenge of $1 \times 10^9$ CFU of *E. coli* administered to each challenged pig.

Individual body weights were obtained from each pig on test on day-5, day 0 (prior to challenge), and day 3. Feed offered to each pen was recorded and refusals were weighed by pen on day 0 and day 3. These data were used to calculate ADG, ADFI, and G:F, pre- and post-challenge. Each pig was monitored and assessed for occurrence and severity of post-weaning diarrhea using a fecal consistency scoring system described by Marquardt et al. (1999) (0=normal; 1=soft feces; 2=mild diarrhea; 3=severe diarrhea) at time 0 (prior to challenge), 1, 2, and 3-days post-challenge by the same trained personnel with no prior knowledge of dietary treatment allotment. One pig from each pen was sacrificed on day 4 post-inoculation for collection of intestinal tissue to quantify *E. coli*. Briefly, a 15 cm section of the ileum was collected proximal to the ileal-cecal junction. Intestinal samples were processed and cultured for *E. coli* to determine the CFU of *E. coli*/g of tissue and the pathogenicity of the *E. coli* isolates. Methodology for determining the pathogenicity of *E. coli* was previously described in Example 1 and for determining CFU of *E. coli*/g of tissue in Example 6.

Data were analyzed using one-way ANOVA by the MIXED procedure of SAS for this complete randomized design. Pen served as the experimental unit. The statistical model included the fixed effect of dietary treatment and random effect of block. Initial pen body weight was used as covariate for analysis of all responses. Multiple comparisons between treatments were performed using the Tukey adjustment option of SAS. All results were reported as least squares means. The significance level chosen was α=0.05. Treatment effect was considered significant if P<0.05, whereas values between 0.05≤P≤0.10 were considered as statistical trends.

Pigs in the challenged control group lost more weight, ate less feed, and had a lower body weight compared to unchallenged control pigs (P <0.05) three days post-challenge (Table 14). During the same time period, the ADG, ADFI, and body weight of pigs challenged with *E. coli* and administered the *Bacillus* probiotic was not different from the unchallenged control pigs. Challenged control pigs had a looser fecal consistency, as indicated by a higher (P<0.05) fecal score than the unchallenged control pigs. Although both challenged groups had a greater (P<0.05) frequency of diarrhea than the unchallenged control pigs, the fecal consistency of challenged pigs administered the *Bacillus* treatment did not differ from the unchallenged control pigs. Despite the differences observed for fecal consistency and diarrhea incidence, the intestinal counts of *E. coli* did not differ between any of the three treatments.

TABLE 13

Experimental treatments

| Treatment | Treatment name | Testing Product | Test Product Inclusion | Enteric Challenge | # Pigs per Pen | # of Pens | Total # Pigs |
|---|---|---|---|---|---|---|---|
| A | Non-Challenge | None | None | None | 2 | 10 | 20 |
| B | Challenge Cont. | None | None | *E. coli* F18 | 2 | 10 | 20 |
| C | *Bacillus*[1] | Prod Y | 33.3 lb/ton | *E. coli* F18 | 2 | 10 | 20 |
| | | | | | TOTAL | 30 | 60 |

[1]*Bacillus* fermentation Product Y (strain 747) was included to deliver $3.75 \times 10^5$ CFU/gram of feed.

TABLE 14

Effects of feeding *Bacillus* fermentation product in weanling pigs artificially challenged with *Escherichia coli*. F18 (values are least square means)

| Item | None Challenged-Control | Challenged Control | *Bacillus* 747 | PSE | P-value |
|---|---|---|---|---|---|
| # of Pens | 10 | 10 | 10 | | |
| # of Pigs prior to challenge | 20 | 19 | 20 | | |
| Prior to challenge, −5 to 0-dpi | | | | | |
| BW on −5 dpi, lb | 12.1 | 12.1 | 12.1 | 0.5 | 0.95 |
| ADG −5 to 0 dpi,[1] lb/day | 0.00 | −0.09 | 0.04 | 0.05 | 0.17 |
| ADFI −5 to 0 dpi,[1] lb/day | 0.13 | 0.12 | 0.15 | 0.02 | 0.42 |
| BW on 0-dpi,[1] lb | 11.8 | 11.6 | 12.0 | 0.2 | 0.41 |
| Post challenge, 0 to 3-dpi | | | | | |
| ADG 0 to 3-dpi,[2] lb/day | $0.10^a$ | $-0.12^b$ | $-0.03^{ab}$ | 0.06 | 0.03 |
| ADFI 0 to 3-dpi,[2] lb/day | $0.33^a$ | $0.20^b$ | $0.30^{ab}$ | 0.03 | 0.03 |
| BW on 3-dpi,[2] lb | $12.5^a$ | $11.4^b$ | $12.0^{ab}$ | 0.2 | 0.02 |
| Fecal score | | | | | |
| 0-dpi | 0.25 | 0.80 | 0.20 | 0.21 | 0.12 |
| 1-dpi | 0.40 | 1.25 | 0.75 | 0.28 | 0.13 |
| 2-dpi | $0.60^a$ | $2.00^b$ | $1.50^{ab}$ | 0.30 | 0.01 |
| 3-dpi | 0.60 | 1.00 | 1.10 | 0.27 | 0.38 |
| Average 1 to 3-dpi | $0.53^a$ | $1.40^b$ | $1.12^{ab}$ | 0.53 | 0.05 |
| Pig days | 54 | 51 | 51 | | |
| Diarrhea days | 11 | 23 | 23 | | |
| Diarrhea frequency, % | $20.4^a$ | $45.1^b$ | $45.1^b$ | | 0.05 |
| Fecal analysis | | | | | |
| *E coli*., log cfu/g | 6.0 | 5.4 | 5.8 | 0.4 | 0.48 |
| ETEC, log cfu/g | 5.9 | 5.1 | 5.8 | 0.5 | 0.39 |
| F18, log cfu/g | 5.4 | 4.4 | 5.0 | 0.7 | 0.56 |

[1]BW on −5 dpi was used as covariate in the model
[2]BW on 0-dpi was used as covariate in the model
[a,b]Means without a common superscript differ (P < 0.05)

Example 8: *Bacillus* 2018 Improves Growth Performance of Grow-Finish Pigs

This study was conducted to evaluate the effects of feeding two different *Bacillus* probiotic strains to grow-finish pigs. A total of 918 pigs weighing 39.5±2.6 lb were sorted by gender into 35 pens with 27 pigs/pen. Pens were blocked by pig body weight and randomly assigned to one of three dietary treatments in a randomized complete block design, resulting in 11 pens representing the control treatment and 12 pens representing the other two treatments. Treatments consisted of: 1) a control basal diet, 2) the basal diet supplemented with *Bacillus* 1781 at a 2 lb/ton inclusion level to provide $2\times10^5$ CFU/g of feed; and 3) the basal diet supplemented with *Bacillus* 2018 at a 2 lb/ton inclusion level to provide $2\times10^5$ CFU/g of feed (Table 15). Pigs were on test from approximately 35 lb until they reached 190 lb of body weight and fed six diet phases over the course of the study. Basal diets were formulated to meet or exceed the nutrient requirements of pigs during each production phase. Pig body weights were obtained by pen at the end of each phase and feed refusals were determined to calculate ADG, ADFI, and feed:gain (F:G) for each pen.

Data were analyzed using ANOVA by the MIXED procedure of SAS. For growth performance of grow-finish phase, pen served as the experimental unit. The statistical model included the fixed effect of dietary treatment and random effect of block. Initial pen body weight was used as covariate for analysis of growth performance. Multiple comparisons between treatments were performed using the Tukey adjustment option of SAS. All results were reported as least squares means. The significance level chosen was $\alpha=0.05$. Treatment effect was considered significant if $P<0.05$, whereas values between $0.05 \leq P \leq 0.10$ were considered as statistical trends.

During Phase 3, pigs fed *Bacillus* 2018 had lower ($P<0.05$) ADFI than pigs fed *Bacillus* 1781, although ADFI did not differ from control when pigs were fed either of the two *Bacillus* strains (Table 16). Pigs fed *Bacillus* 2018 had a 5.8% improvement in ADG compared to control pigs during Phase 5. Feed efficiency was also improved ($P<0.05$) with *Bacillus* 2018 supplementation compared to pigs fed *Bacillus* 1781, and although there was no statistically significant difference compared to control pigs, *Bacillus* 2018 resulted in an 8% improvement in F:G over the control group. When evaluating the overall study across all six phases, pigs fed *Bacillus* 2018 had a 2.9% improvement ($P<0.05$) in feed efficiency compared to pigs fed the control diet. These data demonstrate that *Bacillus* probiotics are efficacious for improving growth performance and efficient gain in grow-finish pigs.

TABLE 15

Dietary treatments

| Treatment | Additive | Inclusion Rate | # of Pens | # pigs/pen | Total # of pigs |
|---|---|---|---|---|---|
| 1. Control | None | — | 11 | 27 | 297 |
| 2. DFM 1 | Product A[1] | 2.0 lb/ton | 11 | 27 | 297 |
| 3. DFM 2 | Product B[2] | 2.0 lb/ton | 12 | 27 | 324 |
|  |  |  |  | TOTAL | 918 |

[1]Product A = DFM 1, strain 1781.
[2]Product B = DFM 2, strain 2018.

TABLE 16

Growth Performance

| Item | Control | DFM 1[1] | DFM 2[1] | PSE | P-value | DFM 1 vs. CON | DFM 2 vs. CON |
|---|---|---|---|---|---|---|---|
| # of Pens | 11 | 11 | 12 | N/A | N/A | N/A | N/A |
| # of Pigs | 297 | 297 | 324 | N/A | N/A | N/A | N/A |
| Start BW, lb | 39.4 | 39.6 | 39.5 | 0.8 | 1.00 | N/A | N/A |
| *Phase 1; 14 days* | | | | | | | |
| ADG, lb/day | 1.49 | 1.47 | 1.52 | 0.02 | 0.21 | −1.5% | 1.7% |
| ADFI, lb/day | 1.95 | 1.93 | 2.01 | 0.04 | 0.15 | −1.2% | 2.9% |
| F/G | 1.31 | 1.31 | 1.32 | 0.02 | 0.75 | 0.3% | 1.2% |
| BW end of Phase 1, lb | 60.4 | 60.2 | 60.7 | 0.3 | 0.33 | −0.2 lb | 0.4 lb |
| *Phase 2; 10 days* | | | | | | | |
| ADG, lb/day | 1.64 | 1.65 | 1.61 | 0.03 | 0.71 | 0.2% | −2.3% |
| ADFI, lb/day | 2.97 | 2.94 | 2.83 | 0.04 | 0.10 | −1.1% | −4.8% |
| F/G | 1.80 | 1.78 | 1.76 | 0.03 | 0.10 | −1.0% | −2.2% |
| BW end of Phase 2, lb | 77.1 | 76.7 | 76.8 | 0.4 | 0.50 | −0.4 lb | −0.3 lb |
| *Phase 3; 11 days* | | | | | | | |
| ADG, lb/day | 2.15 | 2.15 | 2.08 | 0.02 | 0.08 | 0.1% | −3.3% |
| ADFI, lb/day | $3.87^{ab}$ | $3.94^a$ | $3.71^b$ | 0.05 | 0.003 | 1.8% | −4.2% |
| F/G | 1.80 | 1.83 | 1.78 | 0.02 | 0.39 | 1.7% | −0.9% |
| BW end of Phase 3, lb | 100.9 | 100.5 | 99.8 | 0.6 | 0.54 | −0.4 lb | −1.1 lb |
| *Phase 4; 15 days* | | | | | | | |
| ADG, lb/day | 1.91 | 1.90 | 1.94 | 0.03 | 0.44 | −0.5% | 1.7% |
| ADFI, lb/day | 3.77 | 3.77 | 3.69 | 0.04 | 0.38 | 0.1% | −2.1% |
| F/G | 1.98 | 1.99 | 1.91 | 0.03 | 0.09 | 0.6% | −3.5% |
| BW end of Phase 4, lb | 129.7 | 128.9 | 129.4 | 0.8 | 0.85 | −0.8 lb | −0.4 lb |
| *Phase 5; 20 days* | | | | | | | |
| ADG, lb/day | $1.88^a$ | $1.93^{ab}$ | $1.99^{bc}$ | 0.03 | 0.003 | 2.7% | 5.8% |
| ADFI, lb/day | 4.65 | 4.58 | 4.57 | 0.06 | 0.56 | −1.6% | −1.8% |
| F/G | $2.49^a$ | $2.37^{ab}$ | $2.29^{bc}$ | 0.04 | 0.0003 | −4.8% | −8.0% |
| BW end of Phase 5, lb | 167.1 | 167.5 | 169.5 | 1.1 | 0.20 | 0.4 lb | 2.4 lb |

TABLE 16-continued

Growth Performance

| Item | Control | DFM 1[1] | DFM 2[1] | PSE | P-value | DFM 1 vs. CON | DFM 2 vs. CON |
|---|---|---|---|---|---|---|---|
| Phase 6, 7 days | | | | | | | |
| ADG, lb/day | 1.97 | 2.00 | 1.95 | 0.04 | 0.73 | 1.4% | −1.3% |
| ADFI, lb/day | 4.86 | 4.99 | 4.94 | 0.08 | 0.14 | 2.8% | 1.6% |
| F/G | 2.47 | 2.51 | 2.54 | 0.05 | 0.67 | 1.8% | 2.9% |
| BW end of Phase 6, lb | 181.6 | 181.7 | 183.1 | 1.2 | 0.45 | 0.0 lb | 1.5 lb |
| Overall; Phase 1 to 6; 77 days | | | | | | | |
| ADG, lb/day | 1.84 | 1.84 | 1.85 | 0.02 | 0.47 | 0.1% | 0.8% |
| ADFI, lb/day | 3.67 | 3.66 | 3.60 | 0.03 | 0.39 | −0.1% | −1.8% |
| F/G | 2.00$^a$ | 1.99$^{ab}$ | 1.95$^b$ | 0.02 | 0.02 | −0.6% | −2.9% |
| BW gain, lb | 142.2 | 142.2 | 143.6 | 1.2 | 0.43 | 0.0% | 1.0% |
| Feed consumed per head, lb | 284.8 | 283.3 | 279.5 | 2.4 | 0.39 | −0.5% | −1.9% |
| Removal, % | 2.7 | 2.7 | 4.3 | N/A | 0.51 | N/A | N/A |
| Treated pigs, % | 0.7 | 0.3 | 0.9 | N/A | 0.25 | N/A | N/A |
| Pen performance | | | | | | | |
| Pen ADG, lb/day | 48.0 | 48.2 | 47.6 | 0.8 | 0.57 | 0.3% | −0.9% |
| Pen ADFI, lb/day | 97.5 | 97.2 | 95.5 | 1.3 | 0.62 | −0.3% | −2.1% |
| Pen F/G | 2.03 | 2.02 | 2.01 | 0.02 | 0.15 | −0.7% | −1.3% |

[1]DFM 1 = strain 1781, DFM 2 = strain 2018
$^{a,b,c}$Means without a common superscript differ (P < 0.05)

Example 9: *Bacillus subtilis* Strains Decrease Enteric *E. coli* and *Clostridium*, as Well as Modulate Immunological Responses in Pigs A seven-day study was conducted to evaluate the potential of three *Bacillus subtilis* strains and a two-strain *Bacillus* combination to decrease the naturally occurring enteric populations of *E. coli* and *Clostridium*, as well as to modulate immune characteristics in newly weaned pigs. A total of 100 weanling barrows with a weaning age from 18-21 days of age were identified for the study. Pigs were divided into fifty pens with two pigs per pen and randomly assigned to one of five treatments: A) a control basal diet; B) *B. subtilis* 747; C) *B. subtilis* 1781; D) *B. subtilis* 1999; and E), *B. subtilis* 1781+*B. subtilis* 747. Each dietary *Bacillus* treatment was formulated to contain a total of $1.5 \times 10^5$ CFU/g of feed regardless if the treatment contained a single *Bacillus* strain or a combination of two *Bacillus* strains (Table 17). Diets were fed for seven days after weaning. Pigs assigned to a *Bacillus* treatment received an oral dose consisting of a 2 mL solution of their respective treatment strain(s) for three consecutive days immediately after weaning at the start of the trial. Each respective treatment was prepared by mixing the dry *Bacillus* material into water at a ratio of 500 mg *Bacillus*:2 mL of water, such that each 2 mL dose delivered $1.7 \times 10^8$ CFU/head/day. Pigs were weighed and FI was determined to calculate ADG, ADFI, and feed efficiency (Feed:Gain). Fecal scores using the fecal consistency scoring system described by Marquardt et al. (1999) were measured by trained personnel with no knowledge of the treatment assignments, and fecal samples were obtained from pigs at the beginning and end of the trial to determine *E. coli* and *Clostridium* counts. Two separate blood samples were obtained at the end of the study, one to obtain serum for cytokine analysis and the second in PAXgen Blood RNA tubes for gene expression measurements of immune cell characteristics.

TABLE 17

Dietary Treatments

| Treatment | Testing Product | Testing Product Inclusion | # Pigs per Pen | # of Pens | Total # Pigs |
|---|---|---|---|---|---|
| A | Control | None | 2 | 10 | 20 |
| B | 747 | 2.0 lb/ton[1] | 2 | 10 | 20 |
| C | 1781 | 2.0 lb/ton[1] | 2 | 10 | 20 |
| D | 1999 | 2.0 lb/ton[1] | 2 | 10 | 20 |
| E | 747 + 1781 | 2.0 lb/ton[1] | 2 | 10 | 20 |

[1]inclusion rate of 2.0 lb/ton of product will provide $1.5 \times 10^5$ CFU/g of feed.

TABLE 18

*Escherichia coli* and *Clostridium* fecal counts from weanling pigs on Day 0 and Day 7 post-weaning fed three different *Bacillus* strains and a combination.

| | E. coli | | Clostridium | |
|---|---|---|---|---|
| Treatment | Day 0 | Day 7 | Day 0 | Day 7 |
| Control | 7.70 | 6.47 | 7.62 | 6.04 $^a$ |
| ABS747 | 8.00 | 7.07 | 7.17 | 5.44 $^{a,b}$ |
| ABS1781 | 8.14 | 7.04 | 7.05 | 5.99 $^a$ |
| ABS1999 | 8.01 | 6.75 | 7.48 | 5.06 $^{b,c}$ |
| ABS747 + ABS1781 | 8.17 | 7.05 | 7.19 | 4.44 $^c$ |
| SE | 0.27 | 0.27 | 0.33 | 0.31 |
| P-value | 0.744 | 0.550 | 0.644 | <0.01 |

$^{a,b,c}$ Means without a common superscript differ significantly (P < 0.05).

Although there was no difference in *E. coli* counts between pigs fed the different treatments at Day 0 or Day 7 of the study, the administration of *Bacillus* treatments for seven days reduced fecal *E. coli* counts compared to baseline counts (Day 0; Table 18). The administration of *Bacillus* ABS1999 and the combination treatment of *Bacillus* ABS747+ABS1781 substantially reduced (P<0.05) *Clostridium* counts on Day 7 compared to control pigs, such that the two *Bacillus* treatments resulted in over two log reduction in *Clostridium* counts compared to baseline counts on Day 0 compared to only about a one log reduction for control pigs. Furthermore, the *Bacillus* combination resulted in a substantially greater reduction in *Clostridium* counts compared to the administration of either of the strains singly. The immune data analysis from this study is currently underway, and it is expected that pigs administered the *Bacillus* treatments will also have different immunological characteristics compared to the control as well as divergent immunological measures between pigs fed the individual *Bacillus* treatments.

Example 10. Bacterial Populations Differ in Pathogenicity Between Swine and Poultry The pathogenicity of a specific bacterial species is associated with the presence of pathogenic genes that when expressed, result in a diseased state in the host. For example in swine, pathogenicity associated with *E. coli* is based on the presence of adhesion genes that allow the *E. coli* to attached to the intestinal epithelium and toxigenic genes that identify a specific strain of *E. coli* as having the ability to produce enteric toxin compounds in the host. The enteric distress that results when swine are infected with pathogenic *E. coli* is a result of the disruption of the intestinal epithelium from *E. coli* attachment and toxin production. In contrast, avian pathogenic *E. coli* that cause disease in commercial poultry flocks are associated with genes that allow the *E. coli* to persist in the avian host. Table 19 illustrates this difference between swine and avian pathogenic *E. coli*, showing the adhesion and toxin genes used to identify pathogenic *E. coli* in swine and the genes related to membrane stabilization and iron metabolism that are used to identify avian pathogenic *E. coli*.

TABLE 19

PCR gene targets for poultry and swine Microbial Terroir platforms
Pathogenic *E. coli* gene screening targets

| Gene target | Function | Poultry | Swine |
| --- | --- | --- | --- |
| faeG | Adhesin F4 (K88) | | X |
| fanA | Adhesin F5 (K99) | | X |
| fasA | Adhesin F6 (987P) | | X |
| fedA | Adhesin F41 | | X |
| fedA | Adhesin F18 | | X |
| eltB | Heat-labile toxin (LT) | | X |
| estA | Heat-stable toxin a (STa) | | X |
| estB | Heat-stable toxin b (STb) | | X |
| stx2eA | shiga toxin (Stx2eA) | | X |
| hlyF | Regulates outer-membrane vesicles | X | |
| ompT | outer-membrane protease | X | |
| iroN | Siderophore uptake | X | |
| iss | Increased serum survival | X | |
| iutA | Siderophore receptor | X | |

REFERENCES

Aperce, C. C., T. E. Burkey, B. KuKanich, B. A. Crozier-Dodson, S. S. Dritz, and J. E. Minton. 2010. Interaction of *Bacillus* species and *Salmonella enterica* serovar Typhimurium in immune or inflammatory signaling from swine intestinal epithelial cells. J. Anim. Sci. 88:1649-1656.

Baker, A. A., E. Davis, T. Rehberger, and D. Rosener. 2010. Prevalence and diversity of toxigenic *Clostridium perfringens* and *Clostridium difficile* among swine herds in the Midwest. Appl. Env. Microbiol. 76:2961-2967.

Baker, A. A., E. Davis, J. D. Spencer, R. Moser, and T. Rehberger. 2013. The effect of a *Bacillus*-based direct-fed microbial supplemented to sows on the gastrointestinal microbiota of their neonatal piglets. J. Anim. Sci. 91:3390-3399.

Bertschinger, J. U., and J. M. Fairbrother. 1999. *Escherichia coli* infections. In B. E. Straw, S. D'Allaire, W. L. Mengeling, and D. J. Taylor (Eds.), Diseases of swine (8$^{th}$ Edition, Chapter 32). Ames, Iowa: Iowa State University Press.

Chen, Y. J., B. J. Min, J. H. Cho, O. S. Kwon, K. S. Son, H. J. Kim, and I. H. Kim. 2006. Effects of dietary *Bacillus*-based probiotic on growth performance, nutrients digestibility, blood characteristics and fecal noxious gas content in finishing pigs. Asian-Aust. J. Anim. Sci. 4:587-592.

Cheng, G., H. Haihong, S. Xie, X. Wang, M. Dai, L. Huang, and Z. Yuan. 2014. Antibiotic alternatives: the substitution of antibiotics in animal husbandry? Frontiers Microbiol. 5:1-15.

Davis, M. E., T. Parrott, D. C. Brown, B. Z. de Rodas, Z. B. Johnson, C. V. Maxwell, and T. Rehberger. 2008. Effect of a *Bacillus*-based direct-fed microbial feed supplement on growth performance and pen cleaning characteristics of growing-finishing pigs. J. Anim. Sci. 86:1459-1467.

Gottschalk, M., J. Xu, C. Calzas, and M. Segura. 2010. *Streptococcus suis*: a new emerging or an old neglected zoonotic pathogen? Future Microbiol. 5:371-391.

Gu, S., L. Zhou, Y. Wu, S. Li, J. Sun, J. Huang, and D. Li. 2015. Potential probiotic attributes of a new strain of *Bacillus coagulans* CGMCC 9951 isolated from health piglet feces. World J. Microbiol. Biotechnol. 31:851-863.

Haesebrouck, F., F. Pasmans, K. Chiers, D. Maes, R. Ducatelle, and A. Decostere. 2004. Efficacy of vaccines against bacterial diseases in swine: what can we expect? Vet. Microbiol. 100:255-268.

Hentges, D. J. 1992. Gut flora in disease resistance. pp. 87-110. In Probiotics: the scientific basis, Fuller R., ed. Chapman and Hall, London, UK.

Holdkamp, D. J. 2007. Economic cost of major health challenges in large US swine production Systems—Part 1. The Pig Site.

Holtkamp, D. J., J. B. Kliebenstein, E. J. Neumann, J. J. Zimmerman, H. F. Rotto, T. K. Yoder, C. Wang, P. E. Yeske, C. L. Mower, and C. A Haley. 2013. Assessment of the economic impact of porcine reproductive and respiratory syndrome virus on United States pork producers. J. Swine Health and Production. March and April 2013, pp 72-84.

Hong, H. A., I. H. Duc, and S. M. Cutting. 2005. The use of bacterial spore formers as probiotics. FEMS Microbiol. Rev. 29:813-835.

Hu, Y., Y. Dun, S. Li, S. Zhao, N. Peng, and Y. Liang. 2014. Effects of *Bacillus subtilis* KN-42 on growth performance, diarrhea and faecal bacterial flora of weaned piglets. Asian-Aust. J. Anim. Sci. 27:1131-1140.

Kalemba, D., and A. Kunicka. 2003. Antibacterial and antifungal properties of essential oils. Current Medicinal Chemistry. 10:813-829.

Klose, V., K. Bayer, R. Bruckbeck, G. Schatzmayr, and A. Loibner. 2010. In vitro antagonistic activities of animal intestinal strains against swine-associated pathogens. Vet. Microbiol. 144:515-521.

Kluge, H., J. Broz, and K. Eder. 2006. Effect of benzoic acid on growth performance, nutrient digestibility, nitrogen balance, gastrointestinal microflora and parameters of microbial metabolism in piglets. J. Anim. Physiol. Anim. Nutr. 90:316-324.

Kritas, S. K., T. Marubashi, G. Filoussis, E. Petridou, G. Christodoulopoulos, A. R. Burriel, A. Tzivara, A. Theodoridis, and M. Piskorikova. 2015. Reproductive performance of sows was improved by administration of a sporing bacillary probiotic (*Bacillus subtilis* C-3102). J. Anim. Sci. 93:405-413.

Marquardt, R. R., L. Z. Jin, J. W. Kim, L. Fang, A. A. Frohlich and S. K. Baidoo. 1999. Passive protective effect of egg-yolk antibodies against enterotoxigenic *Escherichia coli* K88+ infection in neonatal and early-weaned piglets. FEMS Immunol Med Microbiol 23: 283-288.

Nietfeld, J. C., I. Feder, T. T. Kramer, D. Schoneweis, and M. M. Chengappa. 1998. Preventing *Salmonella* infection in pigs with offsite weaning. Swine Health Prod. 6:27-32.

Shariat, N., C. H. Sandt, M. J. DiMarzio, R. Barrangou, and E. G. Dudley. 2013. CRISPR-MVLST subtyping of *Salmonella enterica* subsp. *enterica* serovars Typhimurium and Heidelberg and application in identifying outbreak isolates. BMC Microbiol. 13:254.

Songer, J. G., K. W. Post, D. J. Larson, B. H. Jost, and R. D. Glock. 2000. Infection of neonatal swine with *Clostridium difficile*. Swine Health Prod. 8:185-189.

Taylor, D. J. 2013. Pig Diseases (9$^{th}$ Edition). 5m Publishing, Sheffield, England.

Thanawongnuwech, R. G. B. Brown, P. G. Halbur, J. A. Roth, R. L. Royer, and B. J. Thacker. 2000. Pathogenesis of porcine reproductive and respiratory syndrome virus-induced increase in susceptibility to *Streptococcus suis* infection. Vet. Pathol. 37:143-152.

Tsukahara, T., T. Tsuruta, N. Nakanishi, C. Hikita, M. Mochizuki, and K. Nakayama. 2013. The preventive effect of *Bacillus subtilus* strain DB9011 against experimental infection with enterotoxcemic *Escherichia coli* in weaning piglets. Anim. Sci. J. 84:316-321.

Upadhaya, S. D., S. K. Shanmugam, D. K. Kang, and I. H. Kim. 2017. Preliminary assessment on potentials of probiotic *B. subtilis* RX7 and *B. methylotrophicus* C14 strains as an immune modulator in *Salmonella*-challenged weaned pigs. Tropical Anim. Health Prod. 49:1065-1070.

Vallet, J. L., J. R. Miles and L. A. Rempel. 2013. A simple novel measure of passive transfer of maternal immunoglobulin is predictive of preweaning mortality in piglets. The Veterinary Journal 195:91-97.

Vondruskova, H., R. Slamova, M. Trckova, Z. Zraly, and I. Pavlik. 2010. Alternatives to antibiotic growth promotors in prevention of diarrhea in weaned piglets: a review. Veterinarni Medicina 55:199-224.

Walsh, M. C., M. H. Rostangno, G. E. Gardiner, A. L. Sutton, B. T. Richert, and J. S. Radcliffe. 2012a. Controlling *Salmonella* infection in weanling pigs through water delivery of direct-fed microbials or organic acids. Part I: Effects on growth performance, microbial populations, and immune status. J. Anim. Sci. 90:261-271.

Walsh, M. C., M. H. Rostangno, G. E. Gardiner, A. L. Sutton, B. T. Richert, and J. S. Radcliffe. 2012b. Controlling *Salmonella* infection in weanling pigs through water delivery of direct-fed microbials or organic acids. Part II: Effects on intestinal histology and active nutrient transport. J. Anim. Sci. 90:2599-2608

Yang, G., Y. Zhu, W. Zhang, D. Zhou, C. Zhai, and J. Wang. 2016. Influence of orally fed a select mixture of *Bacillus* probiotics on intestinal T-cell migration in weaned MUC4 resistant pigs following *Escherichia coli* challenge. Vet. Res. 47:71.

Zimmerman, J. J., L. A. Karriker, A. Ramirez, K. J. Schwartz, and G. W. Stevenson. 2012. Diseases of Swine (10$^{th}$ Edition). John Wiley & Sons, Hoboken, N.J.

---

The invention claimed is:

1. A direct fed microbial composition comprising
   (a) an isolated *Bacillus* strain, wherein the isolated *Bacillus* strain is chosen from at least one of strains *Bacillus subtilis* 747, deposited as NRRL B-67257; *Bacillus subtilis* 1104, deposited as NRRL B-67258; *Bacillus subtilis* 1541, deposited as NRRL B-67260; *Bacillus subtilis* 1781, deposited as NRRL B-67259; *Bacillus subtilis* 2018, deposited as NRRL B-67261; and *Bacillus subtilis* 1999, deposited as NRRL B-67318; and
   (b) a preservative;
   wherein said isolated *Bacillus* strain is a powdered lyophilized isolated *Bacillus* strain, and
   wherein the composition inhibits at least one pathogen selected from *Escherichia coli, Salmonella, Clostridia,* and *Streptococcus suis* by at least 85% overall *in vitro*.

2. The composition of claim 1, wherein the composition comprises a combination of at least two isolated *Bacillus* strains chosen from strains *Bacillus subtilis* 747, *Bacillus subtilis* 1104, *Bacillus subtilis* 1541, *Bacillus subtilis* 1781, *Bacillus subtilis* 2018, and *Bacillus subtilis* 1999.

3. The composition of claim 1, further comprising a carrier.

4. The composition of claim 1, further comprising a cryoprotectant disposed about the isolated *Bacillus* strain, and wherein said powdered lyophilized isolated *Bacillus* strain comprises *Bacillus* spores.

5. The composition of claim 1, further comprising an animal feed.

6. The composition of claim 5, wherein the composition has a concentration of the isolated *Bacillus* strain in the composition of between about $1 \times 10^5$ CFU/g of feed and about $1 \times 10^6$ CFU/g of feed.

7. The composition of claim 6, wherein the composition has a concentration of the isolated *Bacillus* strain in the composition of about $3.75 \times 10^5$ CFU/g of feed.

8. The composition of claim 1, wherein the effective amount of said direct fed microbial composition ingested by the swine per day comprises a concentration of the isolated *Bacillus* strain of between about $1 \times 10^6$ CFU/swine and about $1 \times 10^9$ CFU/swine.

9. The composition of claim 1, wherein the composition improves the fecal score of the swine at seven days post weaning, wherein the swine ingested the effective amount of said direct fed microbial composition between zero days and seven days post weaning from the sow.

10. The composition of claim 1, wherein the composition improves the average fecal score of the swine during an initial 14 days of a nursery period, wherein the swine ingested the effective amount of said direct fed microbial composition between zero days and 14 days post weaning from the sow.

11. The composition of claim 1, wherein the composition further inhibits *Escherichia coli* in the gastrointestinal tract of the swine at least seven days after the swine ingested the effective amount of said direct fed microbial composition.

12. The composition of claim 1, wherein the composition further inhibits *Salmonella* in the gastrointestinal tract of the swine at least seven days after the swine ingested the effective amount of said direct fed microbial composition.

13. The composition of claim 1, wherein the composition further inhibits *Clostridia* in the gastrointestinal tract of the swine at least seven days after the swine ingested the effective amount of said direct fed microbial composition.

14. The composition of claim 1, wherein the composition inhibits *Streptococcus suis* in the gastrointestinal tract of the swine at least seven days after the swine ingested the effective amount of said direct fed microbial composition.

15. A direct fed microbial composition comprising:
   a cryoprotectant disposed about a powdered lyophilized isolated *Bacillus* strain of spores chosen from at least one of: *Bacillus subtilis* 747, *Bacillus subtilis* 1104, *Bacillus subtilis* 1541, *Bacillus subtilis* 1781, *Bacillus subtilis* 2018, and *Bacillus subtilis* 1999, and
   a preservative,
   wherein said direct fed microbial composition improves performance of a swine that has ingested the direct fed microbial composition in an effective amount, wherein the effective amount of said direct fed microbial composition comprises a concentration of the isolated *Bacillus* strain of between about $1 \times 10^6$ CFU/swine/day and about $1 \times 10^9$ CFU/swine/day.

16. The direct fed microbial composition of claim 15, wherein the effective amount of said direct fed microbial composition inhibits at least one pathogen selected from *Escherichia coli*, *Salmonella*, *Clostridia*, and *Streptococcus suis* in the gastrointestinal tract of the swine.

* * * * *

SEQUENCE LISTING

```
<160> NUMBER OF SEQ ID NOS: 31

<210> SEQ ID NO 1
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: Stx2eF
<222> LOCATION: (1)..(20)

<400> SEQUENCE: 1
aatagtatac ggacagcgat                                           20

<210> SEQ ID NO 2
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: Stx2eR
<222> LOCATION: (1)..(20)

<400> SEQUENCE: 2
tctgacattc tggttgactc                                           20

<210> SEQ ID NO 3
<211> LENGTH: 20
<212> TYPE: DNA
<213> ORGANISM: Artificial Sequence
```

```
<220> FEATURE:
<223> OTHER INFORMATION: Synthetic
<220> FEATURE:
<221> NAME/KEY: LTbF
<222> LOCATION: (1)..(20)

<400> SEQUENCE: 3
ggcgttacta tcctctctat                                              20

<210> SEQ ID NO 4
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: LTbR
<222> LOCATION: (1)..(19)

<400> SEQUENCE: 4
tggtctcggt cagatatgt                                               19

<210> SEQ ID NO 5
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: STaPF
<222> LOCATION: (1)..(21)

<400> SEQUENCE: 5
caactgaatc acttgactct t                                            21

<210> SEQ ID NO 6
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: STaPR
<222> LOCATION: (1)..(20)

<400> SEQUENCE: 6
ttaataacat ccagcacagg                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: STbF
<222> LOCATION: (1)..(20)

<400> SEQUENCE: 7
tgcctatgca tctacacaat                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic
```

```
<220> FEATURE:
<221> NAME/KEY: STbR
<222> LOCATION: (1)..(20)

<400> SEQUENCE: 8
ctccagcagt accatctcta                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: F18F
<222> LOCATION: (1)..(20)

<400> SEQUENCE: 9
tggtaacgta tcagcaacta                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: F18R
<222> LOCATION: (1)..(20)

<400> SEQUENCE: 10
acttacagtg ctattcgacg                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: F41F
<222> LOCATION: (1)..(20)

<400> SEQUENCE: 11
agtatctggt tcagtgatgg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: F41R
<222> LOCATION: (1)..(20)

<400> SEQUENCE: 12
ccactataag aggttgaagc                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic
```

```
<220> FEATURE:
<221> NAME/KEY: K99F
<222> LOCATION: (1)..(20)

<400> SEQUENCE: 13
aatacttgtt cagggagaaa                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: K99R
<222> LOCATION: (1)..(20)

<400> SEQUENCE: 14
aactttgtgg ttaacttcct                                                 20

<210> SEQ ID NO 15
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: 987PF
<222> LOCATION: (1)..(20)

<400> SEQUENCE: 15
aagttactgc cagtctatgc                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: 987PR
<222> LOCATION: (1)..(20)

<400> SEQUENCE: 16
gtaactccac cgtttgtatc                                                 20

<210> SEQ ID NO 17
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: K88F
<222> LOCATION: (1)..(20)

<400> SEQUENCE: 17
gttggtacag gtcttaatgg                                                 20

<210> SEQ ID NO 18
<211> LENGTH: 20
<212> TYPE: DNA
<213> ORGANISM: Artificial Sequence
<220> FEATURE:
<223> OTHER INFORMATION: Synthetic
```

```
<220> FEATURE:
<221> NAME/KEY: K88R
<222> LOCATION: (1)..(20)

<400> SEQUENCE: 18
gaatctgtcc gagaatatca                                          20

<210> SEQ ID NO 19
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: CPA-F
<222> LOCATION: (1)..(24)

<400> SEQUENCE: 19
gttgatagcg caggacatgt taag                                     24

<210> SEQ ID NO 20
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: CPA-R
<222> LOCATION: (1)..(24)

<400> SEQUENCE: 20
catgtagtca tctgttccag catc                                     24

<210> SEQ ID NO 21
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: CPB-F
<222> LOCATION: (1)..(24)

<400> SEQUENCE: 21
actatacaga cagatcattc aacc                                     24

<210> SEQ ID NO 22
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: CPB-R
<222> LOCATION: (1)..(24)

<400> SEQUENCE: 22
ttaggagcag ttagaactac agac                                     24

<210> SEQ ID NO 23
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: CPE-F
<222> LOCATION: (1)..(24)
```

```
<400> SEQUENCE: 23
actgcaacta ctactcatac tgtg                                          24

<210> SEQ ID NO 24
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: CPE-R
<222> LOCATION: (1)..(24)

<400> SEQUENCE: 24
ctggtgcctt aatagaaaga ctcc                                          24

<210> SEQ ID NO 25
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: CPI-F
<222> LOCATION: (1)..(24)

<400> SEQUENCE: 25
gcgatgaaaa gcctacacca ctac                                          24

<210> SEQ ID NO 26
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: CPI-R
<222> LOCATION: (1)..(24)

<400> SEQUENCE: 26
ggtatatcct ccacgcatat agtc                                          24

<210> SEQ ID NO 27
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: RAPDprimer
<222> LOCATION: (1)..(10)

<400> SEQUENCE: 27
gtttcgctcc                                                          10

<210> SEQ ID NO 28
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: invA-F
<222> LOCATION: (1)..(22)

<400> SEQUENCE: 28
gatytgaarg ccggtattat tg                                            22
```

```
<210> SEQ ID NO 29
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: invA-R
<222> LOCATION: (1)..(20)

<400> SEQUENCE: 29
ataaacttca cgcaccgtca                                                      20

<210> SEQ ID NO 30
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: 27F-YM
<222> LOCATION: (1)..(20)

<400> SEQUENCE: 30
agagtttgat ymtggctcag                                                      20

<210> SEQ ID NO 31
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: 1492R-Y
<222> LOCATION: (1)..(16)

<400> SEQUENCE: 31
taccttgtta ygactt                                                          16
```